US011865144B2

(12) United States Patent
Anker et al.

(10) Patent No.: US 11,865,144 B2
(45) Date of Patent: Jan. 9, 2024

(54) IMMUNOSTIMULATORY BACTERIA FOR THE TREATMENT OF CANCER

(71) Applicant: Northwestern University, Evanston, IL (US)

(72) Inventors: Jonathan F. Anker, Chicago, IL (US); Praveen Thumbikat, Chicago, IL (US); Sarki A. Abdulkadir, Lombard, IL (US); Anthony J. Schaeffer, Hinsdale, IL (US)

(*) Notice: Subject to any disclaimer, the term of this patent is extended or adjusted under 35 U.S.C. 154(b) by 320 days.

(21) Appl. No.: 16/052,285

(22) Filed: Aug. 1, 2018

(65) Prior Publication Data

US 2019/0046588 A1 Feb. 14, 2019

Related U.S. Application Data

(60) Provisional application No. 62/539,843, filed on Aug. 1, 2017.

(51) Int. Cl.
| | | |
|---|---|---|
| A61K 35/74 | (2015.01) | |
| A61P 35/00 | (2006.01) | |
| A61K 45/06 | (2006.01) | |
| A61K 39/00 | (2006.01) | |
| C07K 16/28 | (2006.01) | |
| A61K 39/108 | (2006.01) | |
| A61K 39/395 | (2006.01) | |

(52) U.S. Cl.
CPC ...... *A61K 35/74* (2013.01); *A61K 39/001193* (2018.08); *A61K 39/001194* (2018.08); *A61K 39/0258* (2013.01); *A61K 39/3955* (2013.01); *A61K 45/06* (2013.01); *A61P 35/00* (2018.01); *C07K 16/2818* (2013.01); *A61K 2039/505* (2013.01); *A61K 2039/523* (2013.01); *A61K 2039/585* (2013.01); *A61K 2039/884* (2018.08); *C12N 2740/16043* (2013.01)

(58) Field of Classification Search
None
See application file for complete search history.

(56) References Cited

U.S. PATENT DOCUMENTS 8,449,878 B2   5/2013   Yonak et al.

FOREIGN PATENT DOCUMENTS

WO   WO-2016075687 A2 *  5/2016  ........... A61K 9/0034

OTHER PUBLICATIONS

Rudick et al., Infection and Immunity, vol. 79, No. 2, pp. 628-635; 2011 (of record). (Year: 2011).*
Basnet et al., Clinical Genitourinary Cancer, vol. 15, No. 5, pp. e881-e884; electronically published May 24, 2017. (Year: 2017).*
Simons et al., Journal of Pathology, vol. 235, No. 3, pp. 478-489; 2015 (of record). (Year: 2015).*
Sambrook et al., Molecular Cloning, A Laboratory Manual, Second edition; 1989 (of record). (Year: 1989).*
Miller, J.H., Experiments in Molecular Genetics; 1972 (of record). (Year: 1972).*
Miller, J.H., AShortCourse in in Bacterial Genetics; 1992 (of record). (Year: 1992).*
Basnet et al., Clinical Genitourinary Cancer, vol. 15, No. 5, pp. e881-e884; May 24, 2017 (of record). (Year: 2017).*
Ahmad, S., et al. Induction of effective antitumor response after mucosal bacterial vector mediated DNA vaccination with endogenous prostate cancer specific antigen. J Urol. Aug. 2011;186(2):687-93.
Alexandrov, L.B., et al., Signatures of mutational processes in human cancer. Nature. Aug. 22, 2013;500(7463):415-21.
Alibhai, S.M., et al., 30-day mortality and major complications after radical prostatectomy: influence of age and comorbidity. J Natl Cancer Inst. Oct. 19, 2005;97(20).
Ausubel, F.M. et al., Current Protocols in Molecular Biology, Greene Publishing and Wiley-Interscience (1987).
Barach, Y.S., et al. T cell coinhibition in prostate cancer: new immune evasion pathways and emerging therapeutics. Trends Mol Med. Jan. 2011;17(1):47-55.
Berthold, D.R., et al., Docetaxel plus prednisone or mitoxantrone plus prednisone for advanced prostate cancer: updated survival in the TAX 327 study. J Clin Oncol. Jan. 10, 2008;26(2):242-5.
Bracarda, S., et al., Comparing comparators: a look at control arms in kidney cancer studies over the years. Br J Cancer. Jan. 6, 2015;112(1):14-9.
Cancer Genome Atlas Research, N., The Molecular Taxonomy of Primary Prostate Cancer. Cell, 2015. 163(4): p. 1011-25.
Cerami, E., et al., The cBio cancer genomics portal: an open platform for exploring multidimensional cancer genomics data. Cancer Discov. May 2012;2(5):401-4.
Champiat, S., et al., Exomics and immunogenics: Bridging mutational load and immune checkpoints efficacy. Oncoimmunology. Jan. 1, 2014;3(1):e27817.
Coley, W.B., The Treatment of Inoperable Sarcoma by Bacterial Toxins (the Mixed Toxins of the *Streptococcus erysipelas* and the Bacillus prodigiosus). Proc R Soc Med. 1910;3(Surg Sect):1-48.
Davis, et al. Advanced Bacterial Genetics. Cold Spring Harbor Laboratory, 1980.
De Bono, J.S., et al., Prednisone plus cabazitaxel or mitoxantrone for metastatic castration-resistant prostate cancer progressing after docetaxel treatment: a randomised open-label trial. Lancet. Oct. 2, 2010;376(9747):1147-54.
Demaria, S., et al., Immune-mediated inhibition of metastases after treatment with local radiation and CTLA-4 blockade in a mouse model of breast cancer. Clin Cancer Res. Jan. 15, 2005;11 (2 Pt 1):728-34.
Denis, L. et al., Overview of phase III trials on combined androgen treatment in patients with metastatic prostate cancer. Cancer. Dec. 15, 1993;72(12 Suppl):3888-95.

(Continued)

*Primary Examiner* — Vera Afremova
(74) *Attorney, Agent, or Firm* — Casimir Jones, SC; David W. Staple

(57) ABSTRACT

Provided herein are composition and methods for the treatment of cancer by the administration of uropathogenic bacteria. In particular, CP1 *E. coli* is administered for the treatment of prostate cancer.

7 Claims, 54 Drawing Sheets

Specification includes a Sequence Listing.

(56) References Cited

OTHER PUBLICATIONS

Domingo-Domenech, J., et al., Interleukin 6, a nuclear factor-kappaB target, predicts resistance to docetaxel in hormone-independent prostate cancer and nuclear factor-kappaB inhibition by PS-1145 enhances docetaxel antitumor activity. Clin Cancer Res. Sep. 15, 2006;12(18):5578-86.

Dulos, J., et al., PD-1 blockade augments Th1 and Th17 and suppresses Th2 responses in peripheral blood from patients with prostate and advanced melanoma cancer. J Immunother. Feb.-Mar. 2012;35(2):169-78.

Ebelt, K., et al., Prostate cancer lesions are surrounded by FOXP3+, PD-1+ and B7-H1+ lymphocyte clusters. Eur J Cancer. Jun. 2009;45(9):1664-72.

Ellis, L., et al., Development of a castrate resistant transplant tumor model of prostate cancer. Prostate. May 1, 2012;72(6):587-91.

Ellis, L., et al., Generation of a syngeneic orthotopic transplant model of prostate cancer metastasis. Oncoscience. Oct. 15, 2014;1(10):609-613.

Experimental Techniques in Bacterial Genetics (Maloy, in Jones and Bartlett, 1990).

Fensterle, J., et al., Cancer immunotherapy based on recombinant *Salmonella enterica* serovar Typhimurium aroA strains secreting prostate-specific antigen and cholera toxin subunit B. Cancer Gene Ther. Feb. 2008;15(2):85-93.

Fizazi, K., et al., Abiraterone acetate for treatment of metastatic castration-resistant prostate cancer: final overall survival analysis of the COU-AA-301 randomised, double-blind, placebo-controlled phase 3 study. Lancet Oncol. Oct. 2012;13(10):983-92.

Galluzzi, L., et al., Immunogenic cell death in cancer and infectious disease. Nat Rev Immunol. Feb. 2017;17(2):97-111.

Gao, J., et al., Integrative analysis of complex cancer genomics and clinical profiles using the cBioPortal. Sci Signal. Apr. 2, 2013;6(269):pl1.

Gevenleben, H., et al., The Immune Checkpoint Regulator PD-L1 is Highly Expressed in Aggressive Primary Prostate Cancer. Clin Cancer Res. Apr. 15, 2016;22(8):1969-77.

Green, D.R., et al., Immunogenic and tolerogenic cell death. Nat Rev Immunol. May 2009;9(5):353-63.

Hannani, D., et al., Harnessing gammadelta T cells in anticancer immunotherapy. Trends Immunol. May 2012;33(5):199-206.

Hellerstedt, B.A. et al. The current state of hormonal therapy for prostate cancer. CA Cancer J Clin. May-Jun. 2002;52(3):154-79.

Hobisch, A., et al., Interleukin-6 regulates prostate-specific protein expression in prostate carcinoma cells by activation of the androgen receptor. Cancer Res. Oct. 15, 1998;58(20):4640-5.

Hodi, F. S. et al. Improved survival with ipilimumab in patients with metastatic melanoma. N Engl J Med. Aug. 19, 2010;363(8):711-23.

Hudson, et al. Engineered antibodies. Nat Med. Jan. 2003;9(1):129-34.

Jiang, S.N., et al., Engineering of bacteria for the visualization of targeted delivery of a cytolytic anticancer agent. Mol Ther. Nov. 2013;21(11):1985-95.

Jiang, S.N., et al., Inhibition of tumor growth and metastasis by a combination of *Escherichia coli*-mediated cytolytic therapy and radiotherapy. Mol Ther. Mar. 2010;18(3):635-42.

Kantoff, P.W., et al., Sipuleucel-T immunotherapy for castration-resistant prostate cancer. N Engl J Med. Jul. 29, 2010;363(5):411-22.

Karja, V., et al., Tumour-infiltrating lymphocytes: A prognostic factor of PSA-free survival in patients with local prostate carcinoma treated by radical prostatectomy. Anticancer Res. Nov.-Dec. 2005;25(6C):4435-8.

Kepp, O., et al., Consensus guidelines for the detection of immunogenic cell death. Oncoimmunology. Dec. 13, 2014;3(9):e955691.

Kirby, M., et al. Characterising the castration-resistant prostate cancer population: a systematic review. Int J Clin Pract. Nov. 2011;65(11):1180-92.

Kwon, E.D., et al., Ipilimumab versus placebo after radiotherapy in patients with metastatic castration-resistant prostate cancer that had progressed after docetaxel chemotherapy (CA184-043): a multicentre, randomised, double-blind, phase 3 trial. Lancet Oncol. Jun. 2014;15(7):700-12.

Lee, S.O., et al., Interleukin-6 protects LNCaP cells from apoptosis induced by androgen deprivation through the Stat3 pathway. Prostate. Aug. 1, 2004;60(3):178-86.

Li, C.W., et al., Glycosylation and stabilization of programmed death ligand-1 suppresses T-cell activity. Nat Commun. Aug. 30, 2016;7:12632.

Liu, C., et al., Inhibition of constitutively active Stat3 reverses enzalutamide resistance in LNCaP derivative prostate cancer cells. Prostate. Feb. 2014;74(2):201-9.

Liu, W., et al., Genetic markers associated with early cancer-specific mortality following prostatectomy. Cancer. Jul. 1, 2013;119(13):2405-12.

Loeffler, M., et al., IL-18-producing *Salmonella* inhibit tumor growth. Cancer Gene Ther. Dec. 2008; 15(12)787-94.

Loeffler, M., et al., *Salmonella typhimurium* engineered to produce CCL21 inhibit tumor growth. Cancer Immunol Immunother. May 2009;58(5):769-75.

Maloy. Experimental Techniques in Bacterial Genetics. 1990. Jones and Bartlett. TOC Only.

Marx, C.J., et al. Development of an insertional expression vector system for Methylobacterium extorquens AM1 and generation of null mutants lacking mtdA and/or fch. Microbiology. Jan. 2004;150(Pt 1):9-19.

Melero, I., et al., Evolving synergistic combinations of targeted immunotherapies to combat cancer. Nat Rev Cancer. Aug. 2015;15(8):457-72.

Miller, A Short Course in Bacterial Genetics. Cold Spring Harbor Laboratory 1992.

Miller, Experiments in Molecular Genetics. Cold Spring Harbor Laboratory, 1972.

Morales, A., D. et al. Intracavitary Bacillus Calmette-Guerin in the treatment of superficial bladder tumors. J Urol. Feb. 2017;197(2S):S142-S145.

Muranski, P., et al., Th17 cells are long lived and retain a stem celllike molecular signature. Immunity. Dec. 23, 2011;35(6):972-85.

Murray, L., et al., Second primary cancers after radiation for prostate cancer: a systematic review of the clinical data and impact of treatment technique. Radiother Oncol. Feb. 2014;110(2):213-28.

Nupponen, N.N., et al., Genetic alterations in hormone-refractory recurrent prostate carcinomas. Am J Pathol. Jul. 1998; 153(1):141-8.

Ott, P.A., et al., Inhibition of Immune Checkpoints and Vascular Endothelial Growth Factor as Combination Therapy for Metastatic Melanoma: An Overview of Rationale, Preclinical Evidence, and Initial Clinical Data. Front Oncol. Sep. 22, 2015;5:202.

Parker, C., et al., Alpha emitter radium-223 and survival in metastatic prostate cancer. N Engl J Med. Jul. 18, 2013;369(3):213-23.

Quick, M.L., et al., Th1-Th17 cells contribute to the development of uropathogenic *Escherichia coli*-induced chronic pelvic pain. PLoS One. 2013;8(4):e60987.

Rathkopf, D.E., et al., Updated Interim Efficacy Analysis and Longterm Safety of Abiraterone Acetate in Metastatic Castration-resistant Prostate Cancer Patients Without Prior Chemotherapy (COU-AA-302). Eur Urol. Nov. 2014;66(5):815-25.

Robert, C., et al., Ipilimumab plus dacarbazine for previously untreated metastatic melanoma. N Engl J Med. Jun. 30, 2011;364(26):2517-26.

Roberts, N.J., et al., Intratumoral injection of Clostridium novyi-NT spores induces antitumor responses. Sci Transl Med. Aug. 13, 2014;6(249):249ra111.

Robinson, D., et al., Integrative clinical genomics of advanced prostate cancer. Cell. Jul. 16, 2015;162(2):454.

Rudick, C.N., et al., Uropathogenic *Escherichia coli* induces chronic pelvic pain. Infect Immun. Feb. 2011;79(2):628-35.

Runowicz, C.D., et al., American Cancer Society/American Society of Clinical Oncology Breast Cancer Survivorship Care Guideline. J Clin Oncol. Feb. 20, 2016;34(6):611-35.

(56) References Cited

OTHER PUBLICATIONS

Sambrook, J., et al., Molecular Cloning: A Laboratory Manual, 2nd ed.; Cold Spring Harbor Laboratory: Cold Spring Harbor, N.Y., (1989).
Scher, H.I., et al., Increased survival with enzalutamide in prostate cancer after chemotherapy. N Engl J Med. Sep. 27, 2012;367(13):1187-97.
Scott, et al., Plasmid 50(I):74-79 (2003).
Sfanos, K.S., et al., Human prostate-infiltrating CD8+ T lymphocytes are oligoclonal and PD-1+. Prostate. Nov. 1, 2009;69(15):1694-703.
Sfanos, K.S., et al., Phenotypic analysis of prostate-infiltrating lymphocytes reveals TH17 and Treg skewing. Clin Cancer Res. Jun. 1, 2008;14(11):3254-61.
Shahabi, V., et al., Development of a Listeria monocytogenes based vaccine against prostate cancer. Cancer Immunol Immunother. Sep. 2008;57(9):1301-13.
Shariat, S.F., et al., Plasma levels of interleukin-6 and its soluble receptor are associated with prostate cancer progression and metastasis. Urology. Dec. 2001;58(6):1008-15.
Silhavy, T.J., et al. Experiments with Gene Fusions; Cold Spring Harbor Laboratory: Cold Spring Harbor, N.Y., (1984).
Simons, B.W., et al., A human prostatic bacterial isolate alters the prostatic microenvironment and accelerates prostate cancer progression. J Pathol. Feb. 2015;235(3):478-89.
Topalian, S. L. et al. Safety, activity, and immune correlates of anti-PD-1 antibody in cancer. N Engl J Med. Jun. 28, 2012;366(26):2443-54.
Topalian, S. L. et al. Survival, durable tumor remission, and long-term safety in patients with advanced melanoma receiving nivolumab. J Clin Oncol. Apr. 1, 2014;32(10):1020-30.
Tumeh, P.C., et al., PD-1 blockade induces responses by inhibiting adaptive immune resistance. Nature. Nov. 27, 2014;515(7528):568-71.
Valsecchi, M.E., Combined Nivolumab and Ipilimumab or Monotherapy in Untreated Melanoma. N Engl J Med. Sep. 24, 2015;373(13):1270.
Vesalainen, S., et al., Histological grade, perineural infiltration, tumour-infiltrating lymphocytes and apoptosis as determinants of long-term prognosis in prostatic adenocarcinoma. Eur J Cancer. 1994;30A(12):1797-803.
Wallace, J., Humane endpoints and cancer research. ILAR J. 2000;41(2):87-93.
Watson, P.A., et al., Context-dependent hormone-refractory progression revealed through characterization of a novel murine prostate cancer cell line. Cancer Res. Dec. 15, 2005;65(24):11565-71.
Wolchok, J. D et al. Nivolumab plus ipilimumab in advanced melanoma. N Engl J Med. Jul. 11, 2013;369(2):122-33.
Wu, C.T., et al., The role of IL-6 in the radiation response of prostate cancer. Radiat Oncol. Jun. 27, 2013;8:159.
Xu, K., et al., Regulation of androgen receptor transcriptional activity and specificity by RNF6-induced ubiquitination. Cancer Cell. Apr. 7, 2009;15(4):270-82.
Yasuda, S., et al., Simultaneous blockade of programmed death 1 and vascular endothelial growth factor receptor 2 (VEGFR2) induces synergistic anti-tumour effect in vivo. Clin Exp Immunol. Jun. 2013;172(3):500-6.
Zhao, J., et al., Androgen deprivation therapy for prostate cancer is associated with cardiovascular morbidity and mortality: a meta-analysis of population-based observational studies. PLoS One. Sep. 29, 2014;9(9):e107516.
Zheng, J.H., et al., Two-step enhanced cancer immunotherapy with engineered *Salmonella typhimurium* secreting heterologous flagellin. Sci Transl Med. Feb. 8, 2017;9(376).

* cited by examiner

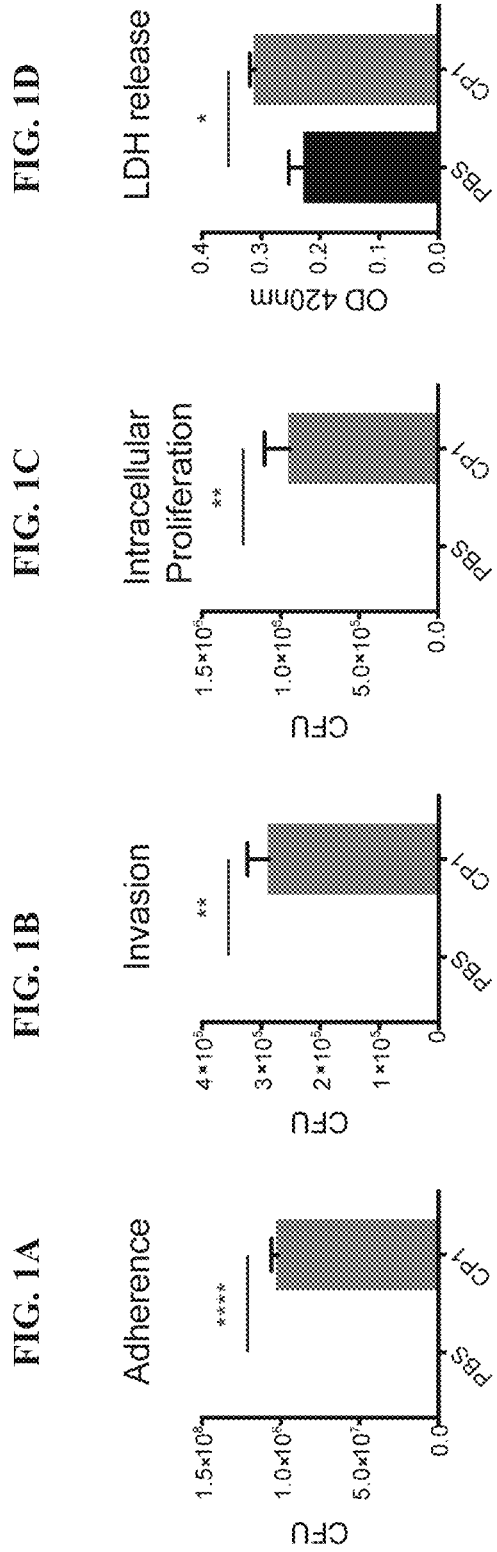

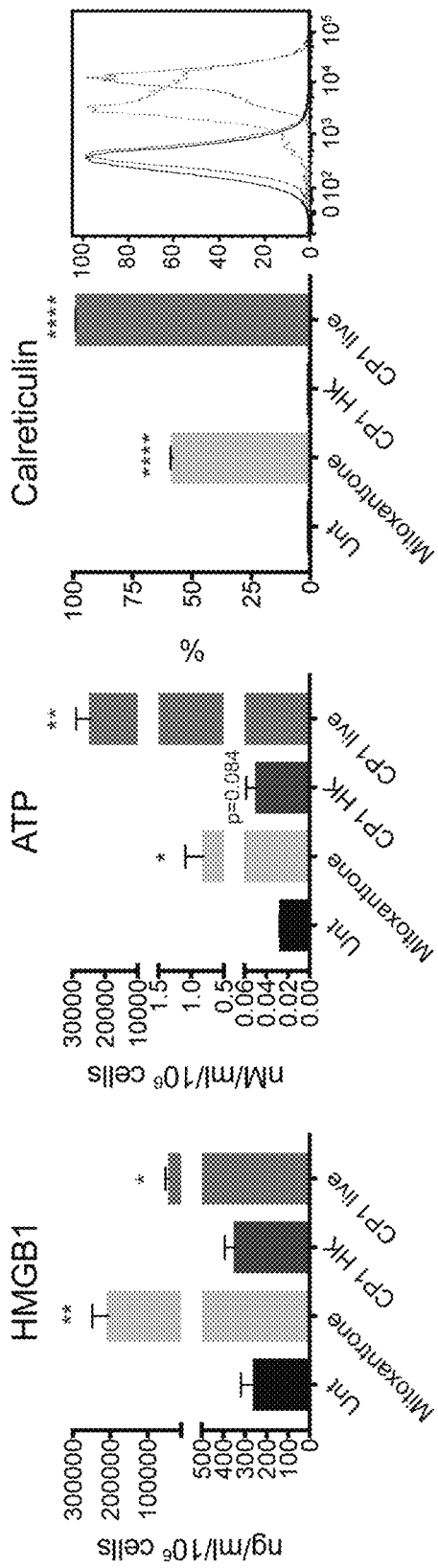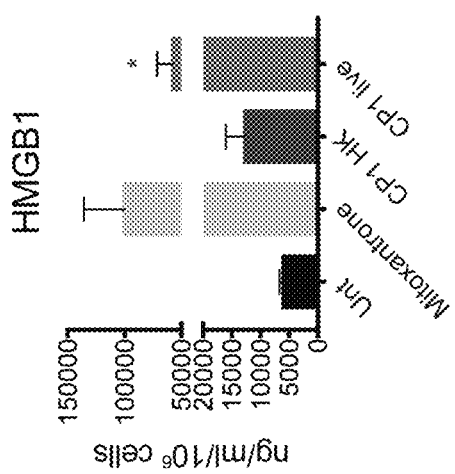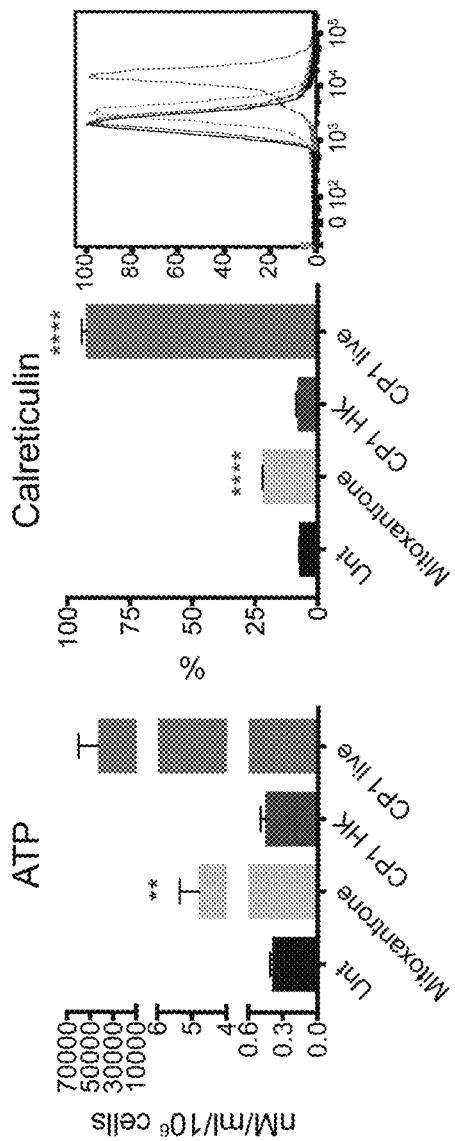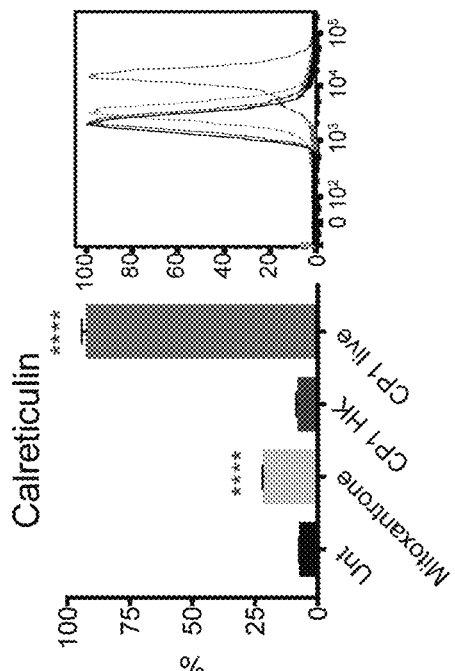

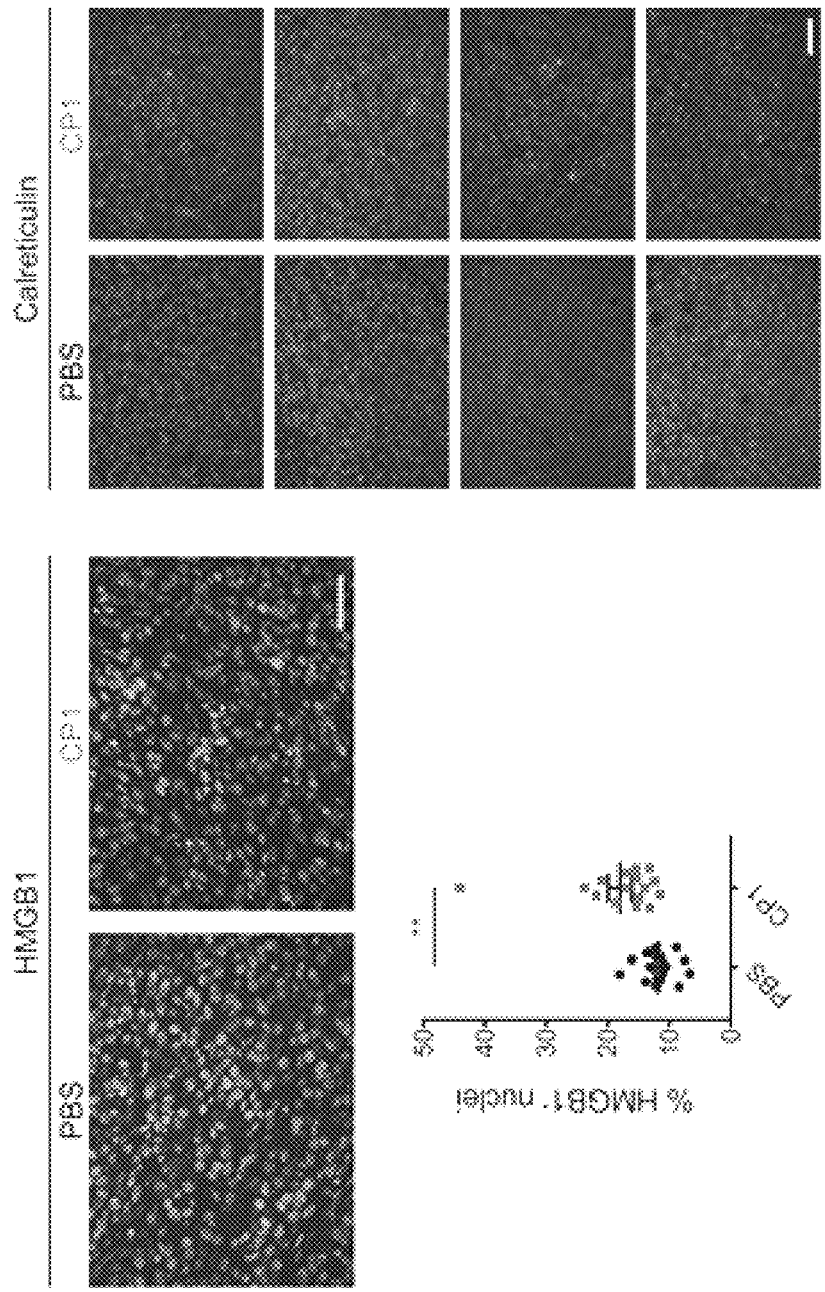

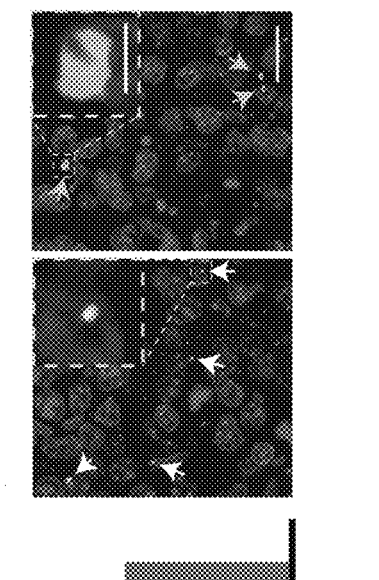
FIG. 2C
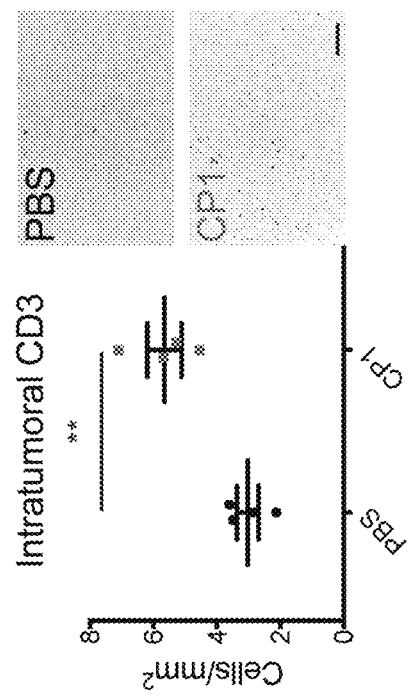
FIG. 2B
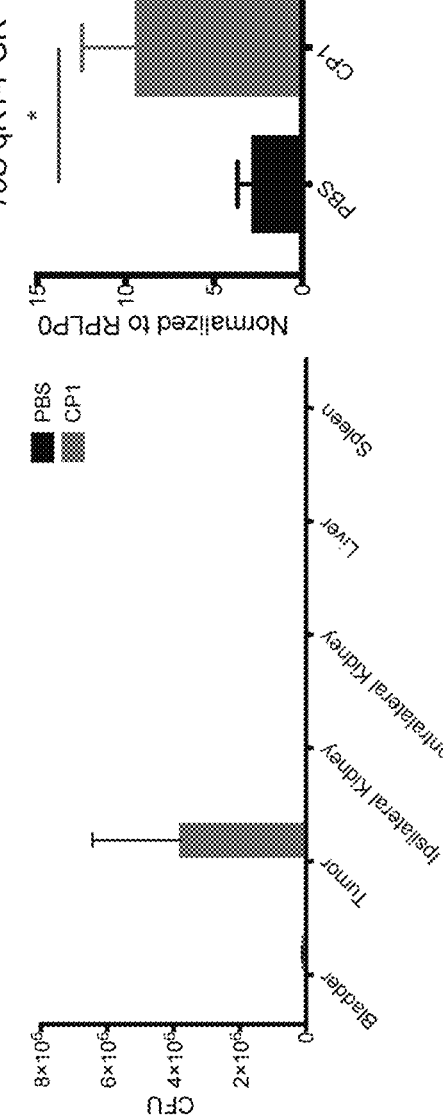
FIG. 2A
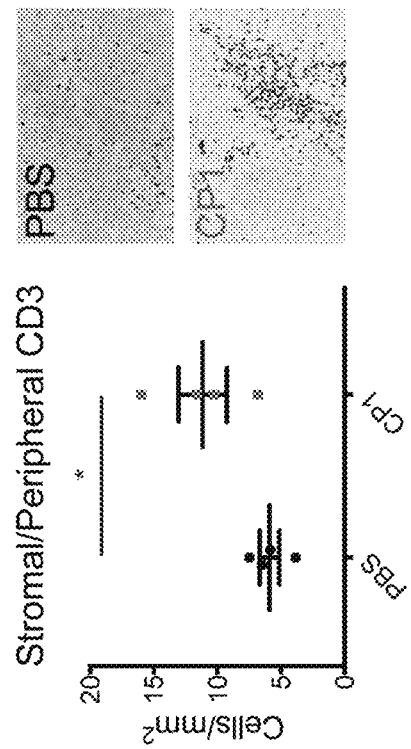
FIG. 2E
FIG. 2D

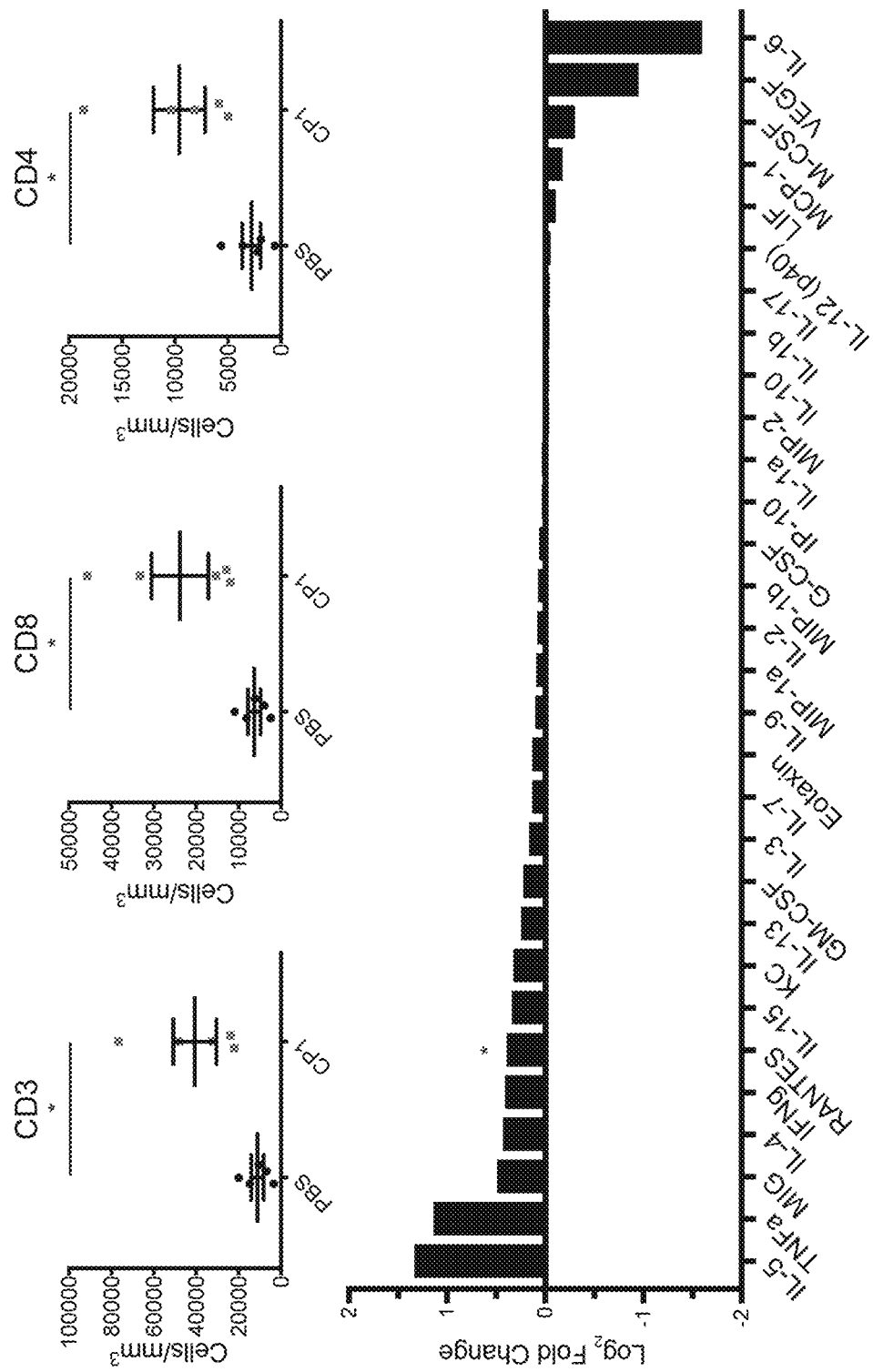
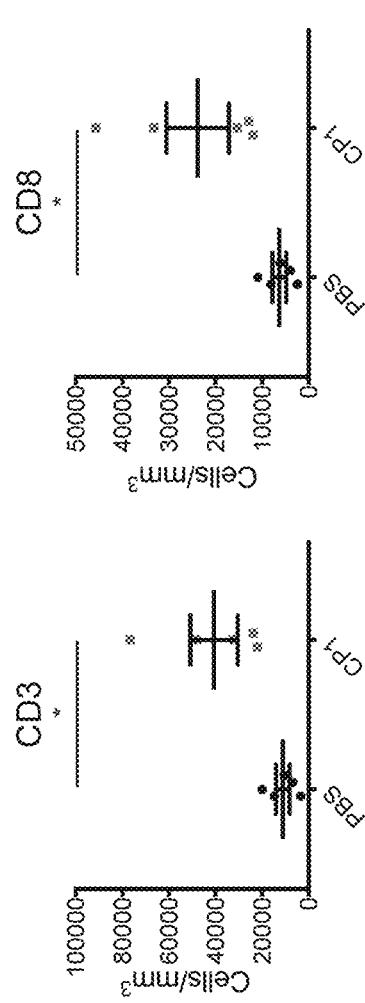
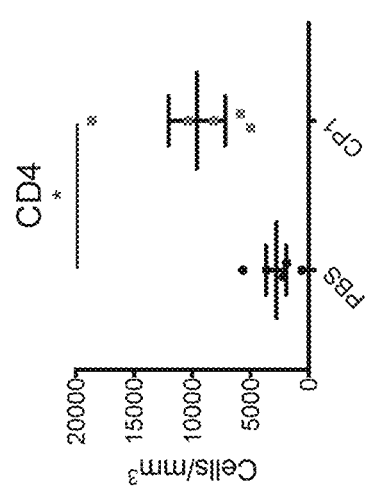
FIG. 2F  FIG. 2G  FIG. 2H
FIG. 2I

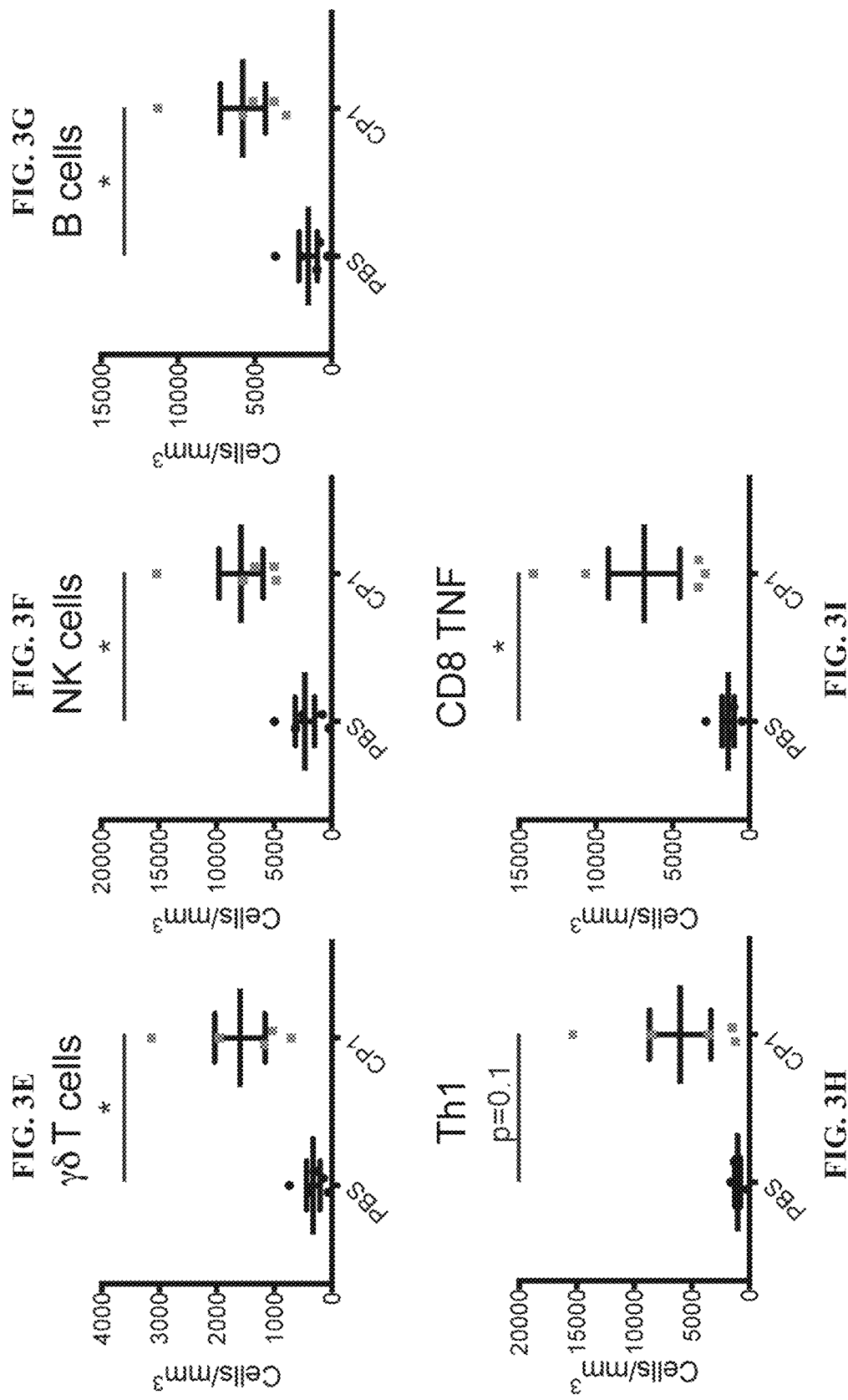

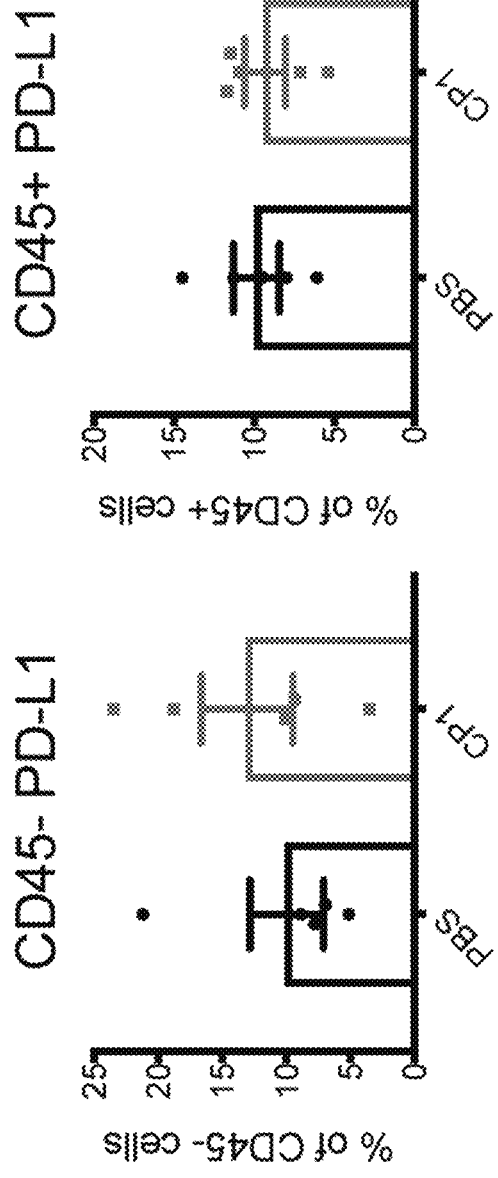
FIG. 3M
FIG. 3N
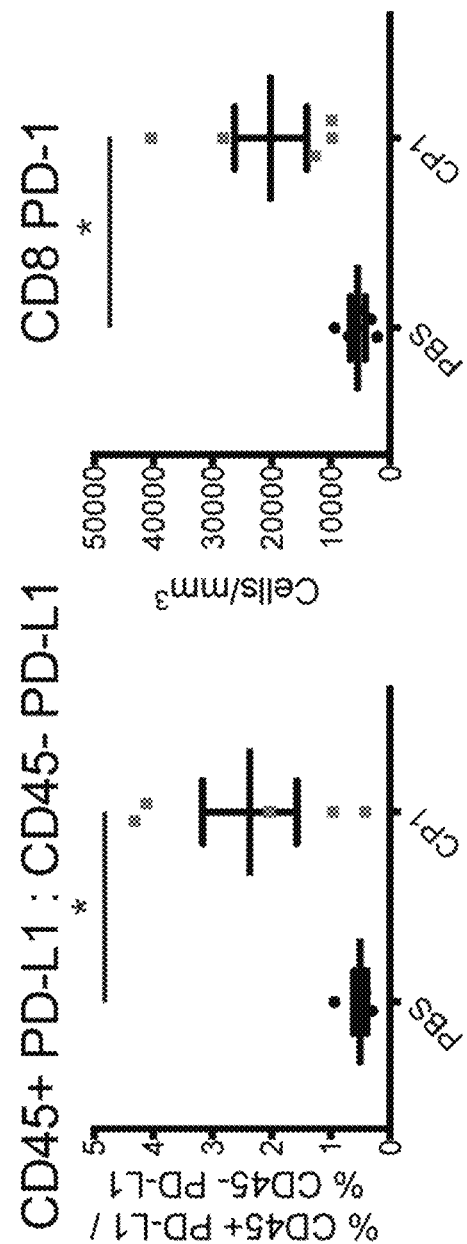
FIG. 3O
FIG. 3P

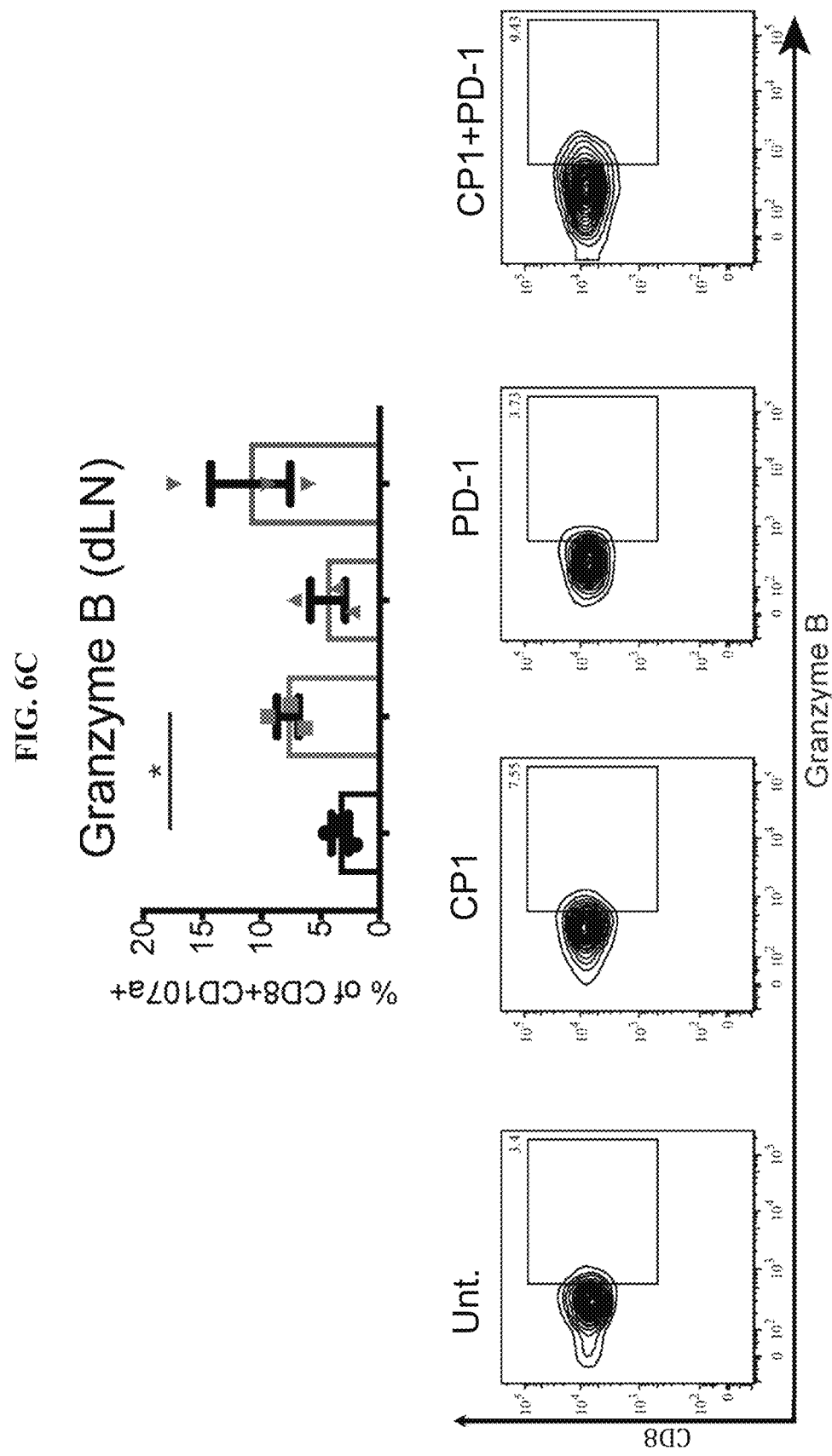

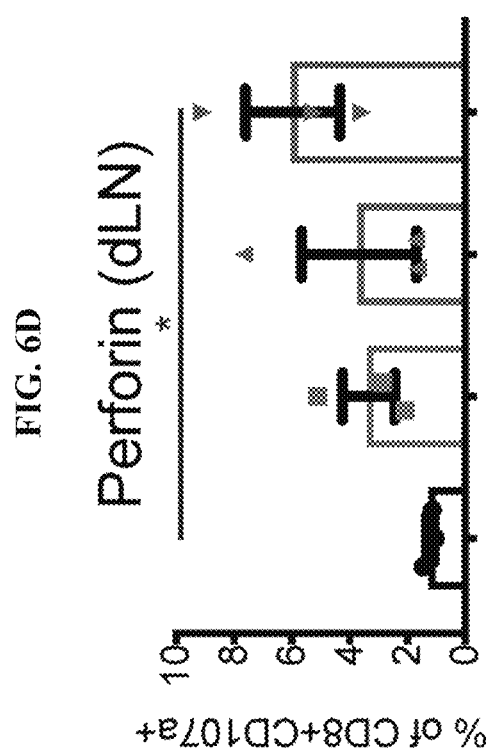

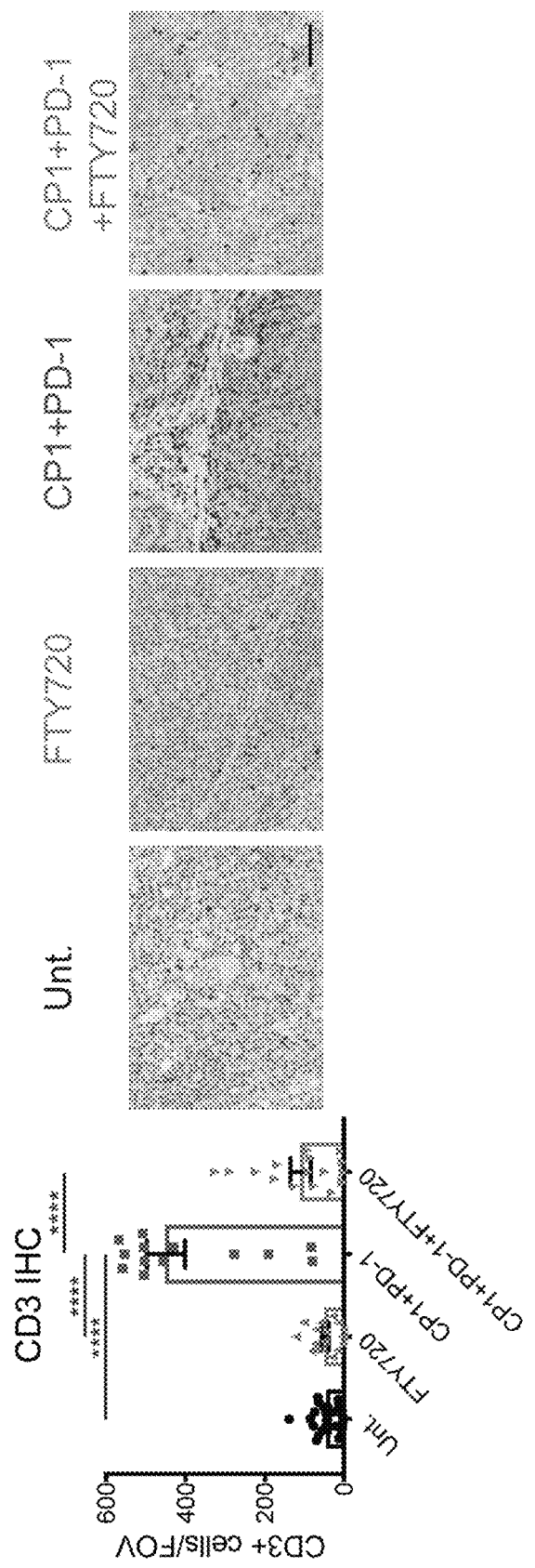

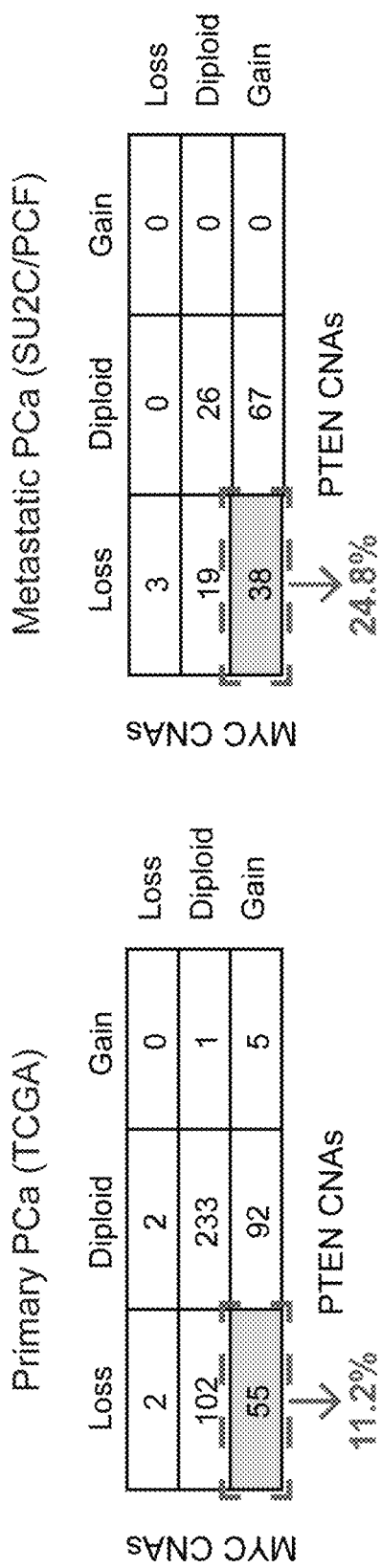
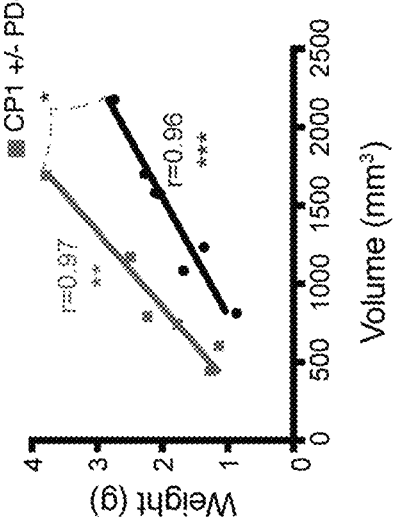
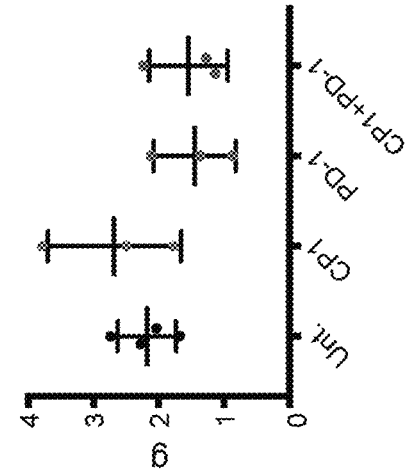
FIG. 13A
FIG. 13B
FIG. 13C

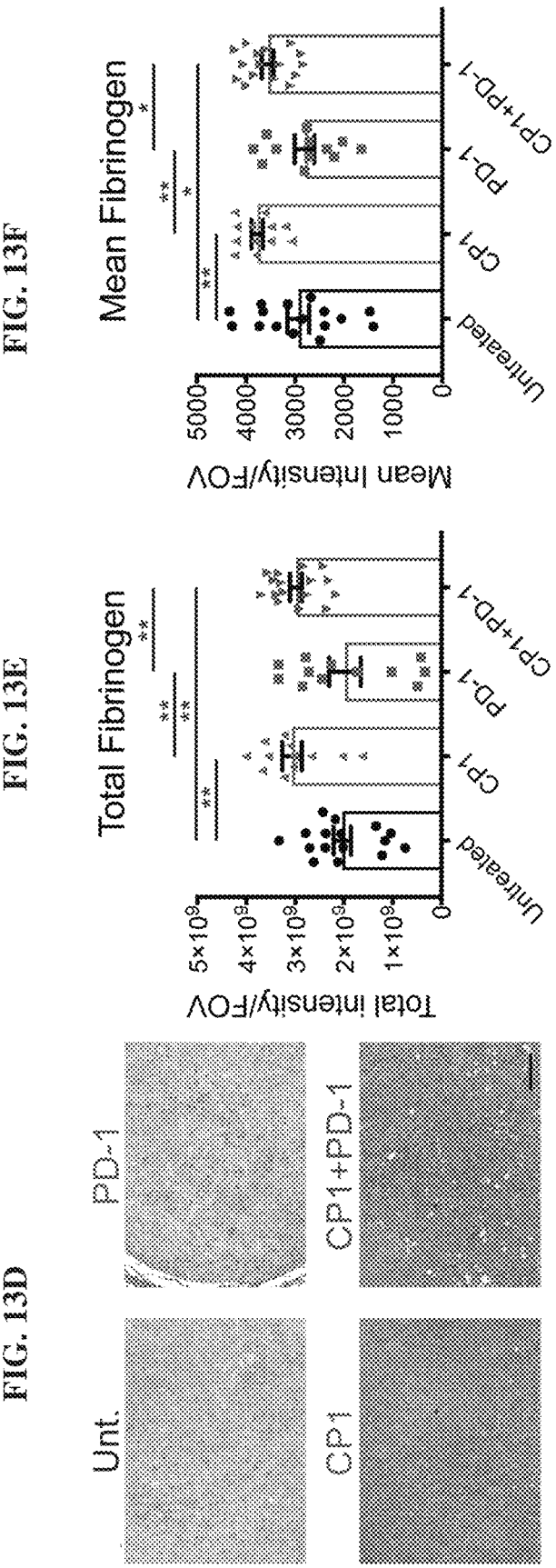

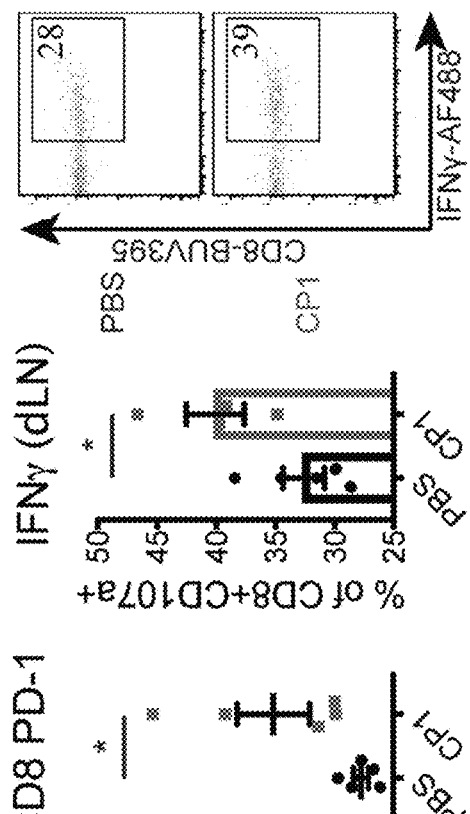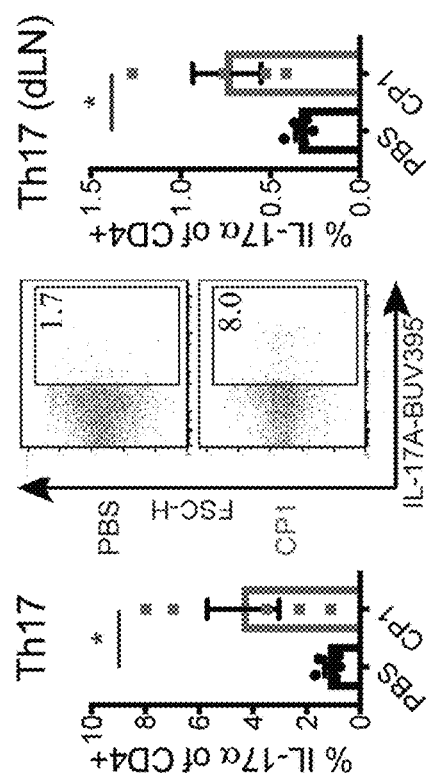

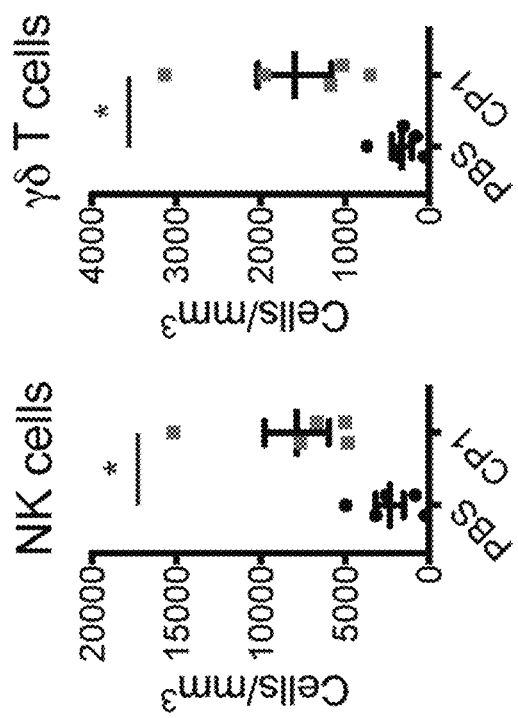
FIG. 14L
FIG. 14M
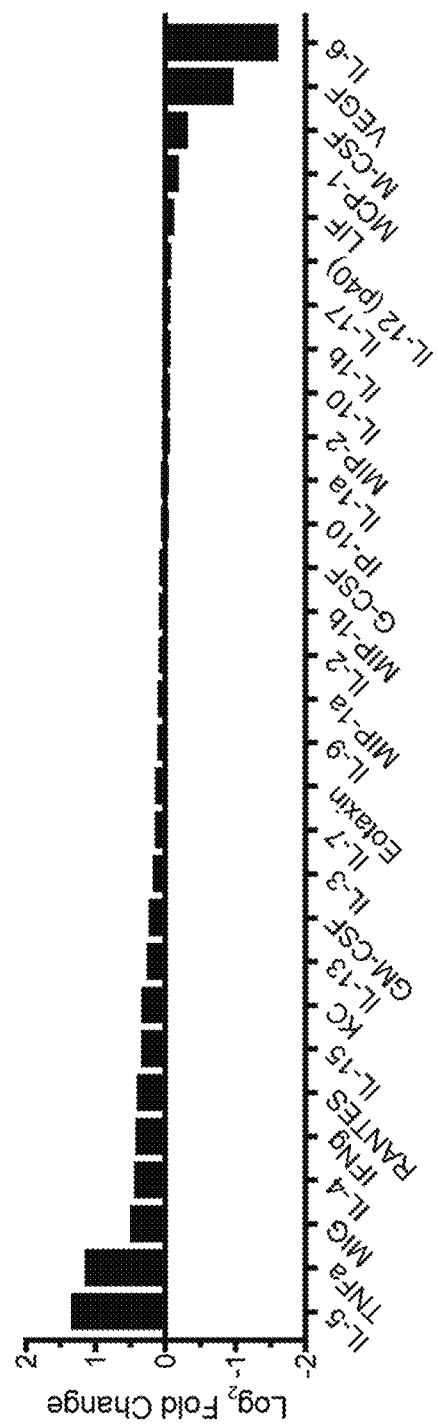
FIG. 14N

IMMUNOSTIMULATORY BACTERIA FOR THE TREATMENT OF CANCER

CROSS-REFERENCE TO RELATED APPLICATIONS

The present invention claims the priority benefit of U.S. Provisional Patent Application 62/539,843, filed Aug. 1, 2017, which is incorporated by reference in its entirety.

STATEMENT REGARDING FEDERAL FUNDING

This invention was made with government support under R01 DK094898 awarded by the National Institutes of Health. The government has certain rights in the invention.

FIELD

Provided herein are composition and methods for the treatment of cancer by the administration of uropathogenic bacteria. In particular, CP1 *E. coli* (ATTC Patent Deposit #PTA-127513) is administered for the treatment of prostate cancer.

BACKGROUND

Immune checkpoint inhibitors have shown great promise in recent years, with anti-CTLA-4 and anti-PD-1/PD-L1 blocking antibodies gaining FDA approval in multiple cancer types. The efficacy of these immunotherapies and their ability to overcome tumor-driven immunosuppression is dependent on the level of tumor infiltrating lymphocytes (TILs) at the time of and during the course of administration (Ref 1; incorporated by reference in its entirety). Tumor types with the strongest clinical responses to these antibodies have been those with the highest rates of mutagenicity, and therefore probable immunogenicity (Refs. 2, 3; incorporated by reference in their entireties). Prostate cancer, however, is not one of the most mutagenic tumors, and, to date, these immune checkpoint inhibitors have failed, with ipilimumab (Ref 4, 5; incorporated by reference in their entireties) and nivolumab (Ref. 6; incorporated by reference in its entirety) monotherapies showing no improvement in overall survival (OS) in patients with castration-resistant prostate cancer (CRPC). Failure of PD-1 blockade, despite many prostate tumors showing high PD-L1 levels (Ref 7; incorporated by reference in its entirety) and TILs displaying high PD-1 positivity (Refs. 8, 9; incorporated by reference in their entireties), indicates that low level of TILs and innate immunogenicity are responsible.

The field has begun to focus on combination immunotherapies to optimize efficacy. PD-1/PD-L1 and CTLA-4 blockade, specifically, have been combined with each other (Ref. 10; incorporated by reference in its entirety), adoptive T cell therapies (Ref. 11; incorporated by reference in its entirety), chemotherapies (Ref. 12; incorporated by reference in its entirety), radiation (Ref. 13; incorporated by reference in its entirety), and anti-angiogenic therapies (Ref. 11; incorporated by reference in its entirety), among others. The goal of these combinations is to synergistically enhance the major mechanisms of action of a successful immunotherapy. These include increasing TILs while decreasing immunosuppressive cell types in the tumor microenvironment, optimizing and increasing antigen-presenting cells (APCs), and increasing immunogenic cell death (ICD)-induced tumor immunogenicity (Ref. 14; incorporated by reference in its entirety).

SUMMARY

Provided herein are composition and methods for the treatment of cancer by the administration of uropathogenic bacteria (e.g., with or without genetic modification). In particular, CP1 *E. coli* (ATTC Patent Deposit #PTA-127513) is administered for the treatment of prostate cancer.

In some embodiments, provided herein are methods of treating cancer in a subject comprising administering uropathogenic bacteria capable of inducing T-cell inflammatory response in human or animal tissue. In some embodiments, the bacteria are capable of invading, proliferating, and/or colonizing human and/or animal cells and/or tissues. In some embodiments, the cancer is prostate cancer and the uropathogenic bacteria are capable of invading, proliferating, and/or colonizing prostate epithelial cells and/or prostatic tissues. In some embodiments, administering the uropathogenic bacteria results in increased production of biomarkers of inflammation. In some embodiments, the biomarkers of inflammation are selected from the group consisting of TNFα, and IFNγ, IL-12, and CXCL9. In some embodiments, the uropathogenic bacteria are an *Escherichia coli* (*E. coli*) bacteria. In some embodiments, the uropathogenic bacteria are *E. coli*, strain CP1 (ATTC Patent Deposit #PTA-127513). In some embodiments, the uropathogenic bacteria are genetically-modified to express one or more tumor-associated antigens (TAAs: prostate stem cell antigen (PSCA), prostate-specific antigen (PSA), and/or antigenic variants or fragments thereof) or other molecules. In some embodiments, the uropathogenic bacteria are co-administered with one or more additional cancer therapies. In some embodiments, the additional cancer therapies are selected from the group consisting of chemotherapy, radiation, surgery, and immunotherapy. In some embodiments, the uropathogenic bacteria are co-administered with one or more additional immunotherapy agents.

In some embodiments, the uropathogenic bacteria are co-administered with a checkpoint inhibitor. In some embodiments, the immune checkpoint inhibitor is a small molecule, peptide, protein, polypeptide, antibody, or antigen binding fragment that binds to an immune checkpoint protein. In some embodiments, the immune checkpoint protein is CTLA4, PD-1, PD-L1, PD-L2, A2AR, B7-H3, B7-H4, BTLA, KIR, LAG3, TIM-3 or VISTA. In some embodiments, the immune checkpoint inhibitor is nivolumab, pembrolizumab, pidilizumab, AMP-224, AMP-514, STI-A1110, TSR-042, RG-7446, BMS-936559, BMS-936558, MK-3475, CT-011, MPDL3280A, MEDI-4736, MSB-0020718C, AUR-012 and STI-A1010. In some embodiments, CP1 bacteria are co-administered with rituximab or other anti-B cell therapies. In some embodiments, CP1 bacteria are co-administered with anti-CSF1R and anti-macrophage and anti-myeloid derives suppressor cell therapies including but not limited to GW2580. In some embodiments, CP1 bacteria are co-administered with agents targeting CXCL2/MIP-2, CD40 agonists, or IRE1/XBP1 inhibitors. In some embodiments, CP1 bacteria are co-administered with zoledronate or similar bisphosphonates.

In some embodiments, *Escherichia coli* (*E. coli*), strain CP1 bacteria, is able to be genetically modified, wherein the bacteria expresses one or more tumor-associated antigens, cytokines, chemokines, or other cytolytic or adjuvant adjents or immune modulating molecules. In some embodiments, the bacteria is capable of inducing T-cell inflammatory response in human or animal tissue. In some embodiments, the bacteria are capable of invading, proliferating, and/or colonizing prostate epithelial cells and/or prostatic tissues. In some embodiments, the bacteria are genetically-modified to display one or more tumor-associated antigens (TAAs). In some embodiments, the bacteria are genetically-modified to display prostate stem cell antigen (PSCA), prostate-specific antigen (PSA), and/or antigenic variants or fragments thereof.

BRIEF DESCRIPTION OF THE DRAWINGS

FIGS. 1A-M. CP1 adheres and invades prostate cancer cells, induces tumor ICD and pro-inflammatory cytokine/chemokine profile while decreasing immunosuppressive cytokines. A-C) Gentamicin protection assay with CP1 in vitro, with CFUs quantified for bacterial A) adherence to, B) invasion in, C) and intracellular proliferation in Myc-CaP cells in vitro, performed in triplicates. D) Supernatant LDH levels from exposure of Myc-CaP cells to CP1, as a measure of cell death, performed in triplicates. Immunogenic cell death in E-G) Myc-CaP and H-J) LNCaP cells in vitro after exposure to mitoxantrone, heat killed (HK) CP1, or live CP1. E,H) HMGB1 was measured in supernatant by ELISA, F,I) ATP by bioluminescence assay, and G,J) calreticulin by flow cytometry, performed in triplicates. K) Multiplex cytokine and chemokine levels from Myc-CaP in vitro, represented as the log 2 fold change with and without CP1 exposure, each sample analyzed in technical duplicates. ICD was assessed in vivo by (L) HMGB1 or (M) calreticulin IF of prostate tumor tissue 9 days after intra-urethral CP1 administration, with representative images (each calreticulin image representative of a different tumor, green=HMGB1 or calreticulin, scale bar, 50 m). Mice n=4/group, HMGB1 quantified with quadruplicate FOVs/tumor.

FIGS. 2A-I. CP1 specifically colonizes prostate tumor tissue, increases TIL density, and incudes pro-inflammatory cytokine/chemokine profile while decreasing immunosuppressive cytokines. A) Colonization levels in the prostate tumor, bladder, ipsilateral and contralateral (relative to the site of the tumor) kidneys, liver, and spleen. B) 16S qRT-PCR of tumor RNA with and without CP1 administration. C) E. coli IF of tumor tissue (green=intracellular, yellow=extracellular), scale bar=20 μm, magnified scale bar=4 μm. D) Stromal/peripheral and E) intratumoral CD3 IHC with representative images (scale bar=100 μm). Flow cytometry, normalized to tumor volume, of F) CD3, G) CD8, and H) CD4 T cells. I) Multiplex cytokine and chemokine levels from Myc-CaP tumors, represented as the log 2 fold change with and without CP1 administration, each sample analyzed in technical duplicates.

FIGS. 6A-G. CP1 increases TIL density and CD8 cytotoxic activity, decreases Tregs, and incudes pro-inflammatory cytokine/chemokine profile while decreasing immunosuppressive cytokines. A) CD3 TIL density, as determined by IHC, quadruplicate field of views (FOVs) scored per sample, with representative images, scale bar=100 m. Flow cytometry analysis of B) IFNγ, C) granzyme B, and D) perforin expression from CD8+CD107a+ dLN cells. Flow cytometry analysis of E) PD-1 expression on CD8 TILs and F) intratumoral Tregs. G) Multiplex cytokine and chemokine levels from PTEN OK Myc-CaP tumors, represented as the log 2 fold change with and without CP1 administration, each sample analyzed in technical duplicates.

FIGS. 7A-F. Complete efficacy of CP1 immunotherapy is dependent upon its ability to increase TIL density. A) Tumor volume and B) gross representative images from untreated (unt.), FTY720, CP1 and anti-PD-1, and CP1 and anti-PD-1 and FTY720 administered mice. C) CD3, D) CD4, and E) CD8 TIL densities, as determined by flow cytometry, normalized to tumor volume. F) CD3 TIL density, as determined by IHC, with quadruplicate field of views (FOVs) scored per sample.

FIGS. 13A-F. The Myc-CaP PTEN KO model in representative of advanced prostate cancer, in which CP1 increases tumor weight through increased fibrinous exudate. A) Tables of the number of samples with MYC and PTEN copy number diploid, loss, or gain in the TCGA and SU2C/PCF databases, with percentages indication the percent of samples with concurrent MYC gain and PTEN loss. B) PTEN KO tumor weights of unt., CP1, anti-PD-1, or combination CP1 and anti-PD-1 treated mice. C) PTEN KO tumor densities of CP1 or PBS (with or without anti-PD-1) treated mice, with their respective correlation coefficients and further analysis of the density slopes. IHC D) images and quantification of E) total and F) mean fibrinogen intensity per field of view (FOV), with quadruplicate FOVs scored per sample.

DEFINITIONS

Figure 1K:
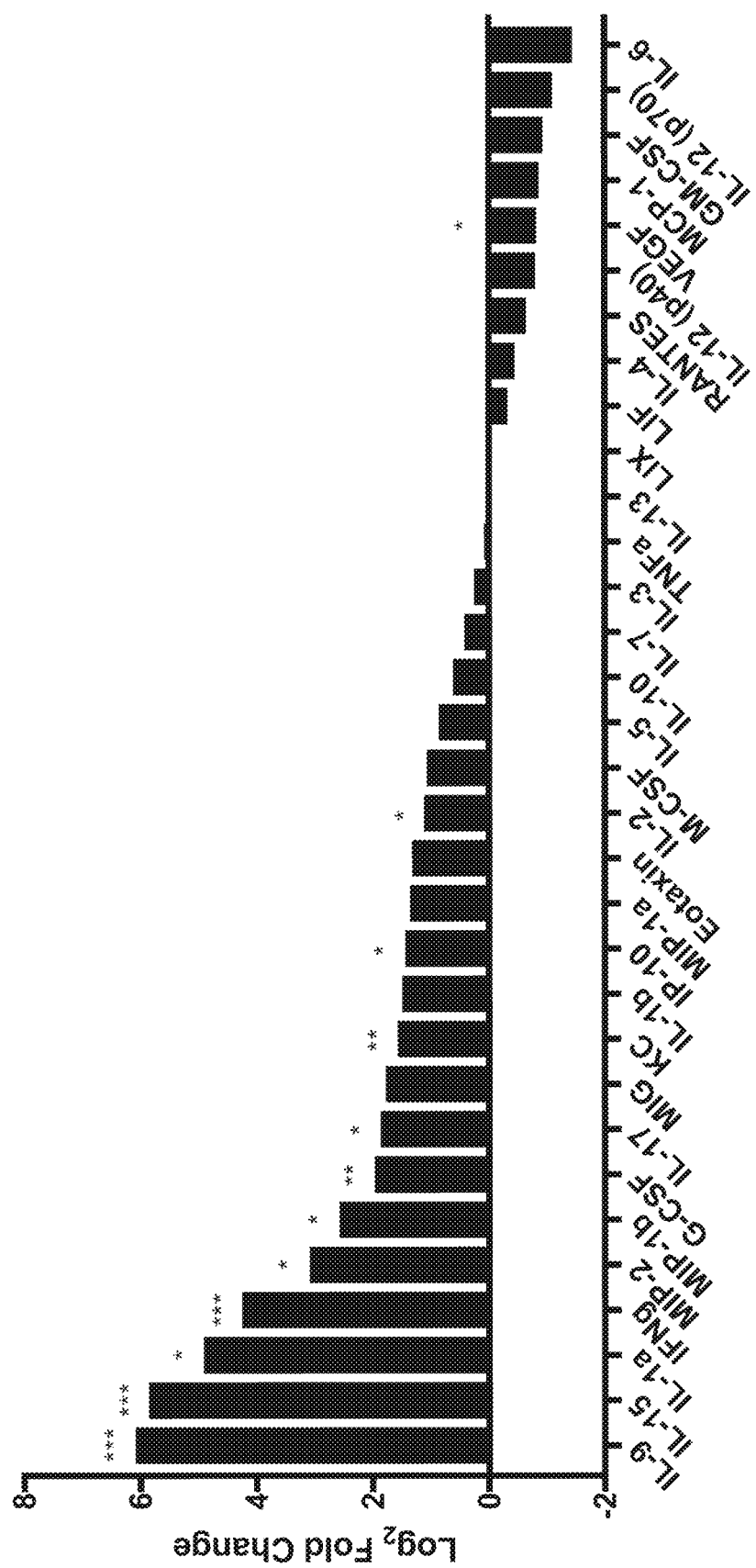

The terminology used herein is for the purpose of describing the particular embodiments only, and is not intended to limit the scope of the embodiments described herein. Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a tumor-associated antigen" is a reference to one or more tumor-associated antigens and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "pathogenic" refers to a microbe capable of infecting and/or colonizing a human or animal host and producing disease and/or infection-related symptoms.

As used herein, the term "urinary tract" refers to any portion of the renal system, such as the kidneys, ureters, bladder, and the urethra.

As used herein, the term "uropathogenic" refers to a microbe capable of infecting and/or colonizing all or a portion of the urinary tract of a subject and producing disease and/or infection-related symptoms. Urinary tract infections (UTIs) caused by infection of the urinary tract by, for example, *E. coli*, is a common condition caused by infection by uropathogenic bacteria.

As used herein, the term "genetically modified" denotes a cell or organism (e.g., bacterial cell) that either (i) comprises a heterologous nucleotide sequence and/or expresses/displays a non-native protein/peptide product, and/or (ii) lacks a portion of nucleotide sequence and/or an expression product that is native to the unmodified cell or organism. A genetically-modified cell may exhibit characteristics that are distinct from the unmodified cell. For example, genetically-modified uropathogenic bacteria may lack the uropathogenicity of the unmodified bacteria.

As used herein, the term "pharmaceutical agent" refers to a compound, macromolecule, or other chemical/non-biological entity that is administered to a subject to elicit a desired biological response. A pharmaceutical agent may be a "drug" or another entity which is biologically active in a human being or other mammal, locally and/or systemically. Examples of drugs are disclosed in the Merck Index and the Physicians' Desk Reference, the entire disclosures of which are incorporated by reference herein for all purposes.

As used herein, the term "co-administration" refers to the administration of at least two agents (e.g., uropathogenic bacteria and a second cancer therapy) or therapies to a subject. In some embodiments, the co-administration of two or more agents/therapies is concurrent. In other embodiments, the co-administration of two or more agents/therapies is sequential (e.g., a first agent/therapy is administered prior to a second agent/therapy).

As used herein, the terms "antibiotic" and "antibacterial agent" refer to a chemical agent which is active against bacteria. In common usage, an antibiotic is a substance or compound (also called chemotherapeutic agent) that kills or inhibits the growth of bacteria. Anti-bacterial antibiotics can be categorized based on their target specificity: "narrow-spectrum" antibiotics target particular types of bacteria, such as Gram-negative or Gram-positive bacteria, while broad-spectrum antibiotics affect a wide range of bacteria. Antibiotics which target the bacterial cell wall (e.g., penicillins, cephalosporins, cephems), or cell membrane (e.g., polymixins), or interfere with essential bacterial enzymes (e.g., quinolones, sulfonamides) usually are bactericidal in nature. Those which target protein synthesis such as the aminoglycosides, macrolides and tetracyclines are usually bacteriostatic. Three newer classes of antibiotics include: cyclic lipopeptides (e.g., daptomycin), glycylcyclines (e.g., tigecycline), and oxazolidinones (e.g., linezolid). Tigecycline is a broad-spectrum antibiotic, while the two others are useful for Gram-positive infections.

As used herein, the term "pharmaceutical formulation" refers to at least one pharmaceutical agent and/or microbial agent in combination with one or more additional components that assist in rendering the agent(s) suitable for achieving the desired effect upon administration to a subject. The pharmaceutical formulation may include one or more additives, for example pharmaceutically acceptable excipients, carriers, penetration enhancers, coatings, stabilizers, buffers or other materials physically associated with the pharmaceutical/microbial agent to enhance the administration, release (e.g., timing of release), deliverability, bioavailability, effectiveness, etc. of the dosage form. The formulation may be, for example, a liquid, a suspension, a solid, a nanoparticle, emulsion, micelle, ointment, gel, emulsion, coating, etc. A pharmaceutical formulation may contain a single agent or multiple agents.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition (e.g., cancer, solid tumor cancer, prostate cancer, etc.).

As used herein, an "immune response" refers to the action of a cell of the immune system (e.g., T lymphocytes, B lymphocytes, natural killer (NK) cells, macrophages, eosinophils, mast cells, dendritic cells, neutrophils, etc.) and soluble macromolecules produced by any of these cells or the liver (including Abs, cytokines, and complement) that results in selective targeting, binding to, damage to, destruction of, and/or elimination from a subject of invading pathogens, cells or tissues infected with pathogens, or cancerous or other abnormal cells.

As used herein, the term "immunotherapy" refers to the treatment or prevention of a disease or condition (e.g., cancer) by a method comprising inducing, enhancing, suppressing or otherwise modifying an immune response.

The term "effective dose" or "effective amount" refers to an amount of an agent (e.g., drug, bacterial agent, etc.), that results in the reduction of symptoms in a patient or results in a desired biological outcome. In certain embodiments, an effective dose or effective amount is sufficient to treat or reduce symptoms of a disease or condition.

As used herein, the term "antibody" refers to a whole antibody molecule or a fragment thereof (e.g., fragments such as Fab, Fab', F(ab')2, Fv, scFv, Fd, diabodies, and other antibody fragments that retain at least a portion of the variable region of an intact antibody; see, e.g., Hudson et al. (2003) Nat. Med. 9:129-134; herein incorporated by reference in its entirety), it may be a polyclonal or monoclonal antibody, a chimeric antibody, a humanized antibody, a human antibody, etc. A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, VH, and three constant regions, CH1, CH2, and CH3. The VH domain is at the amino-terminus of the heavy chain, and the CH3 domain is at the carboxy-terminus. In a native antibody, a light chain comprises a variable region, VL, and a constant region, CL. The variable region of the light chain is at the amino-terminus of the light chain. In a native antibody, the variable regions of each light/heavy chain pair typically form the antigen binding site. The constant regions are typically responsible for effector function.

DETAILED DESCRIPTION

Provided herein are composition and methods for the treatment of cancer by the administration of uropathogenic bacteria. In particular, genetically-modified CP1 *E. coli* (ATTC Patent Deposit #PTA-127513) is administered for the treatment of prostate cancer.

Prostate cancer is the most prevalent non-skin cancer in men and second only to lung cancer in estimated deaths (Ref. 34; incorporated by reference in its entirety). However, at all stages of disease, treatment options are not ideal. Surgery, radiation, and androgen deprivation therapy (ADT) are all associated with major systemic and urologic comorbidities (Refs. 35-37; incorporated by reference in their entireties). Additionally, after ADT, all patients eventually recur with CRPC, for which there is a median survival of 9-30 months (Refs. 38-40; incorporated by reference in their entireties) and no treatment confers more than a 5.2 month survival benefit (Refs. 41-47; incorporated by reference in their entireties).

Immune checkpoint inhibitors have thus far failed to demonstrate clinical benefit in prostate cancer, there are multiple reasons why immune-modulation remains a viable strategy.

Experiments were conducted during development of embodiments herein to isolate and characterize a clinical bacterial uropathogenic *Escherichia coli*, termed CP1 (ATTC Patent Deposit #PTA-127513), specifically from the expressed prostatic secretions of a patient with chronic prostatitis without concurrent cystitis. CP1 is able to adhere to, invade, and proliferate within prostate epithelial cells in vitro and colonize prostatic tissue for prolonged periods in vivo (Ref. 18; incorporated by reference in its entirety). CP1 induces a durable and prostate-specific local T cell-driven inflammatory response with infiltration of Th1/Th17 skewed T cells, among other cell types, as well as increased production of TNFα, and IFNγ, IL-12, and CXCL9 in the setting of cancer (Refs. 19-22; incorporated by reference in their entireties).

Experiments were conducted during development of embodiments herein to demonstrate that the unique innate prostate specificity and immunostimulatory properties of CP1 increase the efficacy of PD-1 blockade. Experiments were conducted in multiple clinically relevant and immunocompetent orthotopic models of different stages and genetic backgrounds of prostate cancer. CP1 represents a multifaceted immunotherapeutic approach, increasing tumor immunogenicity through ICD and pro-inflammatory cytokine production, increasing TILs, optimizing APCs, and decreasing angiogenic factors, in order to synergistically enhance the efficacy of anti-PD-1 immunotherapy.

In some embodiments, uropathogenic bacteria (e.g., CP1), without genetic modification, is used therapeutically and/or prophylactically to increase tumor immunogenicity.

In some embodiments, genetically-modified uropathogenic bacteria (e.g., CP1) is used therapeutically and/or prophylactically to increase tumor immunogenicity. In some embodiments, uropathogenic bacteria (e.g., CP1) are genetically modified to express and/or display one or more tumor-associated antigens (TAAs) or tumor-associated biomarkers. In some embodiments, TAAs or biomarkers are selected based on the cancer or tumor type to be treated by the bacteria. Exemplary TAAs or biomarkers include, but are not limited to: anaplastic lymphoma kinase (ALK and rearrangements thereof, particularly useful for treating non-small cell lung cancer and anaplastic large cell lymphoma), alpha-fetoprotein (AFP; particularly useful for treating liver cancer and germ cell tumors), beta-2-microglobulin (B2M; particularly useful for treating multiple myeloma, chronic lymphocytic leukemia, and some lymphomas), beta-human chorionic gonadotropin (beta-hCG; particularly useful for treating choriocarcinoma and germ cell tumors), BRCA1 and BRCA2 gene mutations (particularly useful for treating ovarian cancer), BCR-ABL fusion gene (particularly useful for treating chronic myeloid leukemia, acute lymphoblastic leukemia, and acute myelogenous leukemia), BRAF V600 mutations (particularly useful for treating cutaneous melanoma and colorectal cancer), c-kit/CD117 (particularly useful for treating gastrointestinal stromal tumor and mucosal melanoma), CA15-3/CA27.29 (particularly useful for treating breast cancer), CA19-9 (particularly useful for treating pancreatic cancer, gallbladder cancer, bile duct cancer, and gastric cancer), CA-125 (particularly useful for treating ovarian cancer), calcitonin (particularly useful for treating medullary thyroid cancer), carcinoembryonic antigen (CEA; particularly useful for treating colorectal cancer), CD20 (particularly useful for treating non-Hodgkin lymphoma), chromogranin A (CgA; particularly useful for treating neuroendocrine tumors), cytokeratin fragment 21-1 (particularly useful for treating lung cancer), EGFR (particularly useful for treating non-small cell lung cancer), estrogen receptor (ER)/progesterone receptor (PR) (particularly useful for treating breast cancer), fibrin/fibrinogen (particularly useful for treating bladder cancer), HE4 (particularly useful for treating ovarian cancer), HER2/neu (particularly useful for treating breast cancer, gastric cancer, and gastroesophageal junction adenocarcinoma), mutated KRAS (particularly useful for treating colorectal cancer and non-small cell lung cancer), lactate dehydrogenase (particularly useful for treating germ cell tumors, lymphoma, leukemia, melanoma, and neuroblastoma), neuron-specific enolase (NSE; particularly useful for treating small cell lung cancer and neuroblastoma), nuclear matrix protein 22 (particularly useful for treating bladder cancer), programmed death ligand 1 (PD-L1), prostate-specific antigen (PSA; particularly useful for treating prostate cancer), prostate stem cell antigen (PSCA; particularly useful for treating prostate cancer), thyroglobulin (particularly useful for treating thyroid cancer), urokinase plasminogen activator (uPA) and plasminogen activator inhibitor (PAI-1), etc.

In some embodiments, uropathogenic bacteria are modified to target, infect, colonize, and/or produce an immune response in one or more specific tissues (e.g., to target a particular cancer or tumor type). In some embodiments, uropathogenic bacteria are modified to be non-pathogenic. In some embodiments, uropathogenic bacteria are modified to be non-pathogenic while still eliciting an immune response.

Embodiments herein include uropathogenic bacteria (e.g., *E. coli*, CP1, etc.). Some embodiments herein include unmodified and uropathogenic bacteria (e.g., *E. coli*, CP1, etc.). Other embodiments herein include genetically-modified and uropathogenic bacteria (e.g., *E. coli*, CP1, etc.). In some embodiments, genetically-modified uropathogenic bacteria are produced by recombinant technologies. In some embodiments, recombinant uropathogenic bacteria are genetically modified to produce and/or display one or more tumor-associated antigens, one or more anti-cancer peptides, polypeptides or antibodies, one or more immune checkpoint inhibitors, etc. In some embodiments, a recombinant uropathogenic bacteria are genetically modified to prevent expression of one or more native proteins/peptides of the host organism (e.g., *E. coli*, CP1, etc.), for example, to prevent/reduce virulence, pathogenicity, etc. In some embodiments, genetic modifications are selected to maintain the immunostimulatory characteristics of the host organism (e.g., *E. coli*, CP1, etc.) while enhancing localization (e.g., tissue localization, tumor localization, etc.) and/or anticancer characteristics. In some embodiments, genetic modifications are selected to include a biosynthetic pathway for a an anticancer compound, peptide, drug, etc.

Recombinant DNA, molecular cloning, and genetic modification techniques are well known in the art (See, e.g., Sambrook, J., Fritsch, E. F. and Maniatis, T., Molecular Cloning: A Laboratory Manual, $2^{nd}$ ed.; Cold Spring Harbor Laboratory: Cold Spring Harbor, N.Y., (1989) and by Silhavy, T. J., Bennan, M. L. and Enquist, L. W., Experiments with Gene Fusions; Cold Spring Harbor Laboratory: Cold Spring Harbor, N.Y., (1984); and by Ausubel, F. M. et. al., Current Protocols in Molecular Biology, Greene Publishing and Wiley-Interscience (1987); each of which are hereby incorporated by reference in their entireties). Additional useful methods are described in manuals including Advanced Bacterial Genetics (Davis, Roth and Botstein, Cold Spring Harbor Laboratory, 1980), Experiments with Gene Fusions (Silhavy, Berman and Enquist, Cold Spring Harbor Laboratory, 1984), Experiments in Molecular Genetics (Miller, Cold Spring Harbor Laboratory, 1972) Experimental Techniques in Bacterial Genetics (Maloy, in Jones and Bartlett, 1990), and A Short Course in Bacterial Genetics (Miller, Cold Spring Harbor Laboratory 1992) each of which are hereby incorporated by reference in their entireties.

Uropathogenic bacteria (e.g., *E. coli*, CP1, etc.) may be genetically modified to delete genes or incorporate genes by methods known to those of skill in the art. In some embodiments, genes within the uropathogenic bacteria (e.g., *E. coli*, CP1, etc.) to be inhibited or deleted are known to those of skill in the art or may be determined using methods known to those of skill in the art. In some embodiments, genes, or homologs thereof, to be added to the genome of the uropathogenic bacteria (e.g., *E. coli*, CP1, etc.) are known to those of skill in the art or may be identified and obtained using methods known to those of skill in the art. Vectors and plasmids useful for transformation of host cells are known in the field and commercially or otherwise available.

In some embodiments, a suitable vector or plasmid contains sequences directing transcription and translation of a relevant gene, a selectable marker, and sequences allowing autonomous replication or chromosomal integration. Suitable vectors comprise a region 5' of the gene which harbors transcriptional initiation controls and a region 3' of the DNA fragment which controls transcription termination. Both control regions may be derived from genes homologous to the transformed host cell, although it is to be understood that such control regions may also be derived from genes that are not native to the species chosen as a production host. Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, lac, ara, tet, trp, $IP_L$, $IP_R$, T7, tac, and trc (useful for expression in *Escherichia coli*). Termination control regions may also be derived from various genes native to the preferred hosts, or introduced from *E. coli*, such as $t_{rmB}$ or $t_{T7}$ (Marx and Lidstrom, Microbiology 150:9-19 (2004); incorporated by reference in its entirety).

Certain vectors are capable of replicating in a broad range of host bacteria and can be transferred by conjugation. The complete and annotated sequence of pRK404 and three related vectors-pRK437, pRK442, and pRK442(H) are available. These derivatives have proven to be valuable tools for genetic manipulation in Gram-negative bacteria (Scott et al., Plasmid 50(1):74-79 (2003); incorporated by reference in its entirety). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for the heterologous gene expression in Gram-negative bacteria.

Vectors useful for the transformation of *E. coli* are common and commercially available. For example, the desired genes may be isolated from various sources, cloned onto a modified pUC 19 vector and transformed into *E. coli* host cells. Alternatively, the genes encoding a desired biosynthetic pathway may be divided into multiple operons, cloned onto expression vectors, and transformed into various *E. coli* strains.

Multiple genes to be expressed in a genetically-modified uropathogenic bacteria may be assembled into any suitable vector, such as those described above. The codons can be optimized for expression based on the codon index deduced from the genome sequences of the host strain.

In some embodiments, uropathogenic bacteria (e.g., CP1, genetically-modified uropathogenic bacteria, etc.) are administered and/or the growth thereof is facilitated.

In some embodiments, uropathogenic bacteria (e.g., CP1, genetically-modified uropathogenic bacteria, etc.) are administered as prepared probiotic compositions for administration to/by a subject. Probiotic compositions comprise one or more uropathogenic bacteria (e.g., CP1, genetically-modified uropathogenic bacteria, etc.) formulated such that administration of the probiotic (e.g., orally, rectally, by inhalation, by injection, intratumorally, intraurethrally, intravesically, intraprostatically, etc.) results in population of the subject (or a tissue thereof) by the uropathogenic bacteria.

In some embodiments, probiotic compositions comprise cultured microbes that are combined and/or formulated for administration to a subject. In some embodiments, probiotics contain microbes of known genera, species, etc. and/or at known concentrations (cfus). Probiotic compositions may be in the form of a pharmaceutical-type composition (e.g., capsule, tables, liquid, aerosol, etc.) or in the form of a food supplement.

In some embodiments, probiotic microbes (e.g., uropathogenic bacteria, genetically-modified uropathogenic bacteria, CP1, genetically-modified CP1, etc.) are formulated in a pharmaceutically acceptable composition for delivery to a subject. In some embodiments, probiotics are formulated with a pharmaceutically acceptable carrier suitable for a solid or semi-solid formulation. In some embodiments, probiotic microbes are formulated with a pharmaceutically acceptable carrier suitable for a liquid or gel formulation. Probiotic formulations may be formulated for enteral delivery, e.g., oral delivery, or delivery as a suppository, but can also be formulated for parenteral delivery, e.g., vaginal delivery, inhalational delivery (e.g., oral delivery, nasal delivery, and intrapulmonary delivery), and the like.

The probiotic compositions that find use in embodiments described herein (e.g., comprising: uropathogenic bacteria, genetically-modified uropathogenic bacteria, CP1, genetically-modified CP1, etc.) may be administered intraurethrally or formulated in a wide variety of oral administration dosage forms, with one or more pharmaceutically acceptable carriers. The pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is a mixture with the probiotic microbes. In tablets, the microbes are mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Other forms suitable for oral administration include liquid form preparations such as emulsions, syrups, elixirs, aqueous solutions, aqueous suspensions, or solid form preparations which are intended to be converted shortly before use to liquid form preparations. Aqueous suspensions can be prepared by dispersing the probiotic microbes in water with viscous material, such as natural or synthetic gums, resins, methylcellulose, sodium carboxymethylcellulose, and other well-known suspending agents.

The probiotic compositions (e.g., comprising uropathogenic bacteria, genetically-modified uropathogenic bacteria, CP1, genetically-modified CP1, etc.) may be formulated for administration as suppositories. A low melting wax, such as a mixture of fatty acid glycerides or cocoa butter is first melted and the probiotic microbes are dispersed homogeneously, for example, by stirring. The molten homogeneous mixture is then poured into conveniently sized molds, allowed to cool, and to solidify.

In some embodiments, probiotic compositions (e.g., comprising uropathogenic bacteria, genetically-modified uropathogenic bacteria, CP1, genetically-modified CP1, etc.) may be formulated for delivery by inhalation. As used herein, the term "aerosol" is used in its conventional sense as referring to very fine liquid or solid particles carries by a propellant gas under pressure to a site of therapeutic application. The term "liquid formulation for delivery to respiratory tissue" and the like, as used herein, describe compositions comprising probiotic microbes with a pharmaceutically acceptable carrier in flowable liquid form. Such formulations, when used for delivery to a respiratory tissue, are generally solutions, e.g. aqueous solutions, ethanolic solutions, aqueous/ethanolic solutions, saline solutions and colloidal suspensions.

In some embodiments, probiotic compositions (e.g., comprising uropathogenic bacteria, genetically-modified uropathogenic bacteria, CP1, genetically-modified CP1, etc.) may be formulated for parenteral delivery. Parenteral administration includes aqueous solutions of the in water-soluble form. Compositions and formulations for parenteral administration (e.g., intraperitoneal, intravenous, intraprostatic, intravesical, etc.) may include sterile aqueous solutions that may also contain buffers, diluents and other suitable additives such as, but not limited to, penetration enhancers, carrier compounds and other pharmaceutically acceptable carriers or excipients. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Rather than pharmaceutical-type formulation, probiotic compositions (e.g., comprising uropathogenic bacteria, genetically-modified uropathogenic bacteria, CP1, genetically-modified CP1, etc.) may be formulated as food additive and/or food product and incorporated into a variety of foods and beverages. Suitable foods and beverages include, but are not limited to, yogurts, ice creams, cheeses, baked products such as bread, biscuits and cakes, dairy and dairy substitute foods, soy-based food products, grain-based food products, starch-based food products, confectionery products, edible oil compositions, spreads, breakfast cereals, infant formulas, juices, power drinks, and the like.

In some embodiments, a probiotic composition (e.g., comprising uropathogenic bacteria, genetically-modified uropathogenic bacteria, CP1, genetically-modified CP1, etc.) is administered over a dosing time period (e.g., <1 minute, <1 hour, <2 hours, <4 hours, <6 hours, <12 hours, <24 hours, etc.) in an amount that is sufficient to provide a desired therapeutic benefit (e.g., as a single dose, in combination with other doses, in combination with a co-administered therapeutic, etc.) In some embodiments, the dose of the probiotic composition administered for the dosing time period is concentration of from about 10 to about $1 \times 10^{14}$ colony forming units (cfu) of the microbial agent(s) (e.g., uropathogenic bacteria, genetically-modified uropathogenic bacteria, CP1, genetically-modified CP1, etc.), for example, 10 cfu, 100 cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, or any suitable ranges therein (e.g., from about $10^2$ cfu to about $10^{13}$ cfu, about $1 \times 10^4$ to about $1 \times 10^{11}$ cfu, about $1 \times 10^6$ to about $1 \times 10^9$ cfu, about $1 \times 10^{10}$ to about $1 \times 10^{12}$ cf, etc.), etc.).

In some embodiments, the microbial make-up of a probiotic composition consists or consists essentially of one or more uropathogenic bacteria, genetically-modified uropathogenic bacteria, CP1, genetically-modified CP1, etc. In some embodiments, the microbial make-up of a probiotic composition consists or consists essentially of 1, 2, 3, 4, 5, 6, 7, 8, 9, 10, 15, 20, 25, 30, 40, 50, 60, 70, 80, 90, 100, or any ranges therein (e.g., 1-4, 5-10, 8-20, etc.) strains and/or species of uropathogenic bacteria, genetically-modified uropathogenic bacteria, E. coli, genetically-modified E. coli, CP1, genetically-modified CP1, etc. In some embodiments, a single species or strain of bacteria is at least 95% of the microbial population, as measured by colony forming units, of a particular probiotic composition.

In particular embodiments, one or more uropathogenic bacteria, genetically-modified uropathogenic bacteria, CP1, genetically-modified CP1, etc. are administered to the recipient subject by any suitable delivery mechanism, including but not limited to catheter, enema, colonoscope, nasogastric or nasoduodenal tube, lavage or irrigation, or orally (e.g., in the form of a capsule).

In some embodiments, a microbial agent or population of microbial agents (comprising uropathogenic bacteria, genetically-modified uropathogenic bacteria, CP1, genetically-modified CP1, etc.) is administered by a suitable route over a dosing time period (e.g., <1 minute, <1 hour, <2 hours, <4 hours, <6 hours, <12 hours, <24 hours, etc.) in an amount that is sufficient to provide a desired therapeutic benefit (e.g., as a single dose, in combination with other doses, in combination with a co-administered therapeutic, etc.) In some embodiments, the dose administered for the dosing time period is concentration of from about 10 to about $1 \times 10^{14}$ colony forming units (cfu) of the uropathogenic bacteria (e.g., 10 cfu, 100 cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, or any suitable ranges therein (e.g., from about $10^2$ cfu to about $10^{13}$ cfu, about $1 \times 10^4$ to about $1 \times 10^{11}$ cfu, about $1 \times 10^6$ to about $1 \times 10^9$ cfu, about $1 \times 10^{10}$ to about $1 \times 10^{12}$ cf, etc.), etc.). The dose can be administered in a single unit dose administered at any time during a day. Alternatively the loading dose can be administered in two or more doses administered at a single time of day or at two or more separate times of day. Over the course of multiple dosing periods, the dose can be tapered from an initial dose to a higher dose (or increased from an initial dose to a higher dose), on predetermined timing or by the when the subject and/or clinician based on the results of the treatment. The appropriate dosage amount will vary by, for example, an individual subject's age, weight, condition or disease, severity of disease, etc.

In some embodiments, microbes (e.g., uropathogenic bacteria, genetically-modified uropathogenic bacteria, CP1, genetically-modified CP1, etc.) for probiotic compositions are obtained from culture. In some embodiments, strains of uropathogenic bacteria (e.g., CP1) are genetically engineered to enhance one or more of production (e.g., at scale), formulation, delivery, or the biological effect of the microbe. In some embodiments, microbes are engineered to express a detectable marker that allows tracking of the microbes within a subject, or confirmation that the microbe has colonized the subject. In some embodiments, microbes are engineered to express a cancer therapeutic (e.g., chemotherapeutic, immunotherapeutic, antibodies, etc.), anti-inflammatory agent, of other drug.

In some embodiments, one or more prebiotics are administered to a subject as an independent treatment (e.g., to increase the level of the therapeutic microbe (e.g., uropathogenic bacteria) or in conjunction with other treatments described herein. Prebiotics are agents that increase the in vivo growth rate or activity of desired microbes. In some embodiments, prebiotics are soluble fiber sources. In some embodiments, when prebiotics are administered (e.g., fed) to a subject they are not digested or are not fully digested by the subject's digestive enzymes, but rather support the health of the subject and provide an energy source for the desired microbes and enhance the growth thereof. Prebiotics include, for example, naturally occurring lecithins and/or oleic acid, and are described, for example in U.S. Pat. No. 8,449,878 which is herein incorporated by reference in its entirety.

In some embodiments, administering uropathogenic bacteria (e.g., genetically-modified uropathogenic bacteria, CP1, genetically-modified CP1, etc.) is sufficient on its own to allow the endogenous immune system of a subject to respond to the presence of cancer cells and or tumor growth. However, in other embodiments, the uropathogenic bacteria (e.g., genetically-modified uropathogenic bacteria, CP1, genetically-modified CP1, etc.) is administered along with one or more other cancer therapies. In some embodiments, administering uropathogenic bacteria (e.g., genetically-modified uropathogenic bacteria, CP1, genetically-modified CP1, etc.) treats cancer by a mechanism independent of one or more additional cancer treatments. In other embodiments, administering uropathogenic bacteria (e.g., genetically-modified uropathogenic bacteria, CP1, genetically-modified CP1, etc.) facilitates (e.g., increases the effectiveness of) the cancer treatment. In some embodiments, one or more cancer treatments enhance the effectiveness of the administration of the uropathogenic bacteria (e.g., genetically-modified uropathogenic bacteria, CP1, genetically-modified CP1, etc.). Embodiments herein are not limited by the types of cancer treatments (e.g., surgery, radiation, immunotherapy, chemotherapeutic, etc.) unless specifically noted.

In some embodiments, uropathogenic bacteria (e.g., genetically-modified uropathogenic bacteria, CP1, genetically-modified CP1, etc.) is co-administered with an immunotherapeutic cancer treatment. In some embodiments, the immunotherapeutic cancer treatment encompasses blockade of immune-inhibitory receptors, for example using monoclonal antibodies (mAbs) against CTLA-4 and PD-1/PD-L1 (Wolchok, J. D. et al. The New England Journal of Medicine 369, 122-133 (2013).; Topalian, S. L. et al. Journal of clinical oncology 32, 1020-1030 (2014).; Topalian, S. L. et al. The New England journal of medicine 366, 2443-2454 (2012).; Hodi, F. S. et al. The New England journal of medicine 363, 711-723 (2010).; herein incorporated by reference in their entireties).

In some embodiments, uropathogenic bacteria (e.g., genetically-modified uropathogenic bacteria, CP1, genetically-modified CP1, etc.) is co-administered with an immunotherapy. In some embodiments, the immunotherapy includes the administration of an immune checkpoint inhibitor. Immune checkpoint inhibition broadly refers to inhibiting the checkpoints that cancer cells can produce to prevent or downregulate an immune response. Examples of immune checkpoint proteins include, but are not limited to, CTLA4, PD-1, PD-L1, PD-L2, A2AR, B7-H3, B7-H4, BTLA, KIR, LAG3, TIM-3 or VISTA. Immune checkpoint inhibitors can be antibodies or antigen binding fragments thereof that bind to and inhibit an immune checkpoint protein. Examples of immune checkpoint inhibitors include, but are not limited to, nivolumab, pembrolizumab, pidilizumab, AMP-224, AMP-514, STI-A1110, TSR-042, RG-7446, BMS-936559, BMS-936558, MK-3475, CT 011, MPDL3280A, MEDI-4736, MSB-0020718C, AUR-012 and STI-A1010. In some embodiments, the immune checkpoint inhibitor may be administered via injection (e.g., intravenously, intraperitoneally, intratumorally, intravesically, intraprostatically, subcutaneously, into lymph nodes, etc.), but may also be administered orally, topically, or via aerosol.

In some embodiments, the administration of uropathogenic bacteria (e.g., genetically-modified uropathogenic bacteria, CP1, genetically-modified CP1, etc.) to a subject overcomes immune invasion of cancer cells, tumor, tumor microenvironment, etc. In some embodiments, one or more additional cancer immunotherapies are employed (e.g., concurrently or serially) to make use of the induced immune-responsiveness treated cells/tumor. Suitable immunotherapies may include, but are not limited to: cell-based therapies (e.g., dendritic cell or T cell therapy, etc.), monoclonal antibody (mAb) therapy (e.g., naked mAbs, conjugated mAbs), cytokine therapy (e.g., interferons, interleukins, etc.), adjuvant treatment (e.g., polysaccharide-K), etc.

Examples of antibodies that may find use in the compositions and methods disclosed herein (e.g., co-administration with uropathogenic bacteria), particularly for use in immunotherapies (but not so limited) include, but are not limited, to antibodies such as trastuzumab (anti-HER2/neu antibody); Pertuzumab (anti-HER2 mAb); cetuximab (chimeric monoclonal antibody to epidermal growth factor receptor EGFR); panitumumab (anti-EGFR antibody); nimotuzumab (anti-EGFR antibody); Zalutumumab (anti-EGFR mAb); Necitumumab (anti-EGFR mAb); MDX-210 (humanized anti-HER-2 bispecific antibody); MDX-210 (humanized anti-HER-2 bispecific antibody); MDX-447 (humanized anti-EGF receptor bispecific antibody); Rituximab (chimeric murine/human anti-CD20 mAb); Obinutuzumab (anti-CD20 mAb); Ofatumumab (anti-CD20 mAb); Tositumumab-1131 (anti-CD20 mAb); Ibritumomab tiuxetan (anti-CD20 mAb); Bevacizumab (anti-VEGF mAb); Ramucirumab (anti-VEGFR2 mAb); Ranibizumab (anti-VEGF mAb); Aflibercept (extracellular domains of VEGFR1 and VEGFR2 fused to IgG1 Fc); AMG386 (angiopoietin-1 and -2 binding peptide fused to IgG1 Fc); Dalotuzumab (anti-IGF-1R mAb); Gemtuzumab ozogamicin (anti-CD33 mAb); Alemtuzumab (anti-Campath-1/CD52 mAb); Brentuximab vedotin (anti-CD30 mAb): Catumaxomab (bispecific mAb that targets epithelial cell adhesion molecule and CD3); Naptumomab (anti-5T4 mAb); Girentuximab (anti-Carbonic anhydrase ix); or Farletuzumab (anti-folate receptor). Other examples include antibodies such as Panorex™ (17-1A) (murine monoclonal antibody); Panorex (@(17-1A)) (chimeric murine monoclonal antibody); BEC2 (ami-idiotypic mAb, mimics the GD epitope) (with BCG); Oncolym (Lym-1 monoclonal antibody); SMART M195 Ab, humanized 13' 1 LYM-1 (Oncolym). Ovarex (B43.13, anti-idiotypic mouse mAb); 3622W94 mAb that binds to EGP40 (17-1A) pan-carcinoma antigen on adenocarcinomas; Zenapax (SMART Anti-Tac (IL-2 receptor); SMART M195 Ab, humanized Ab, humanized); NovoMAb-G2 (pancarcinoma specific Ab); TNT (chimeric mAb to histone antigens); TNT (chimeric mAb to histone antigens); Gliomab-H (Monoclonals-Humanized Abs); GNI-250 Mab; EMD-72000 (chimeric-EGF antagonist); LymphoCide (humanized IL.L.2 antibody); and MDX-260 bispecific, targets GD-2, ANA Ab, SMART IDIO Ab, SMART ABL 364 Ab, or ImmuRAIT-CEA.

In some embodiments, an immunotherapy, utilized as a co-therapy with the uropathogenic bacteria (e.g., genetically-modified uropathogenic bacteria, CP1, genetically-modified CP1, etc.) described herein, directly or indirectly targets one of more of: a regulatory T cell, myeloid suppressor cell, or dendritic cell. In another aspect, an immunotherapy specifically targets one of the following molecules: CD4; CD25 (IL-2α receptor; IL-2αR); cytotoxic T-lymphocyte antigen-4 (CTLA-4; CD152); Interleukin-10 (IL-10); Transforming growth factor-beta receptor (TGF-βR); Transforming growth factor-beta (TGF-β); Programmed Death-1 (PD-1); Programmed death-1 ligand (PD-L1 or PD-L2); Receptor activator of nuclear factor-κB (RANK); Receptor activator of nuclear factor-κB (RANK) ligand (RANKL); LAG-3; glucocorticoid-induced tumor necrosis factor receptor family-related gene (GITR; TNFRSF18); or Interleukin-4 receptor (IL-4R). In some embodiments, the immunotherapy acts as an agonist that increases the function of the targeted molecule. In other embodiments, the immunotherapy is an antagonist that inhibits the function of the targeted molecule.

In some embodiments, an immunotherapy, utilized as a co-therapy with the uropathogenic bacteria (e.g., genetically-modified uropathogenic bacteria, CP1, genetically-modified CP1, etc.) described herein, directly or indirectly targets one of more of a specific cytokine, cytokine receptor, co-stimulatory molecule, co-inhibitory molecule, or immunomodulatory receptor that modulates the immune system. In another aspect, one of the following molecules are targeted by co-treatment with uropathogenic bacteria (e.g., genetically-modified uropathogenic bacteria, CP1, genetically-modified CP1, etc.): tumor necrosis factor (TNF) superfamily; tumor necrosis factor-α (TNF-α); tumor necrosis factor receptor (TNFR) superfamily; Interleukin-12 (IL- 12); IL-12 receptor; 4-1BB (CD137); 4-1BB ligand (4-1BBL; CD137L); OX40 (CD134; TNR4); OX40 ligand (OX40L; CD40; CD40 ligand (CD40L); CTLA-4; Programmed death-1 (PD-1); PD-1 ligand I (PD-L1: B7-H1); or PD-1 ligand 2 (PD-L2; B7-DC); B7 family; B7-1 (CD80); B7-2 (CD86); B7-H3; B7-H4; GITR/AITR: GITRL/AITRL; BTLA; CD70; CD27; LIGHT; HVEM: Toll-like receptor (TLR) (TLR 1, 2, 3, 4, 5, 6, 7, 8, 9, 10).

In some embodiments, the compositions for and/or methods comprising uropathogenic bacteria (e.g., genetically-modified uropathogenic bacteria, CP1, genetically-modified CP1, etc.) sensitize cancer cells and/or tumor to treatment by one or more chemotherapeutic agents. In some embodiments, one or more chemotherapies are employed in addition to uropathogenic bacteria (e.g., concurrently or serially) to make use of the induced chemotherapeutic sensitivity. In other embodiments, one or more chemotherapeutics are provided as co-therapies, with or without (known) synergism.

In some embodiments, exemplary anticancer agents suitable for use in compositions and methods described herein include, but are not limited to: 1) alkaloids, including microtubule inhibitors (e.g., vincristine, vinblastine, and vindesine, etc.), microtubule stabilizers (e.g., paclitaxel (Taxol), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies (e.g., conjugated with anticancer drugs, toxins, and/or radionuclides, etc.; neutralizing antibodies; etc.); 9) biological response modifiers (e.g., interferons (e.g., IFN-.alpha., etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); and 22) modulators of p53 protein function.

In some embodiments, the co-administered agents are formulated into a single dose and/or composition. In some embodiments, the co-administered agents are in separate doses and/or compositions. In some embodiments in which separate doses and/or compositions are administered, the doses and/or compositions are administered simultaneously, consecutively, or spaced over a time span (e.g., <30 minutes, 1 hour, 2 hours, 4 hours, 6 hours, 12 hours, 1 day, 2 days, 3 days, 4 days, 5 days, 6 days, 1 week, or more, or any suitable ranges therebetween).

In some embodiments, uropathogenic bacteria (e.g., genetically-modified uropathogenic bacteria, CP1, genetically-modified CP1, etc.) is provided as a co-therapy (e.g., with chemotherapy, with immunotherapy, etc.) with one or more additional therapies that target and/or bind to specific cancer or tumor cell markers. Such markers may be selected from the group including but not limited to, epidermal growth factor receptor (EGFR, EGFR1, ErbB-1, HER1). ErbB-2 (HER2/neu), ErbB-3/HER3, ErbB-4/HER4, EGFR ligand family; insulin-like growth factor receptor (IGFR) family, IGF-binding proteins (IGFBPs), IGFR ligand family (IGF-1R); platelet derived growth factor receptor (PDGFR) family, PDGFR ligand family; fibroblast growth factor receptor (FGFR) family, FGFR ligand family, vascular endothelial growth factor receptor (VEGFR) family, VEGF family; HGF receptor family: TRK receptor family; ephrin (EPH) receptor family: AXL receptor family; leukocyte tyrosine kinase (LTK) receptor family; TIE receptor family, angiopoietin 1, 2; receptor tyrosine kinase-like orphan receptor (ROR) receptor family; discoidin domain receptor (DDR) family; RET receptor family; KLG receptor family; RYK receptor family; MuSK receptor family; Transforming growth factor alpha (TGF-α), TGF-α receptor; Transforming growth factor-beta (TGF-β), TGF-β receptor; Interleukin β receptor alpha2 chain (IL13Ralpha2), Interleukin-6 (IL-6), 1L-6 receptor, interleukin-4, IL-4 receptor, Cytokine receptors, Class I (hematopoietin family) and Class II (interferon/1L-10 family) receptors, tumor necrosis factor (TNF) family, TNF-α, tumor necrosis factor (TNF) receptor superfamily (TNTRSF), death receptor family, TRATL-receptor; cancer-testis (CT) antigens, lineage-specific antigens, differentiation antigens, alpha-actinin-4, ARTC1, breakpoint cluster region-Abelson (Bcr-abl) fusion products, B-RAF, caspase-5 (CASP-5), caspase-8 (CASP-8), beta-catenin (CTNNB1), cell division cycle 27 (CDC27), cyclin-dependent kinase 4 (CDK4), CDKN2A, COA-1, dek-can fusion protein, EFTUD-2, Elongation factor 2 (ELF2), Ets variant gene 6/acute myeloid leukemia 1 gene ETS (ETC6-AML1) fusion protein, fibronectin (FN), GPNMB, low density lipid receptor/GDP-L fucose: beta-Dgalactose 2-alpha-Lfucosyltraosferase (LDLR/FUT) fusion protein, HLA-A2, MLA-A11, heat shock protein 70-2 mutated (HSP70-2M), KIAA0205, MART2, melanoma ubiquitous mutated 1, 2, 3 (MUM-1, 2, 3), prostatic acid phosphatase (PAP), neo-PAP, Myosin class 1, NFYC, OGT, OS-9, pml-RARalpha fusion protein, PRDX5, PTPRK, K-ras (KRAS2), N-ras (NRAS), HRAS, RBAF600, SIRT12, SNRPD1, SYT-SSX1 or -SSX2 fusion protein, Triosephosphate Isomerase, BAGE, BAGE-1, BAGE-2, 3, 4, 5, GAGE-1, 2, 3, 4, 5, 6, 7, 8, GnT-V (aberrant N-acetyl glucosaminyl transferase V, MGAT5), HERV-K MEL, KK-LC, KM-HN-1, LAGE, LAGE-1, CTL-recognized antigen on melanoma (CAMEL), MAGE-A1 (MAGE-1). MAGE-A2, MAGE-A3, MAGE- A4, MAGE-AS, MAGE-A6, MAGE-A8, MAGE-A9, MAGE-A10. MAGE-A11, MAGE-A12, MAGE-3, MAGE-B1, MAGE-B2, MAGE-B5. MAGE-B6, MAGE-C1, MAGE-C2, mucin 1 (MUC1), MART-1/Melan-A (MLANA), gp100, gp100/Pme117 (S1LV), tyrosinase (TYR), TRP-1, HAGE, NA-88, NY-ESO-1, NY-ESO-1/LAGE-2, SAGE, Sp17. SSX-1, 2, 3, 4, TRP2-1NT2, carcino-embryonic antigen (CEA), Kallikrein 4, mammaglobin-A, OA1, prostate specific antigen (PSA), prostate specific membrane antigen, TRP-1/, 75. TRP-2 adipophilin, interferon inducible protein absent in melanoma 2 (AIM-2). BING-4, CPSF, cyclin D1, epithelial cell adhesion molecule (Ep-CAM), EpbA3, fibroblast growth factor-5 (FGF-5), glycoprotein 250 (gp250intestinal carboxyl esterase (iCE), alpha-feto protein (AFP), M-CSF, mdm-2, MUCI, p53 (TP53), PBF, PRAME, PSMA, RAGE-1, RNF43, RU2AS, SOX10, STEAP1, survivin (BIRCS), human telomerase reverse transcriptase (hTERT), telomerase, Wilms' tumor gene (WT1), SYCP1, BRDT, SPANX, XAGE, ADAM2, PAGE-5, LIP1, CTAGE-1, CSAGE, MMA1, CAGE, BORIS, HOM-TES-85, AF15q14, HCA66I, LDHC, MORC, SGY-1, SPO11, TPX1, NY-SAR-35, FTHLI7, NXF2 TDRD1, TEX 15, FATE, TPTE, immunoglobulin idiotypes, Bence-Jones protein, estrogen receptors (ER), androgen receptors (AR), CD40, CD30, CD20, CD19, CD33, CD4, CD25, CD3, cancer antigen 72-4 (CA 72-4), cancer antigen 15-3 (CA 15-3), cancer antigen 27-29 (CA 27-29), cancer antigen 125 (CA 125), cancer antigen 19-9 (CA 19-9), beta-human chorionic gonadotropin, 1-2 microglobulin, squamous cell carcinoma antigen, neuron-specific enolase, heat shock protein gp96. GM2, sargramostim, CTLA-4, 707 alanine proline (707-AP), adenocarcinoma antigen recognized by T cells 4 (ART-4), carcinoembryogenic antigen peptide-1 (CAP-1), calcium-activated chloride channel-2 (CLCA2), cyclophilin B (Cyp-B), human signet ring tumor-2 (HST-2), etc.

Non-limiting examples of cancers that may be treated with the compositions and methods described herein include, but are not limited to: cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In some embodiments, the cancer is a melanoma (e.g., metastatic malignant melanoma), renal cancer (e.g. clear cell carcinoma), prostate cancer (e.g. hormone refractory prostate adenocarcinoma), pancreatic cancer (e.g., adenocarcinoma), breast cancer, colon cancer, gallbladder cancer, lung cancer (e.g. non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies. In some embodiments, the cancer is a solid tumor cancer.

Some embodiments described herein are particularly useful for the treatment of tumors that do not otherwise respond to immunotherapeutic approaches.

In some embodiments, methods are provided for testing sample (e.g., cell, tissue, population of cells, tumor, blood, urine, saliva, etc.) from a subject for one or more biomarkers of cancer, immune evasion, etc. Such biomarkers may comprise nucleic acids, small molecules, proteins, peptides, etc., and may be detected using any suitable assay of technique. In some embodiments, provided herein are DNA-, RNA-, small molecule, and/or protein-based diagnostic methods that either directly or indirectly detect the biomarkers of the evasion of immune response or immunotherapy by cancer cells or tumors. The present invention also provides compositions, reagents, and kits for such diagnostic purposes.

In some embodiments, kits are provided comprising, for example, probiotics or other uropathogenic bacterial compositions described herein. Kits may further comprise instructions, cancer treatments, other therapeutic agents, devices for administration, etc.

EXPERIMENTAL

Example 1

In order to both augment the anti-tumor immune response and overcome tumor immune evasion, CP1, a clinical *E. coli* uropathogen isolated from the prostatic secretions of a patient with chronic prostatitis. Experiments conducted during development of embodiments herein (and described in more detail below) demonstrate that CP1 administration successfully targeted multiple hallmarks of an ideal prostate cancer immunotherapy: 1) increased recruitment of TILs, 2) induction of ICD, 3) induction of pro-inflammatory cytokines (IFNγ, TNFα, IL-2, IL-15, IL-17, IL-9, IL-1α, and G-CSF) and chemokines (RANTES, MIP-2, MIP-10, KC, IP-10), 5) inhibition of VEGF, 4) inhibition of IL-6, 5) activation of the adaptive immune response, 6) no induction of immunosuppressive cell types, such as Tregs and MDSCs, and 7) optimization and increased infiltration of antigen-presenting cells. Increased TILs, both before and during the course of anti-PD-1 administration, is strongly linked to efficacy of checkpoint inhibition (Ref. 1; incorporated by reference in its entirety). DAMPS released and exposed in ICD, specifically HMGB1, ATP, and calreticulin, promote APC recruitment, activation, antigen uptake, and optimized antigen presentation, as well as type I cytokine production, leading to an enhanced adaptive anti-tumor immunity (Ref 53; incorporated by reference in its entirety). Further, IFNγ and many of the other upregulated cytokine and chemokines in this study are linked to the anti-tumor immune response. In contrast, VEGF has many immunosuppressive qualities, including increasing Treg, tumor associated macrophages, and MDSC differentiation and activity, decreased APC maturation, and decreased ability of T cells to traffic into tumors and perform effector functions, and thus its inhibition has been a target for immunotherapy (Ref. 54; incorporated by reference in its entirety). Likewise, IL-6 also has many pro-tumorigenic characteristics, and specifically in prostate cancer is linked to disease progression and worsened outcome, increased AR activity, as well as resistance to ADT, enzalutamide, docetaxel, and radiation therapy (through recruitment of MDSCs), and as a result has also been a target for inhibition (Refs. 55-60; incorporated by reference in their entireties).

This multifaceted efficacy of CP1 was demonstrated using FTY720, which specifically blocks T cell egress from lymph nodes into peripheral tissues. FTY720 administration successfully inhibited the increased TILs seen in CP1+PD-1 treated mice, and, a result, tumors from CP1+PD-1 treated mice were significantly smaller than those given the additional administration of FTY720. However, CP1+PD-1+ FTY720 treated tumor (mean 917 mm$^3$) were smaller than untreated (mean 1157 mm$^3$) or FTY720 alone administered (mean 1394 mm$^3$) tumors, indicating that PD-1 blockade and the facets of CP1 efficacy outside of increasing TILs still played a functional role.

Another major advantage of CP1 is that this therapeutic may be implemented as a one-time instillation that specifically colonizes prostate epithelial tumors for a prolonged amount of time, continuously stimulating all of its above described anti-tumor activities. Mice with greatest survival times all had high levels of 16S, indicating that bacterial burden was important for immunotherapy efficacy. Yet, there was no increase in bacterial burden over time, indicating that CP1 levels remained controlled by the host immune system. In addition, CP1 administration did not result in increased levels of liver, renal, or other tissue-specific lab values, as well as no CBC abnormalities, therefore indicating no systemic toxicities.

Experiments conducted during development of embodiments herein conclusively demonstrate the anti-tumor efficacy of the combination of CP1 and PD-1 blockade, as well as the consistent mild efficacy of either modality alone. Experiments included multiple readouts, including mouse survival, tumor size, and in vivo bioluminescent imaging. A major strength of this study is the clinical relevance of the multiple models of prostate cancer. With the lack of murine prostate cancer cell lines, few studies have utilized fully immunocompetent mice, those that do almost always study subcutaneous tumors that may have no true resemblance to the prostate microenvironment, with survival analyses that only reflect cell growth rates. Here, we utilized the androgen-dependent Myc-CaP cell line, (Refs. 61-62; herein incorporated by reference in their entireties) driven by c-Myc overexpression, as is seen in 80-90% of prostate tumors (Ref 63; herein incorporated by reference in its entirety). Additionally, we surgically instilled these cells into the mouse prostate, allowing for orthotopic tumor development with a prostatic microenvironment and endogenous draining lymph nodes. Further, we utilized CRISPR-Cas9 to knock out PTEN from the Myc-CaP genome. MYC copy number gain and PTEN copy number loss is the only CNA combination associated with prostate cancer-specific mortality, and was seen in 57% of metastatic tumors at autopsy relative to 9.6% in localized disease (Ref. 31; herein incorporated by reference in its entirety). This cell line displayed many characteristics of not only more advanced and immunosuppressive cancer, but specifically CRPC, with increased AR and superior growth in low and charcoal-stripped serum, thereby allowing us to test this immunotherapy in multiple stages of the disease.

While we extensively established the safety of CP1, future studies can attempt to attenuate any potential virulence without losing the inflammatory characteristics important for its anti-tumor activities. Additionally, CP1 can be engineer its increase its immunotherapeutic potency. Prior BCTs have engineered bacteria to deliver bacterial cytolytic and adjuvant agents (Refs. 64-66; herein incorporated by reference in their entireties), cytokines and chemokines, or tumor-associated antigens, such as PSA and PSCA (Refs. 67-71; herein incorporated by reference in their entireties).

In summary, CP1 proved to be a multifaceted immuotherapy, increasing TILs, tumor immunogenicity and ICD, pro-inflammatory cytokine and chemokine production, and decreasing immunosuppressive molecules. The combination of CP1 and PD-1 blockade was tested in multiple, clinically relevant, orthotopic, syngeneic models of prostate cancer, and consistently demonstrated efficacy in decreasing tumor burden and increasing survival. In the most prevalent cancer type responsible for the second most deaths in men, we report a novel immunotherapeutic tool to optimize the otherwise ineffective PD-1 antibody in this disease.

Methods

Animals

FVB mice (Jackson Laboratories; Bar Harbor, Me.) used in this study were housed in a pathogen-free animal barrier facility, and all procedures were performed with the approval of the Northwestern University Institutional Animal Care and Use Committee (IACUC).

Cells Lines and Culture

Myc-CaP, LNCaP, and 293T cells lines were purchased from ATCC and were verified to be mycoplasma-free (Biotool). 293T cells were growth in DMEM (Corning), Myc-CaP and LNCaP in RPMI (Gibco), all supplemented with 10% heat inactivated (H.I.) fetal bovine serum (FBS; Corning) and 1% Penicilin-Streptomycin (10,000 U/ml; Life Technologies). All cell culture was performed in a 37° C. 5% $CO_2$ incubator. Cells were passaged using phosphate buffered saline (PBS; VWR) and trypsin-EDTA (0.25%; Gibco).

Bacterial Growth and Inoculation

For In Vitro and In Vivo Experiments, CP1 was Grown in Luria

Broth (LB) media (Sigma) incubated 24 hours shaking followed by 24 hours static at 37° C. Bacteria were subsequently collected and resuspended in PBS at an OD420 of 1.0+/−0.01 ($2\times10^{10}$ cells/ml). For indicated in vitro assays, CP1 was heat killed at 70° C. for 45 minutes. For in vivo experiments, 10 µl CP1 ($2\times10^8$ cells) or sterile PBS were administered intra-urethrally by catheterization to isoflurane anesthetized mice.

Gentamicin Protection Assay and Cell Death Assay

Tumor cells were incubated with CP1 (multiplicity of infection [MOI] 10) in antibiotic-free media for 3 hours at 37° C. 5% $CO_2$. To assess bacterial invasion, cells were washed 4 times with PBS, treated with 100 µg/ml gentamicin, incubated with 0.05% trypsin/0.1% Triton X-100 for 10 mins at 37° C. 5% $CO_2$, and then cells were harvested, plated on LB agar, and colonies counted after 24 hours. To assess bacterial adherence, cells were washed followed by immediate trypsin/Triton X-100 incubation and collection. Adherence was calculated as this bacterial count subtracted from the invasion count. To assess intracellular proliferation of bacteria, cells were washed and incubated with 100 µg/ml gentamicin for 21 hours at 37° C. 5% $CO_2$, followed by cell collection. Additionally, supernatant was assessed for lactate dehydrogenase (LDH) levels as a measure of cell death (CytoTox 96 Non-Radioactive Cytotoxicity Assay, Promega).

Immunogenic Cell Death Assays

Tumor cells were incubated with 1 µM mitoxantrone, live CP1 (MOI 10), or heat killed CP1 (MOI 10) for 24 or 72 hours. Cells counts were taken at the times of supernatant collection, which were frozen at −80° C. until use for quantifying secreted ATP (Bioluminescent Assay Kit, Sigma) and HMGB1 (ELISA, Tecan Trading). Cells were also incubated with rabbit anti-calreticulin (Abcam ab2907 1:1000) for 60 minutes on ice, followed by Alexa Fluor 488 goat anti-rabbit (Invitrogen A11008 1 µg/ml) 30 mins on ice, and calreticulin levels were measured by flow cytometry.

Multiplex

Tissues lysates were prepared in RIPA buffer (Sigma) supplemented with protease (cOmplete, Mini, EDTA-free; Sigma) and phosphatase inhibitors. Tissues were homogenized by electric pestle or using a gentleMACS dissociator with gentleMACS M Tubes (MACS Miltenyi Biotec). 10 µg protein (from tissue) or 25 µl supernatant (from in vitro) were added per well of a 32-plex mouse cytokine/chemokine magnetic bead milliplex plate (EMD Millipore). The plate was run using a MAGPIX Luminex plate reader (Thermo Fisher Scientific) and analyzed on xPONENT Software Solutions.

293T Transfection and Lentiviral Transduction of Tumor Cells

Lentivirus was produced through co-transfection of 293T cells with a luciferase expressing vector (pLV-mCherry-P2A-luciferase; 3 µg), Δ8.9 HIV-1 packaging vector (2 µg), and VSVG envelope glycoprotein vector (1 µg) with the addition of lipofectamine 2000 (2.5 µl/µg DNA) in Opti-MEM media in 6-well plates at 37° C. 5% $CO_2$ for 16 hours. Supernatant virus was collected, 0.45 µm filtered, and stored at −80° C. Virus was diluted 1:5 and supplemented with polybrene (8 µg/ml) to spinfect Myc-CaP cells for 2 hours at 32° C. At least 48 hours later, mCherry positivity was verified and sorted for top 10% using a FacsAria SORP cell sorter (BD).

Orthotopic Surgical Tumor Model

For intra-prostatic surgical injections, tumor cells were resuspended $1\times10^6$ cells/30 µl (1:1 PBS and matrigel [Basement Membrane Mix, Phenol Red-Free, LDEV-Free, Corning]). Mice were anesthetized with isofluorane (2-5% for induction, 1-3% for maintenance), verified by toe pinch, and were administered buprenorphine (0.05-1 mg/kg). The abdominal region was shaved and sterilized with Betadine and ethanol. Under sterile conditions, $1\times10^6$ tumor cells were injected (Hamilton syringe and 28-gauge needles) into one anterior prostate lobe, initially verified by engorgement of the lobe. Surgical site was closed with 5-0 absorbable sutures (J493G, eSutures) on the inner abdominal wall and 4-0 non-absorbable sutures (699H, eSutures) on the outer skin. Meloxicam (1-2 mg/kg) was administered immediately, 24, and 48 hours post-surgery.

Survival endpoint was defined by the appearance of hemorrhagic abdominal ascites and/or decreased grooming, ambulation, or piloerection. Volume of all tumor experiments was calculated using caliper measurements at $\pi/6\times L\times W\times H$, where L is length of longest axis of the tumor, and W and H are the perpendicular width and height, respectively.

For all in vivo experiments, CP1 was administered intra-urethrally on day 8 post-tumor injection. Anti-PD-1 antibody (100 µg; RMP1-14, BioXCell) or IgG2a isotype control (100 µg; clone 2A3, BioXCell) was administered intraperitoneally (i.p.) every other day from 0-21 days post-infection (d.p.i.) for wildtype Myc-CaP experiments and from 5-15 d.p.i. for PTEN knockout Myc-CaP experiments. For select experiments, Fingolimod (FTY720, Sigma) was administered 25 µg intra-venously (i.v.) 24 hours prior to CP1 administration followed by i.p. 5 µg daily injections until analysis.

In Vivo Bioluminescent Imaging

Luciferase-expressing tumor-bearing mice were injected i.p. with 10 µl/g body weight of 15 mg/ml 0.22 m filtered D-luciferin (sodium salt, Gold Bio). 10 minutes after injection, mice were imaged with an IVIS Spectrum Imaging System (PerkinElmer). Images were analyzed and quantified using Living Image software.

In Vivo Bacterial Colonization

Tumors, bladders, kidneys, livers, and spleens were aseptically excised, dissected, and homogenized by electric pestle. Serial dilutions were plated on eosin methylene blue (EMB) agar and incubated at 37° C. for 24 hours.

RNA Extraction, cDNA, qRT-PCR

Excised tissue was immediately placed in RNAlater at 4° C. for 24 hours followed by removal of RNAlater and storage at −80° C. until use. Tissue was homogenized using TissueMiser Homogenizer (Fisher Scientific) and RNA was extracted by Trizol (Thermo Fisher Scientific) and subsequent RNAeasy Plus Mini kit (QIAGEN). cDNA was generated from 2 µg or 400 ng RNA with 2 µM oligo d(T)$_{16}$ primer (Invitrogen) and 50 ng/µl random hexamer (Promega) at 68° C. for 10 mins, followed by 42° C. for 1 hour and 95° C. for 5 mins after the addition of 700 nM dNTPs (Promega), 1× first strand buffer (Invitrogen), 14 mM DTT (Research Products International), 1.4 U/µl SUPERase-In RNase inhibitor (Invitrogen), and 3.5 U/µl M-MLV reverse transcriptase (Invitrogen). Quantitative RT-PCR was performed using a QuantStudio 6 Flex Real-Time PCR System (Applied Biosystems) at 50° C. for 2 mins, 95° C. for 10 mins, and 40 cycles of 95° C. for 15 sec and 60° C. for 1 min using SYBR Green master mix (Bio-Rad) and the following primers: 16S (F: ACTCCTACGGGAGGCAGCAGT, R: TATTACCGCGGCTGCTGGC) or the mouse housekeeping gene Rplp0 (F: AGATGCAGCAGATCCGCA, R: GTTCTTGCCCATCAGCACC) (Integrated DNA Technologies). Data was analyzed using QuantStudio Real-Time PCR software v1.3.

Flow Cytometry

Single cell suspensions were generated from tumors using a gentleMACS Dissociator with Heaters with the Tumor Dissociation Kit (MACS Miltenyi Biotec) in gentleMACS C Tubes (MACS Miltenyi Biotec). Tissues were passed through a 70 m filter, resuspended in 30% Percoll (Sigma), and carefully overlayed on top of 70% Percoll. After centrifuging without brakes, the buffy coat layer was isolated and viable cells were counted. Tumor-draining aortic lumbar lymph nodes single cell suspensions were created by passing cells directly through a 70 m filter, followed by red blood cell lysis with ACK buffer (0.15M NH$_4$Cl, 10 mM KHCO$_3$, 0.1 mM Na$_2$-EDTA; pH 7.2-7.4; 0.2 m filtered) and subsequent cell counts. All samples were treated with Fc block (BD 553141).

Cells for intracellular staining were resuspended in RPMI 10% FBS with PMA (50 ng/ml, Sigma), ionomycin (1 µg/ml, Cell Signaling), Brefeldin A (GolgiPlug 1 µl/ml; BD), and monensin (GolgiStop 2 µl/3 ml; BD) for 6 hours at 37° C. For cells stained with CD107a, the antibody was added for the duration of the stimulation.

Antibodies utilized for flow cytometry included rat/hamster anti-mouse CD45-PE (BD 30-F11), CD3ε-V500 (BD 500A2), CD4-BV786 (BD RM4-5), CD8α-BUV395 (BD 53-6.7), CD25-BV421 (BD PC61), FoxP3-eFluor 660 (eBioscience FJK-16s), CD11b-Alexa Fluor 700 (BD M1/70), Gr-1-BUV395 (BD RB6-8C5), γδ TCR-BV421 (BD GL3), NKp46-Alexa Fluor 700 (BD 29A1.4), B220-BV786 (BD RA3-6B2), F4/80-BV421 (BD T45-2342), MHCII (I-A/I-E)-V500 (BD M5/114.15.2), CD107a-BV786 (BD 1D4B), IFNγ-Alexa Fluor 488 (BioLegend XMG1.2), TNF-Alexa Fluor 700 (MP6-XT22), IL-17α-BUV395 (BD TC11-18H10), Granzyme B-eFluor 450 (eBioscience NGZB), Perforin-APC (eBioscience eBioOMAK-D), PD-1-APC (BD J43), CD95-BV421 (BD Jo2), and CD95L-APC (eBioscience MFL3). Antibodies utilized for flow cytometry are listed in Table 1, and all antibodies were individually titrated to determine optimal staining dilutions.

TABLE 1

Primary antibodies used in this study for flow cytometry.

| Antigen (mouse) | Label | Clone | Vendor | Catalog # |
|---|---|---|---|---|
| Calreticulin | Unconjugated | | Abcam | ab2907 |
| Annexin V | FITC | | eBioscience | 11-8005 |
| PI | — | | eBioscience | 00-6690 |
| CD45 | PE | 30-F11 | BD | 553081 |
| CD3ε | V500 | 500A2 | BD | 560771 |
| CD4 | BV786 | RM4-5 | BD | 563727 |
| CD8α | BUV395 | 53-6.7 | BD | 563786 |
| CD25 | BV421 | PC61 | BD | 562606 |
| FoxP3 | eFluor 660 | FJK-16s | eBioscience | 50-5773-80 |
| CD11b | Alexa Fluor 700 | M1/70 | BD | 557960 |
| Gr-1 | BUV395 | RB6-8C5 | BD | 563849 |
| γδ TCR | BV421 | GL3 | BD | 562892 |
| NKp46 | Alexa Fluor 700 | 29A1.4 | BD | 561169 |
| B220 | BV786 | RA3-6B2 | BD | 563894 |
| F4/80 | BV421 | T45-2342 | BD | 565411 |
| CD11c | BV786 | HL3 | BD | 563735 |
| CD80 | FITC | 16-10A1 | BD | 563727 |
| CD107a | BV786 | 1D4B | BD | 564349 |
| IFNγ | Alexa Fluor 488 | XMG1.2 | BioLegend | 505813 |
| TNFα | Alexa Fluor 700 | MP6-XT22 | BD | 558000 |
| IL-17A | BUV395 | TC11-18H10 | BD | 565246 |
| Granzyme B | eFluor 450 | NGZB | eBioscience | 48-8898-80 |
| Perforin | APC | eBioOMAK-D | eBioscience | 17-9392-80 |
| PD-1 | APC | J43 | BD | 562671 |
| PD-L1 | APC | 10F.9G2 | BioLegend | 124312 |
| PD-L2 | BV421 | TY25 | BD | 1564245 |
| CD95 | BV421 | Jo2 | BD | 562633 |
| CD95L | APC | MFL3 | eBioscience | 17-5911-80 |

After extracellular staining for 1 hour, all cells were subsequently stained with LIVE/DEAD Fixable Blue Dead Cell Stain Kit (Invitrogen), and all non-FoxP3 panels were resuspended 1:1 with PBS 2% FBS and IC fixation buffer (eBioscience) overnight at 4° C. For FoxP3 staining, cells were fixed and permeabilized with the FoxP3/Transcripition Factor Staining Buffer Set Kit (eBiosceince), followed by incubation with anti-FoxP3 antibody for 30 minutes at room temperature. For non-FoxP3 intracellular staining, cells were permeabilized with the Intracellular Fixation and Permeabilization Buffer Set Kit (eBioscience) and incubated with intracellular antibodies for 60 minutes at room temperature.

Figure 9A:
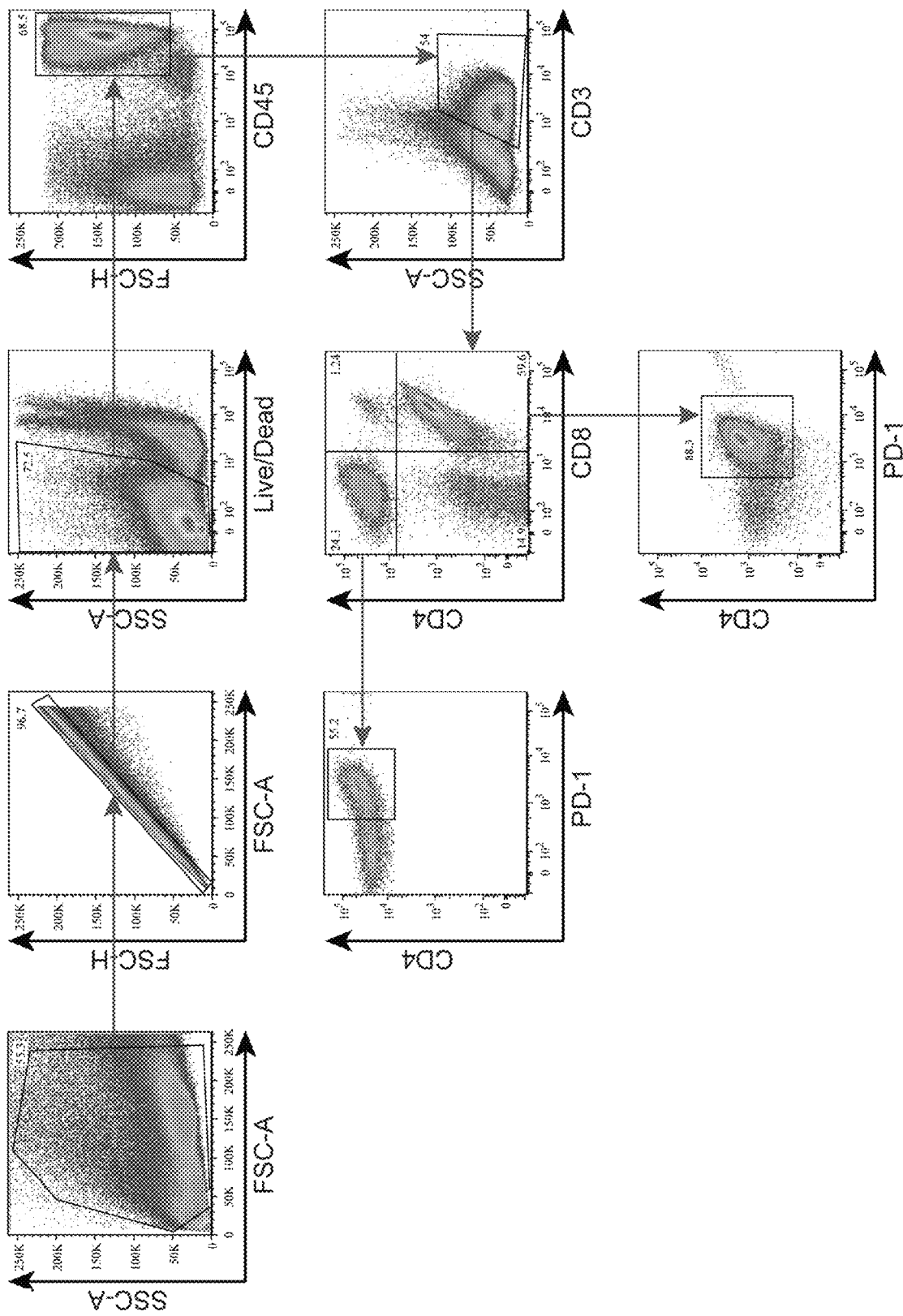
FIG. 9. Representative flow cytometry gating strategy. For flow cytometry data, gating was performed to remove debris and capture singlets, live cells, and CD45+ cells, followed by CD3+, CD4+, CD8+, and PD-1+ cells, or other antigens of interest from A) tumor or B) dLNs.
Figure 9B:
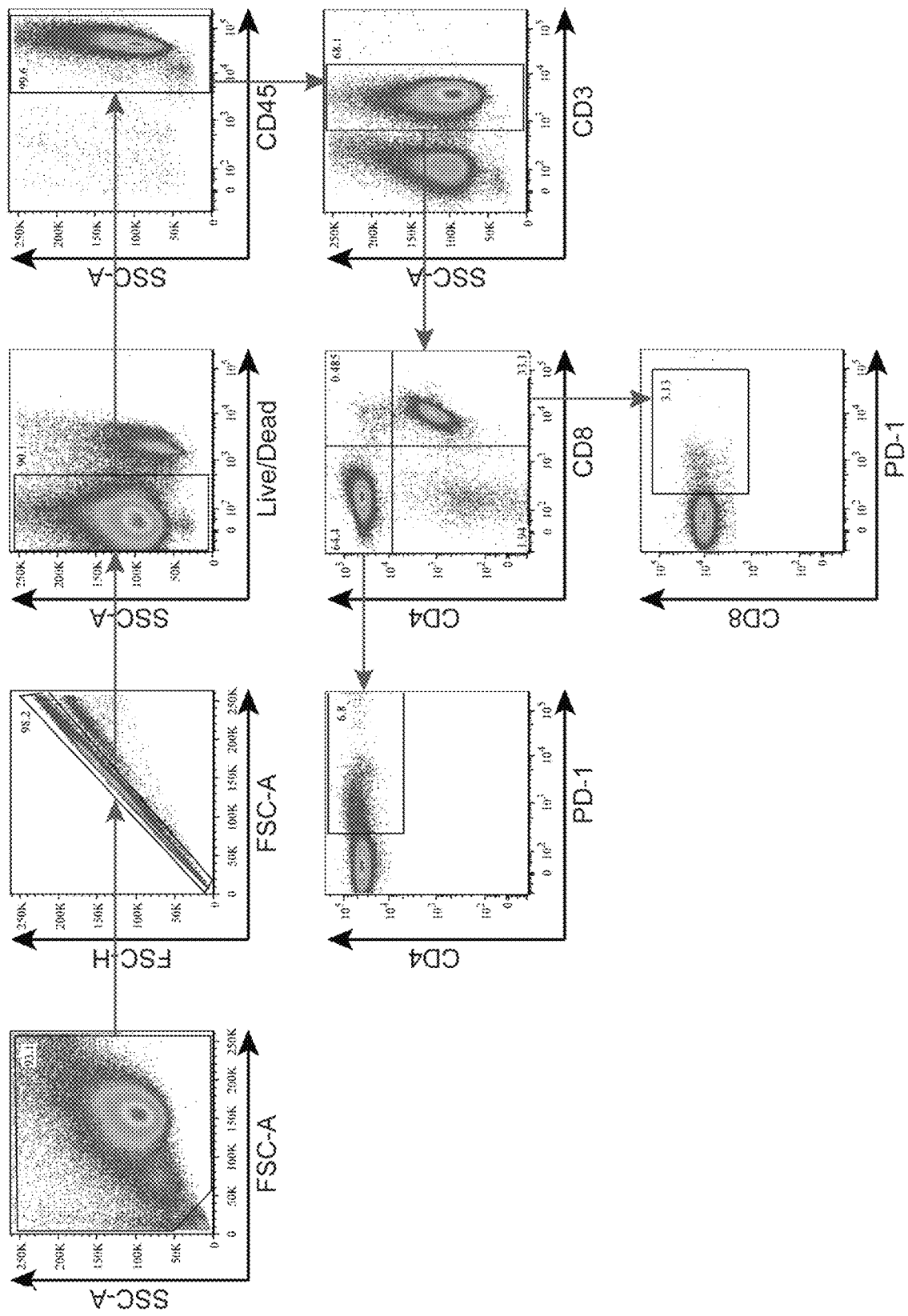

Samples were run on a LSRFortessa 6-Laser (BD). Controls were performed using anti-rat/hamster Ig, κ/negative control compensation particles set (BD), as well as appropriate fluorescence minus one and unstained controls. Data was analyzed using FlowJo software. Representative flow cytometry gating strategy is displayed in FIG. 9 (A: tumor; B: dLNs).

Histology

Tissues were fixed in 10% neutral buffered formalin for 24-48 hours at 4° C. and subsequently washed in PBS and transferred to 70% ethanol. For immunohistochemistry (IHC), 5 m sections were deparaffinized and rehydrated, followed by antigen retrieval with citrate buffer pH6 (FIG. 2: 1 mM EDTA pH 8; FIG. 6,7: Dako), incubation in 3% H$_2$O$_2$ (Sigma) in water (FIG. 2) or methanol (FIG. 6, 7), blocking (CD3 FIG. 2: BioCare Blocking Reagent BS966M; CD3 FIG. 6,7: Dako X0909 for Ventana; Fibrinogen: Vector ImmPRESS 2.5% normal horse serum), primary antibody incubation, secondary antibody incubation (CD3 FIG. 2: Vector biotinylated rabbit anti-rat IgG; CD3 FIG. 6,7: Dako EnVision+ System HRP for Ventana; Fibrinogen: Vector ImmPRESS HRP), streptavidin-HRP (Biocare) for fibrinogen, 3,3'-Diaminobenzidine chromogenic detection (SIGMAFASTtablets, Sigma), hematoxylin counterstain (H-3404), tissue dehydration, and slide mounting (Cytoseal-XYL).

CD3 IHC (FIG. 2) slides were blinded and scored manually over the entire surface area of tissue, while CD3 (FIG. 6, 7) and fibrinogen IHC 460 nm images were quantified using ImageJ for cell count or total and mean intensity, respectively, with quadruplicate field of views (FOVs) analyzed per sample (20× for CD3, 10× for fibrinogen).

For immunofluorescence (IF), the above protocol was repeated, with primary anti-E. coli antibody incubation, followed by streptavidin-Alexa Fluor 594 secondary antibody (ThermoFisher Scientific 1:500), subsequent permeabilization with PBST (1×PBS with 0.25% Triton-X-100), repeated primary antibody, then goat anti-rabbit IgG (H+L) Alexa Fluor 488 secondary antibody (ThermoFisher Scientific 1:500), and DAPI (Sigma) counterstain and mounting with ProLong Gold Antifade Mountant (Invitrogen/Molecular Probes), resulting in green intracellular staining and yellow (green+red) extracellular staining. For co-IF of E. coli and HIF-1α, primary anti-HIF-1α was applied first with secondary anti-rabbit Alexa Fluor 488, followed by primary anti-E. coli and secondary streptavidin-Alexa Fluor 594.

Antibodies utilized for IHC included rabbit anti-CD3 (FIG. 2: Bio-Rad CD3-12 1:100; FIG. 6, 7: Ventana 2GV6), rabbit anti-fibrinogen (Abcam ab34269 1:200), and anti-CD31. Antibodies used for IF included biotinylated rabbit anti-E. coli (Abcam 20640 1:500) and rabbit anit-HIF-1α (Novus Biologicals NB100-134 1:100). Primary IHC and IF antibodies are listed in Table 2.

TABLE 2

Primary antibodies used in this study for histology.

| Antigen (mouse) | Dilution | Protocol | Clone | Vendor | Catalog # |
|---|---|---|---|---|---|
| E. coli | 1:500 | IF | | Abcam | ab20640 |
| HMGB1 | 1:1000 | IF | | Abcam | ab18256 |
| Calreticulin | 1:500 | IF | | Abcam | ab2907 |
| CD3ε | 1:100 | IHC | CD3-12 | Bio-Rad | MCA1477T |
| CD3ε | Pre-diluted | IHC | 2GV6 | Ventana | 790-4341 |
| Fibrinogen | 1:200 | IHC | ab34269 | Abcam | ab34269 |

Light microscopy images were taken with a SPOT RT Color camera on a Olympus CKX41 inverted microscope, IHC images with CRI Nuance spectral camera on a Zeiss Axioskop upright microscope or a NikonDS-Ri2 microscope, and IF images with a Nikon A1R+ confocal microscope.

Chemistry Panel, Complete Blood Count (CBC)

Mouse peripheral blood was collected by cardiac puncture and placed in serum separator or dipotassium-EDTA tubes (BD Microtainer). Frozen serum and whole blood were analyzed by Charles River Laboratory, the latter within 24 hours after collection. Reference value ranges were used from the Charles River Laboratory, the University of Arizona University Animal Care (uac.arizona.edu/clinical-pathology), and the University of Minnesota Research Animal Resources (www.ahc.umn.edu/rar/refvalues.html).

CRISPR

To stably express CAS9 in Myc-CaP cells, VSVG pseudotypes lentivirus we generated using 293T cells (Gene Hunter Corporation), $2^{nd}$ generation packaging vectors psPAX2, pMD2.G, and CAS9 (S. pyogenes CRISPR-Cas) expressing lentiviral vector (Addgene 52962). Lentiviral infection efficacy was >90% and cells were maintained with 8 µg/ml puromycin. 4 synthetic gRNAs (CRISPR crRNA, Integrated DNA Technologies; #1: GCTAACGATCTCTTTGATGA exon 1, #2: AAAGACTTGAAGGTGTATAC exon 2, #3: TGTGCATATTTATTGCATCG exon 5, #4: GGTTTGA-TAAGTTCTAGCTG exon 5) were designed using the CRISPR Design Tool (crispr.mit.edu). The top ranked gRNAs with no off-target effects were selected and were delivered by transient transfection reagent TransIT-X2 (Mirus Bio). Partial PTEN knockout was confirmed by western blot and IF. With the top 2 (#2, #3 gRNAs) most efficient gRNA knockdown lines, over 40 clones were selected by cloning cylinders and further screened for complete PTEN knockdown by western blot. 2 complete PTEN knockdown Myc-CaP clones from different gRNAs were selected and analyzed in parallel in vitro before proceeding with one in vivo (from #2 gRNA).

Cancer Genomic Database Analysis cBioPortal for Cancer Genomics (cbioportal.org) was utilized to analyze The Cancer Genome Atlas (TCGA) Research Network (cancergenome.nih.gov/) and the Stand Up To Cancer/Prostate Cancer Foundation (SU2C/PCF) database.

Western Blot

Lysate protein quantification was performed by the Bradford method with Protein Assay Dye (Bio-Rad) in a VICTOR³ multilabel reader (PerkinElmer). Lysate was combined with Laemmli sample buffer (Bio-Rad) with 2-mercaptoethanol (Bio-Rad), incubated 95° C. 5 min, and loaded on Mini-PROTEIN TGX precast 10% gels (Bio-Rad) and run in Tris/Glycine/SDS running buffer (Bio-Rad). Protein was transferred to PVDF membranes in a Trans-Blot Turbo transfer system (Bio-Rad). Blocking, primary antibody, and secondary antibody incubations were done in 5% blotting-grade blocker nonfat dry milk (Bio-Rad) in TBST (TBS with 0.1% Tween-20 [ChemCruz]). Protein was detected using SuperSignal West Pico PLUS enhanced chemiluminscent (ECL) horseradish peroxidase (HRP) substrate (ThermoFisher Scientific) in a LAS-3000 imager (FUJIFILM). When appropriate, blots were stripped with Restore PLUS western blot stripping buffer (ThermoScientific) and re-probed. Western blot antibodies included rabbit anti-PTEN (Cell Signaling 138G6 1:1000), phosphorylated-AKT (p-AKT; Cell Signaling S473 1:1000), pan-AKT (Cell Signaling C67E7 1:1000), AR (Santa Cruz Biotechnology N-20 1:2000), c-Myc (Abcam Y69 1:1000), PD-L1 (Abcam ab58810 1:400), and β-actin (Sigma AC-74 1:3000). Goat anti-rabbit IgG (H+L)-HRP conjugate (Bio-Rad) was used as the secondary antibody. Primary antibodies for Western blot are listed in Table 3.

TABLE 3

Primary antibodies used in this study for western blot.

| Antigen (mouse) | Dilution | Clone | Vendor | Catalog # |
|---|---|---|---|---|
| p-MLKL | 1:1000 | EPR9515(2) | Abcam | ab196436 |
| MLKL | 1:1000 | | Abcam | ab172868 |
| RIP1 | 1:1000 | 38/RIP | BD Biosciences | 610458 |
| RIP3 | 1:1000 | | Bio-Rad | AHP1797 |
| PARP | 1:1000 | H-250 | Santa Cruz Biotechnology | sc-7150 |
| PTEN | 1:1000 | 138G6 | Cell Signaling | 9559 |
| p-AKT | 1:1000 | S473 | Cell Signaling | 4060 |
| pan-AKT | 1:1000 | C67E7 | Cell Signaling | 4691 |
| AR | 1:2000 | N-20 | Santa Cruz Biotechnology | sc-816 |

TABLE 3-continued

Primary antibodies used in this study for western blot.

| Antigen (mouse) | Dilution | Clone | Vendor | Catalog # |
| --- | --- | --- | --- | --- |
| c-Myc | 1:1000 | Y69 | Abcam | ab32072 |
| β-actin | 1:3000 | AC-74 | Sigma | A5316 |

Cell Proliferation Assay

Cell proliferation was assessed by quantification of MTS tetrazolium reduction (Promega). Select experiments were performed under low (1% FBS) or charcoal-stripped (C.S.) serum conditions.

Organoid Culture

As previously described, cells were resuspended in Hepatocyte Defined Medium (Corning) supplemented with 10 ng/ml epidermal growth factor (EGF; Corning), 5% C.S. H.I. FBS, 1× Glutamax (Gibco), 5% matrigel (Corning), 10 uM ROCK inhibitor (Y-27632; STEMCELL Technologies), 100 nM DHT (Sigma), and 1× Gentamicin/Amphotericin (Lonza). Cells were plated in Ultra-Low Attachment Surface plates (Corning).

Statistical Analyses

Statistical analyses were performed in GraphPad Prism software. T tests, one-way Analysis of Variance (ANOVA) with post-hoc Tukey, and two-way ANOVA with post-hok Sidak were utilized as appropriate. Survival studies were analyzed by Log-rank (Mantel-Cox) tests. Slopes of linear regression trend lines were compared by Analysis of Covariance (ANCOVA). Graphs are represented as mean with standard error of the mean (SEM). *=$p<0.05$, =$p<0.01$, *=$p<0.001$, ****=$p<0.0001$.

Results

CP1 is a Prostate-Tropic Bacteria that Specifically Homes to Prostate Tumor Tissue without Causing Systemic Toxicities.

Figure 15A:
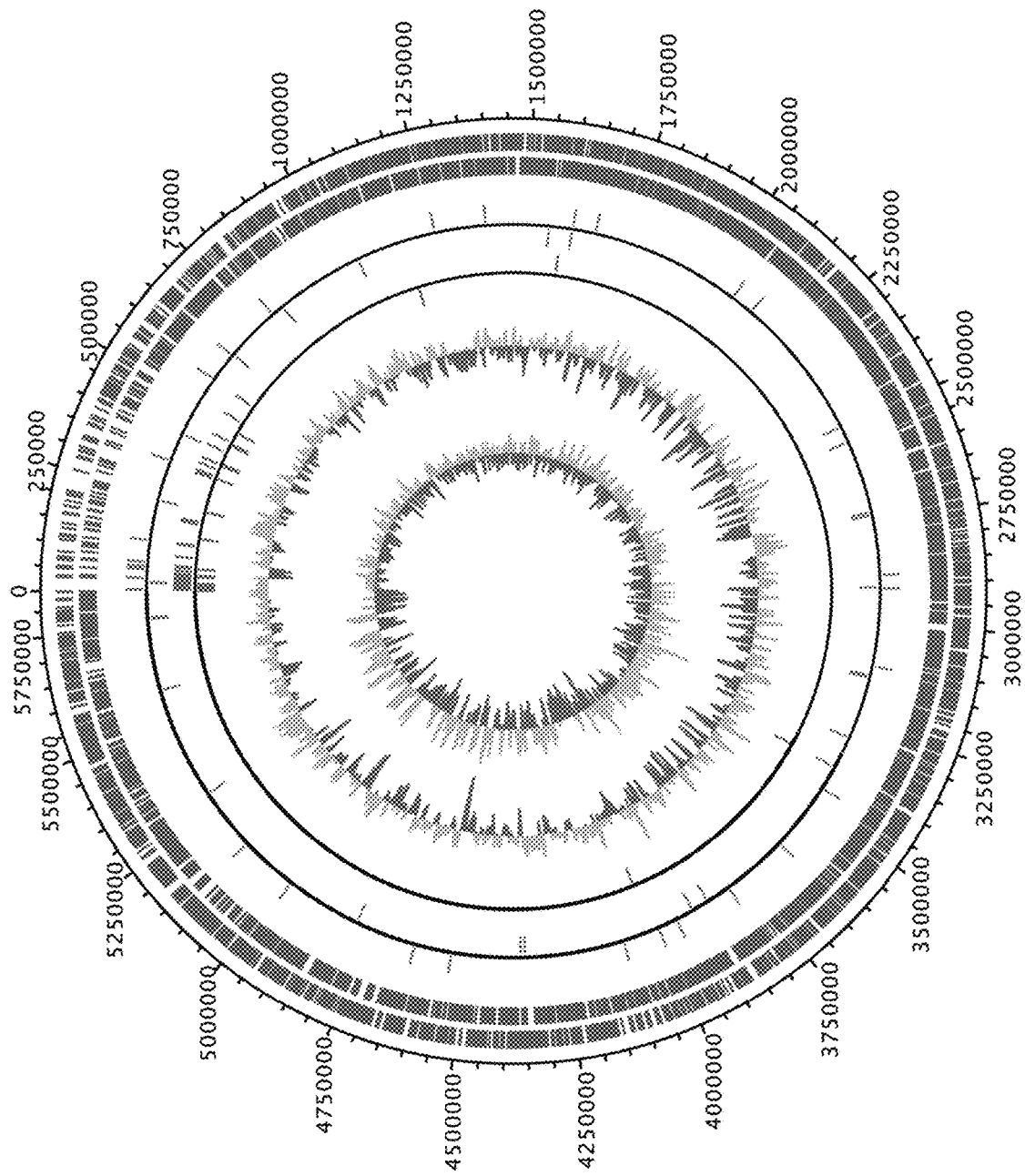
FIG. 15. Whole genome sequencing of CP1. (a) The sequenced CP1 genome was visualized with Artemis DNAPlotter. Tracks from outermost to innermost: forward coding sequence (CDS), reverse CDS, forward and reverse pseudo-CDS (none), forward tRNA, reverse tRNA, forward rRNA, reverse rRNA, forward and reverse repeat regions (none), GC plot, GC skew. (b) Sequence comparison of the CP1 genome with the MG1655 genome, performed with RAST.

Whole genome sequencing revealed that CP1 contains a 5,841,456 base pair genome with 50.9% GC content and 5172 unique coding sequences, 74 unique rRNA sequences, and 95 unique tRNA sequences (FIG. 15a). Further, CP1 is categorized within the B2 phylogenetic group and sequencing type 131 (ST131). However, it is an atypical ST131 E. coli, as it lacks multiple consensus virulence genes: papA (subunit of the Pap fimbrial major pili, present in 95% of ST131), kpsM II (group 2 capsule polysialic acid transport protein, present in 93% of ST131), and iutA (ferric aerobactin receptor, present in 93% of ST131).

Figure 15B:
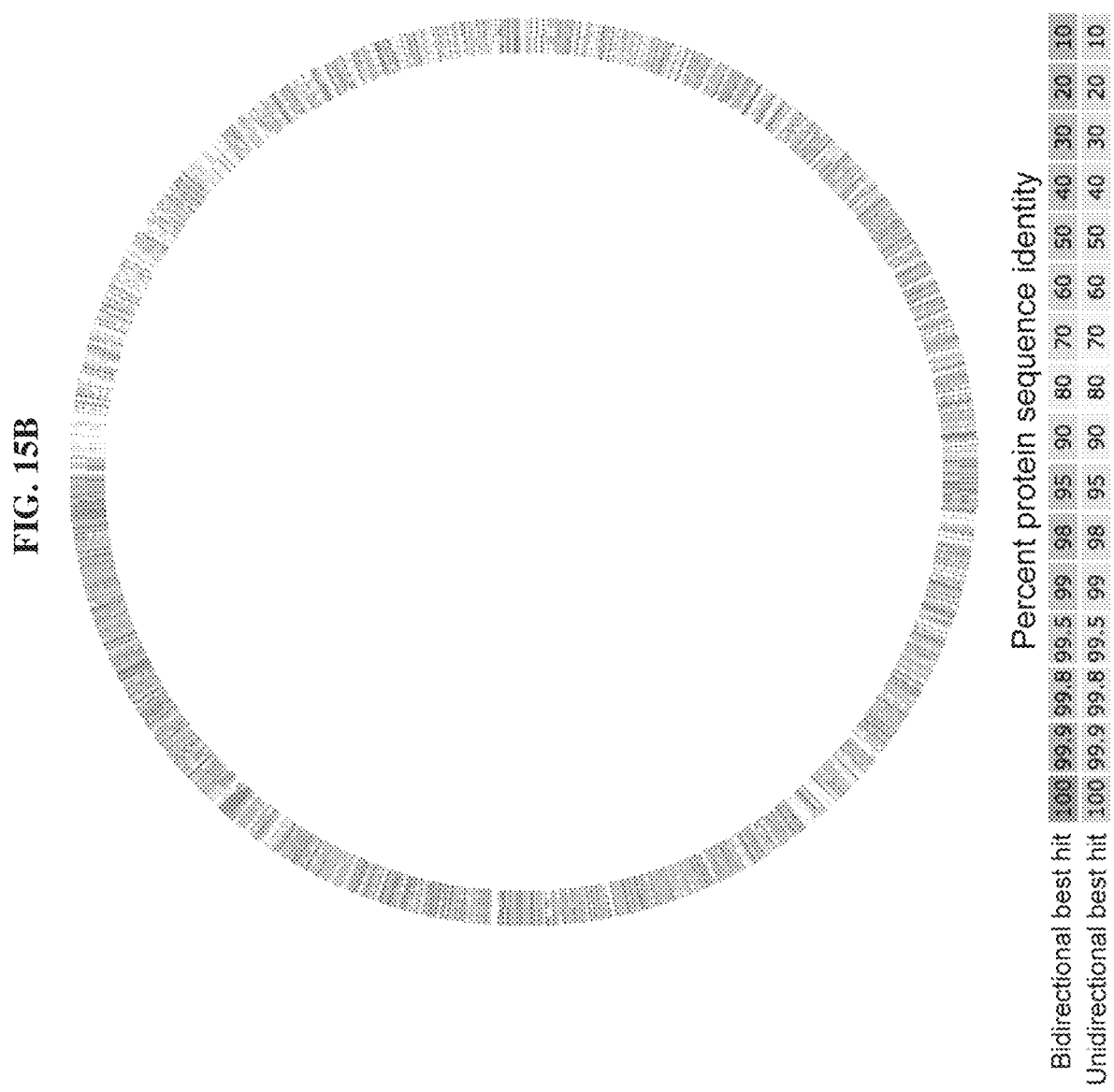
Figure 16:
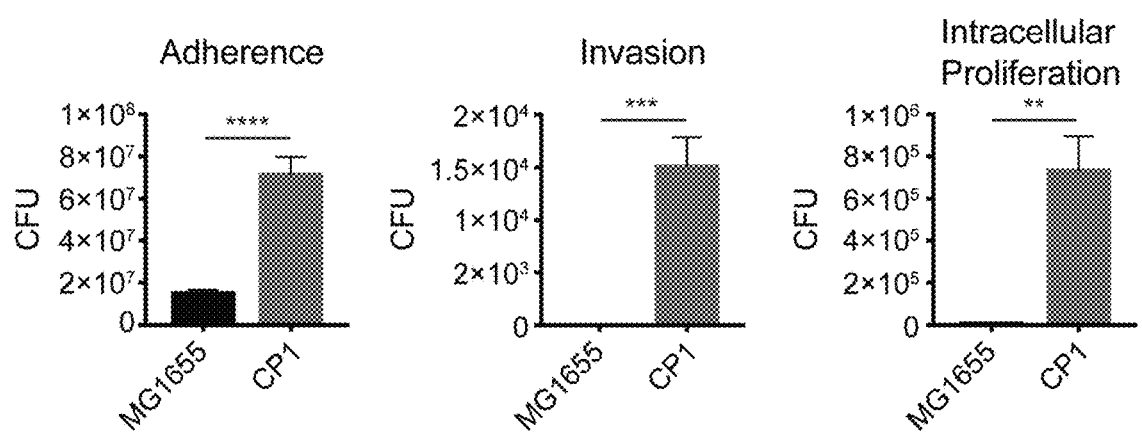
FIG. 16. CP1 adheres to, invades, and intracellularly proliferates within prostate cancer cells. (a) Gentamicin protection assay with CP1 and MG1655 with Myc-CaP cells in vitro, performed in sextuplicates, plated in serial dilutions. Data represented as mean S.E.M. Statistical significance was determined by Student's t-test.  P<0.01, * P<0.001, **** P<0.0001.

UPECs are able to colonize the urinary tract and invade and proliferate within host epithelial cells, and prior analysis of CP1 demonstrated that it is able to adhere to and invade benign prostate epithelial cell lines. To test if CP1 could invade prostate cancer cells, an in vitro gentamicin protection assay was performed with the MYC-driven murine prostate cancer cell line, Myc-CaP. As a control, MG1655 was used, the prototypical strain of the patient-derived K-12 E. coli isolate that has been maintained with "minimal genetic manipulation" and whose complete genome has been sequenced. 19.7% of the genes in CP1 were not present in the MG1655 genome, and the remaining shared genes contained an average 93.9% identity (FIG. 15b). As with the benign prostate epithelial cell lines, CP1 was able to adhere to, invade, and intracellularly proliferate within Myc-CaP cells, and did so to a significantly greater degree than MG1655 (FIG. 16).

CP1 Adheres to and Invades Prostate Cancer Cells and Induces Tumor Immunogenic Cell Death and Pro-Inflammatory Cytokine and Chemokine Production CP1 is a uropathogenic E. coli isolated from the prostate-specific secretions of a patient with chronic prostatitis that homes specifically to prostate tissue and induces local Th1-Th17 polarized lymphocytic infiltration. In contrast to most uropathogenic E. coli belonging to the B2 or D phylogenetic groups (89.2%) [Ref. 42; incorporated by reference in its entirety], CP1 falls within group B1, as confirmed by our phylogenetic analysis stratifying 6 prostate-localizing E. coli into group B2 or D in comparison to CP1 being group B1 (data not shown). Group B1 E. coli are often considered commensals, and the rare B1 uropathogens (3.2%) [42] are unique in that they lack many of the virulence factors commonly present in group B2 and D bacteria [43, 44], in agreement with our comparison of virulence factors in CP1 and a B2 E. coli uropathogen.

To first determine if CP1 is able to adhere to and invade the murine prostate cancer cell line, Myc-CaP, an in vitro gentamicin protection assay. CP1 demonstrated the ability to adhere to (FIG. 1A), invade (FIG. 1B), and intracellularly proliferate (FIG. 1C) within these cells. CP1 co-culture with Myc-CaP cells also resulted in increased supernatant LDH levels, indicating cell death (FIG. 1D). To assess whether this was non-immunogenic or immunogenic cell death (ICD) (Ref. 45; incorporated by reference in its entirety) the levels of the three major ICD damage-associated molecular patterns (DAMPs) were analyzed: secreted high mobility group box 1 (HMGB1), secreted ATP, and cell surface calreticulin. All ICD markers were elevated after Myc-CaP exposure to both mitoxantrone and live CP1 (FIG. 1E-G). Heat killed (H.K.) CP1 did not elicit the same response (FIG. 1E-G). These results remained true with human LNCaP prostate cancer cells (FIG. 1H-J). Further, the impact of CP1 exposure on cancer cell-derived cytokine and chemokine production was assessed, and significantly increased levels of IL-9, IL-15, IL-1α, IFNγ, MIP-2, MIP-1β, G-CSF, IL-17, KC, IP-10, and IL-2 was observed (FIG. 1K). In addition, CP1 exposure resulted in significantly decreased levels of VEGF, with IL-6 being the most down-regulated protein (FIG. 1K). Thus, CP1 displayed an ability to invade prostate cancer cells in vitro, leading to induction of ICD and multiple pro-inflammatory tumor-derived cytokines, as well as decreased production of VEGF.

CP1 Colonizes Prostate Tumors, Increases TILs and Infiltration by Other Immune Cell Types, and Induces a Pro-Inflammatory Microenvironment Experiments were conducted during development of embodiments herein to assess the ability of CP1 to colonize tumors and increase immune cell infiltration. To model prostate cancer in a clinically relevant manner, Myc-CaP cells were intra-prostatically injected into immunocompetent mice and orthotopic tumors were allowed to develop before intra-urethral CP1 administration. At 9 days post-infection (d.p.i), bacterial load was quantified from tumors, bladders, kidneys, livers, and spleens. Cultures from CP1 instilled mice demonstrated strong specificity of the bacteria for tumor tissue relative to the other organs (FIG. 2. Ai.), with all tumors containing greater CFUs compared to their respective bladders (FIG. 2Aii), demonstrating the prostate tumor-specificity of CP1 to ascend from the urethra to the bladder to the tumor without progressing to the kidney. Further, 16S levels were significantly higher in tumors of CP1-administered mice (FIG. 2B). Complementing our in vitro findings, in vivo CP1 administration specifically colonized prostate tumor tissue.

Figure 17:
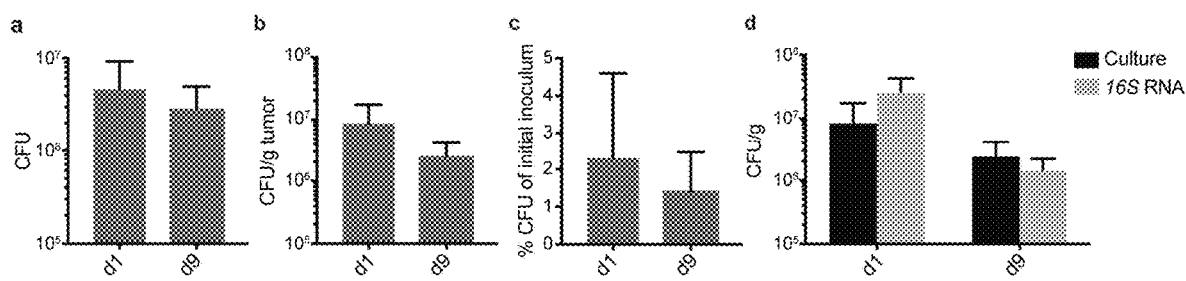
FIG. 17. Intra-tumoral CP1 is culturable and colonization levels remain constant over time. (a) Total bacterial colonization, (b) bacterial colonization normalized to tumor weight, and (c) bacterial colonization as a percentage of the original $2\times10^8$ CP1 inoculum, performed on day 1 (d1) and day 9 (d9) after intra-urethral CP1 administration to orthotopic Myc-CaP prostate tumor-bearing mice. (d) Bacterial colonization as determined by both cultured tumor tissue normalized to tumor weight and 16S RT-PCR calibrated to 16S RT-PCR of titrated CP1 standards and normalized to tumor weight on day 1 and day 9 after CP1 administration. Mice n=4-5/group, tissue cultures plated in serial dilutions, technical duplicates, RT-PCR performed in technical duplicates. Data represented as mean S.E.M. Statistical significance was determined by (a-c) two-tailed Student's t-test, (d) two-way ANOVA.

Additional comparison of CP1 tumor colonization on day 1 and day 9 after intra-urethral administration revealed no significant changes in CFUs over time (FIG. 17a-c).

Figure 10A:
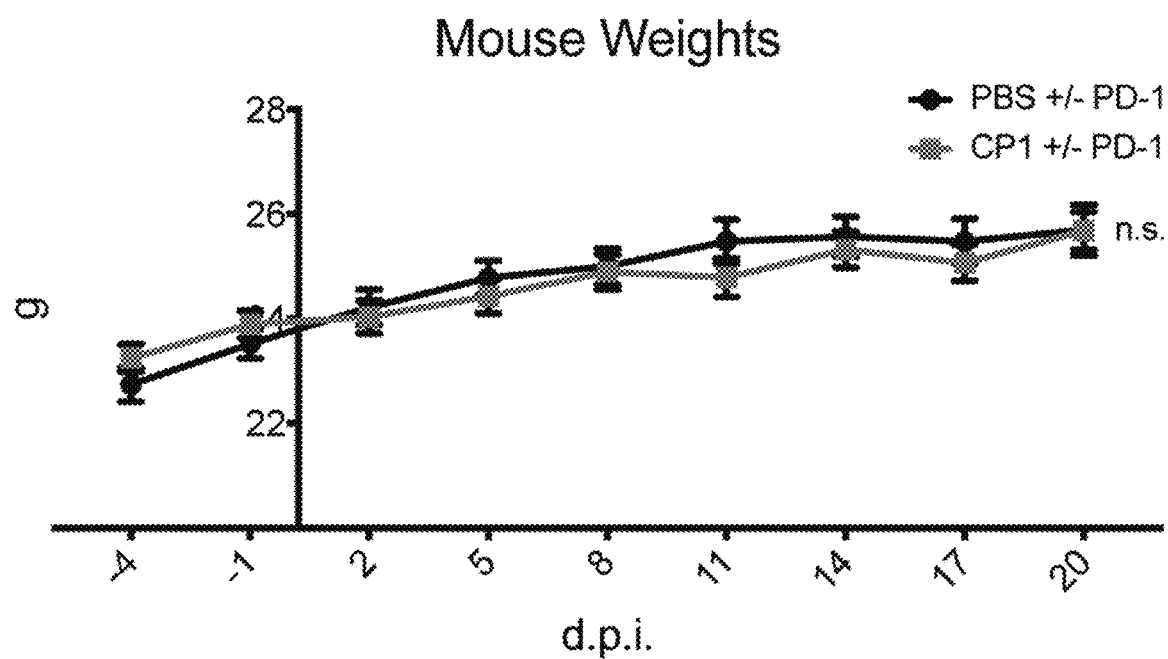
FIGS. 10A-C. CP1 treatment does not cause any systemic toxicities. A) Weights of PBS and CP1 administered mice (±anti-PD-1 antibody), plotted as days post-infection (d.p.i.), n.s.=not significant. B) Chemistry laboratory values of PBS and CP1 administered mice, yellow indicating the normal murine range (ALT=alanine aminotransferase, AST=aspartate aminotransferase, BUN=blood urea nitrogen, TBIL=total bilirubin, $P^-$=phosphorous, $Ca^{2+}$=calcium, $Na^+$=sodium, $K^+$=potassium, $Cl^-$=chloride, ALP=alkaline phosphatase, GGT=gamma glutamyl transferase), n=4-5 mice/experimental group. C) Complete blood count (CBC) values of CP1 administered mice, yellow indicating the normal murine range (RBC=red blood cell, HBG=hemoglobin, HCT=hematocrit, MCV=mean corpuscular volume, MCH=mean corpuscular hemoglobin, MCHC=mean corpuscular hemoglobin concentration, RDW=RBC distribution width, PLT=platelet count, MPV=mean platelet volume), n=3 mice.
Figure 10B:
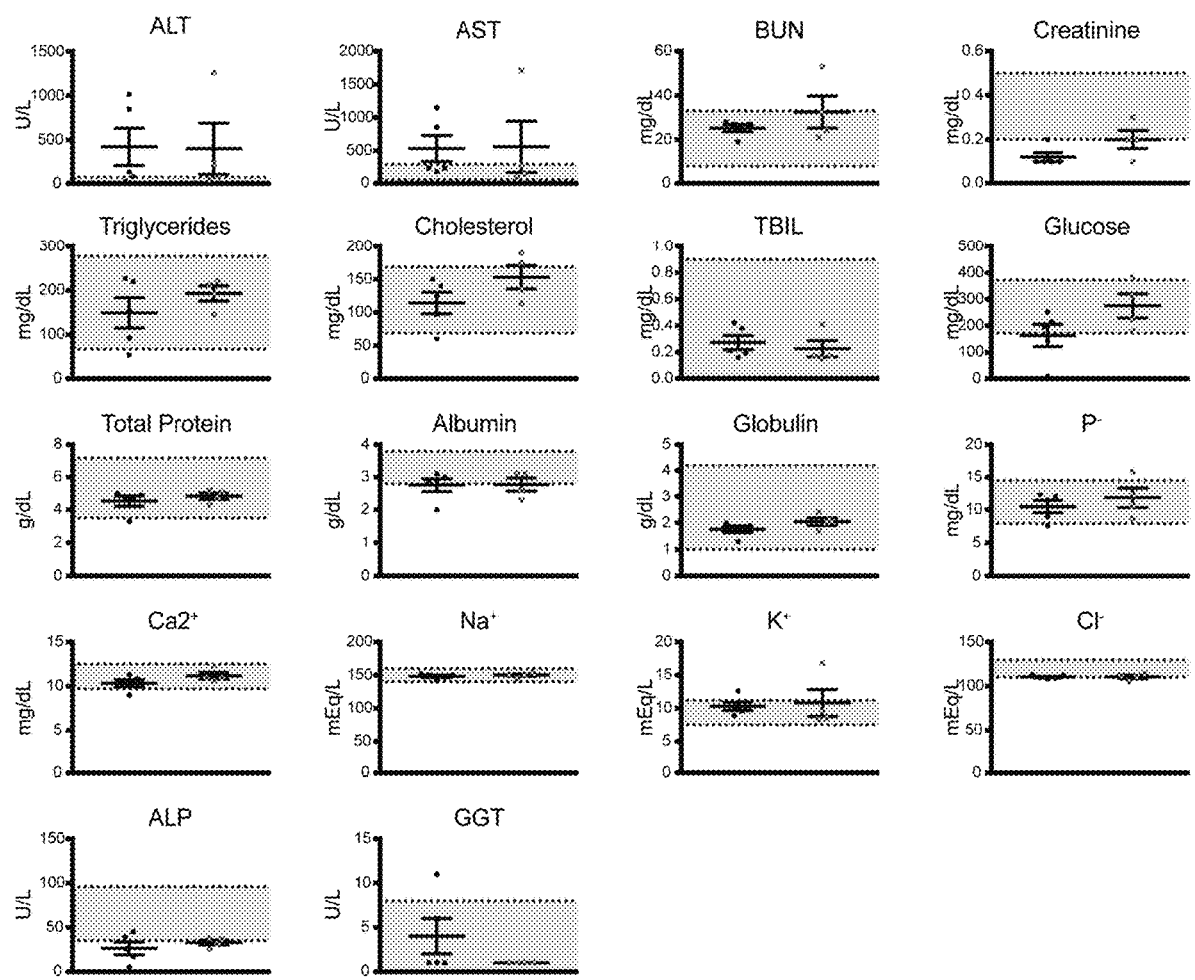
Figure 10C:
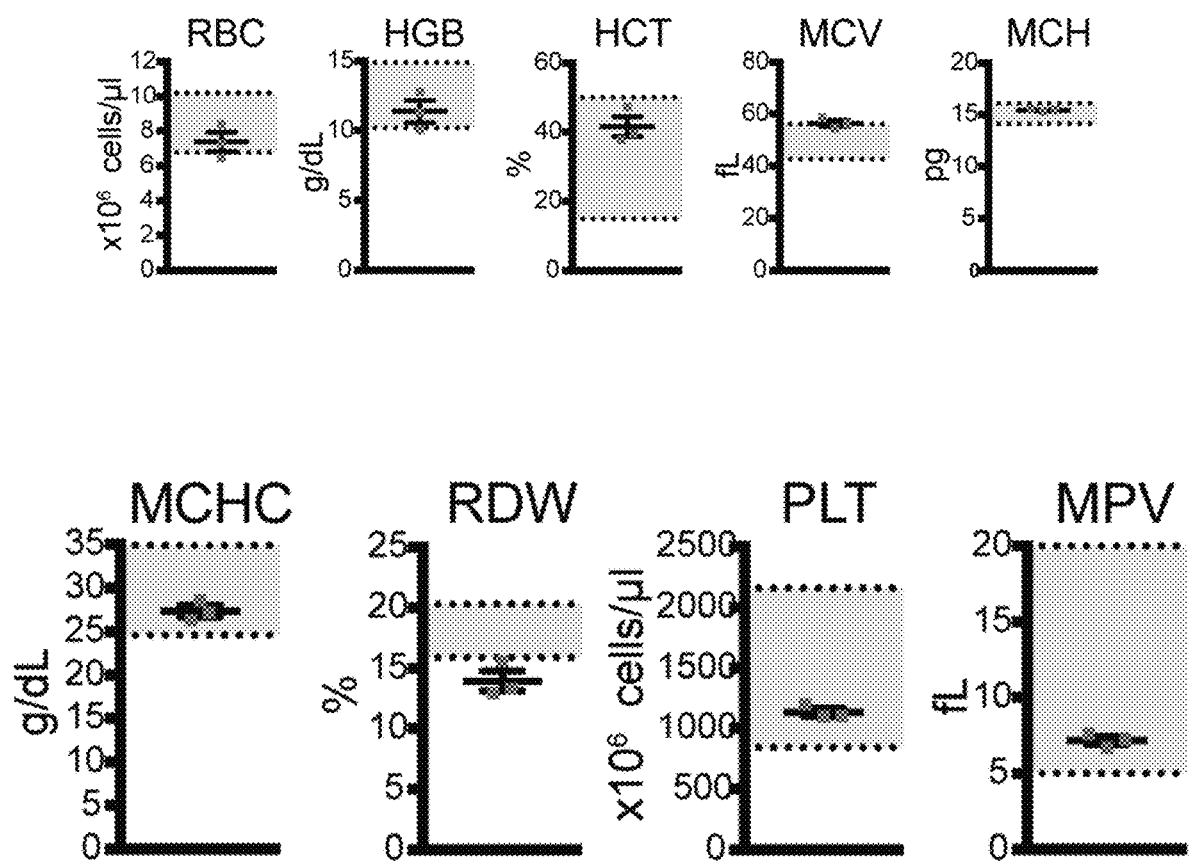
Figure 11A:
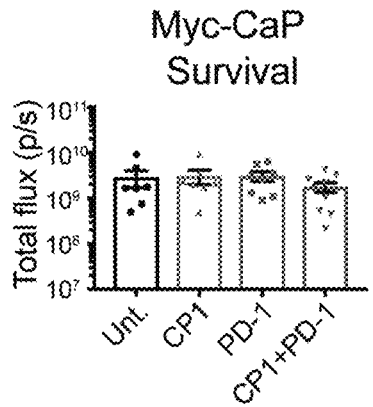
FIGS. 11A-E. Normalization of tumor burden in orthotopic experiments. Pre-treatment tumor IVIS quantification of untreated (unt.), CP1, anti-PD-1, and combination CP1 and anti-PD-1 treated mice in A) Myc-CaP survival (FIG. 4A-C), B) Myc-CaP analysis (FIG. 4B-F), C) Myc-CaP PTEN KO survival (FIG. 5G), Myc-CaP PTEN KO analysis (FIG. 5H, 6, FIG. 13B-F), and of unt., FTY720, combination CP1 and anti-PD-1, and combination CP1 and anti-PD-1 and FTY720 treated mice (FIG. 7).
Figure 11B:
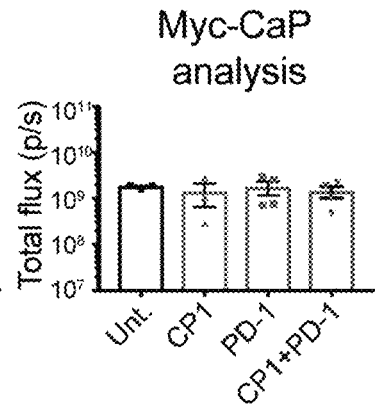
Figure 11C:
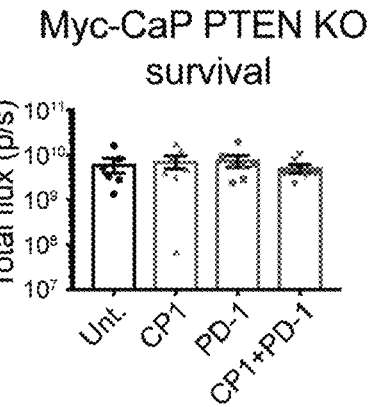
Figure 11D:
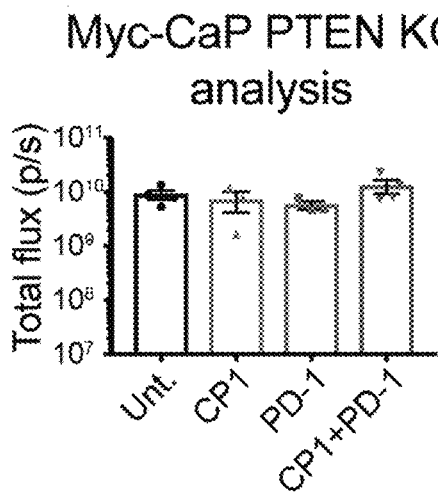
Figure 11E:
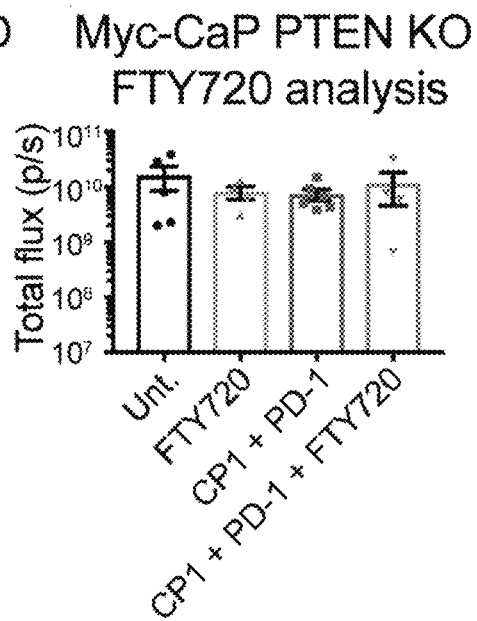

CP1 administration did not result in any systemic toxicities. Mouse weights did not differ with or without CP1 administration over time (FIG. 10A). Additionally, all serum chemistry laboratory values (renal: BUN, creatinine; liver: ALT, AST, ALP, TBIL, total protein, albumin, globulin, GGT; lipid profile: triglycerides, cholesterol; glucose; electrolytes: $Ca^{2+}$, $Na^+$, $K^+$, $Cl^-$, $P^-$) fell within the normal range or displayed no difference between CP1 or PBS instilled mice, signifying that CP1 did not induce any systemic toxicities (FIG. 10B). All CBC values (RBC, HGB, HCT, MCV, MCH, MCHC, PLT, MPV) were also within their normal range after CP1 administration (FIG. 10C), other than low RDW, which is clinically insignificant in the context of otherwise normal values and absence of anemia.

Within these tumors, CP1 administration led to increased T cell infiltration in the stroma and periphery of the tumor (FIG. 2D, F) and even more significantly within the tumor (FIG. 2E, F). As determined by flow cytometry, increased CD3 TILs (FIG. 2G) comprised of both CD8 (FIG. 2H) and CD4 (FIG. 2I) T cells. Experiments conducted during development of embodiments herein to assess whether CP1 induced differential cytokine and chemokine levels within the tumor microenvironment. The most upregulated cytokines and chemokines in CP1-administered tumors were IL-5, TNFα, MIG, IL-4, IFNγ, RANTES, and IL-15, with IL-6 and VEGF showing the greatest decreases (FIG. 2J). IFNγ was the only protein within the top 5 most upregulated cytokines in both the in vitro and in vivo assays, while IL-6, VEGF, and MCP-1 were all within the 5 most downregulated molecules in both assays.

Figure 18:
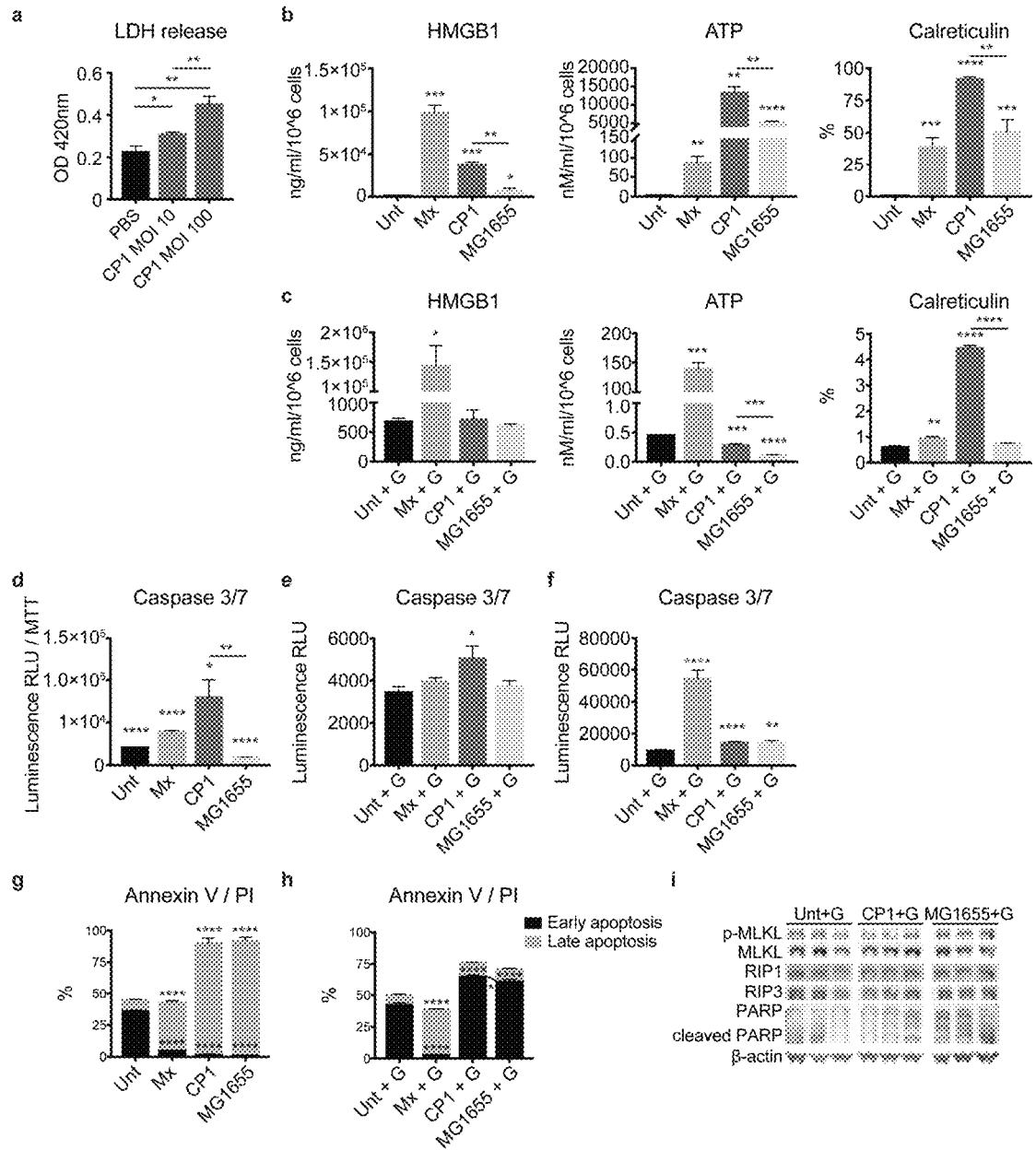
FIG. 18. CP1 induces ICD and select cell death markers, with and without gentamicin, and to a greater degree than MG1655. (a) LDH level, as a measure of cell death, from CP1 and Myc-CaP co-culture, performed in triplicates. (b-i) Myc-CaP cell were co-cultured with Mx, CP1 (MOI 1), or MG1655 (MOI 1) (b, d, g) in normal media or (c, e, f, h, i) with gentamicin (+G) added after 2 hours. (b, c) ICD was measured via HMGB1 (ELISA, 72 hours), ATP (luminescence assay, 72 hours), and calreticulin (flow cytometry, 24 or 72 hours), performed in biological triplicates, technical duplicates. (d-f) Caspase 3/7 activity (luminescence assay) was measured at (d, e) 6 hours or (f) 24 hours, (d) normalized to cell count (MTT assay), performed in sextuplicates. (g, h) Early stage apoptosis (Annexin $V^+$ $PI^-$) and late stage apoptosis (Annexin $V^+$ $PI^+$) were determined by flow cytometry after 24 hours, performed in triplicates. (i) Western blot analysis of phosphorylated and total MLKL, RIP1, RIP3, full length and cleaved PARP, and 3-actin after 24 hours, performed in triplicates. Data represented as mean S.E.M. Statistical significance was determined by two-tailed Student's t-test (each group compared to Unt, and CP1 compared to MG1655). * P<0.05,  P<0.01, * P<0.001, **** P<0.0001.

In vitro culture of Myc-CaP cells with CP1 resulted in cancer cell death in a dose-dependent manner (FIG. 18a). Therefore, experiments were conducted during development of embodiments herein to analyze whether this was specifically immunogenic cell death (ICD). All three major ICD damage-associated molecular patterns (DAMPs): HMGB1, ATP, and calreticulin, were elevated in the presence of live, but not heat killed, CP1. Similar results were seen with human LNCaP prostate cancer cells. CP1 also induced all ICD markers to a significantly higher level than did MG1655 (FIG. 18b). To more accurately represent the quantity of CP1 present within the tumor, the in vitro ICD assays were repeated with the addition of gentamicin at a multiplicity of infection (MOI) of 1. These conditions resulted in a final average CPL:Myc-CaP ratio of 0.005, with the surviving intracellular CP1 representing approximately 10.9% of the initial bacteria added to the culture (multiple orders of magnitude less bacteria than without gentamicin). In the presence of gentamicin, CP1 did not induce HMGB1 or ATP secretion, but did significantly increase the percent of calreticulin$^+$ Myc-CaP cells (FIG. 18c). However, it is important to note that in addition to decreasing total CP1 count, gentamicin also eliminated any potential importance of extracellular CP1 interacting with tumor cells or CP1 spreading between cells.

Figure 14A:
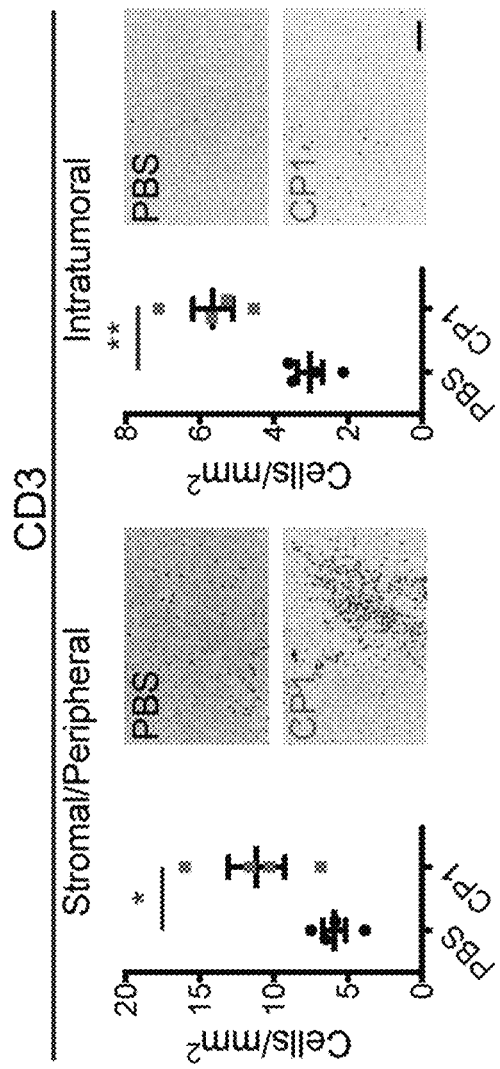
FIG. 14. CP1 increases TILs and tumor immune infiltration while decreasing Tregs. (a) Blinded IHC with representative images (scale bar, 100 m) and (b-m) flow cytometry analysis of Myc-CaP tumors or dLNs, as indicated, displayed as cell counts normalized to tumor volume (scatter plots) or percentages of parent gate (scatter boxed plots), with representative flow cytometry plots. MDSCs were defined as $CD11b^+Gr-1^+$. (n) Multiplex cytokine and chemokine array from Myc-CaP tumors. Mice n=4-5/group, performed in 2 independent experiments. Data represented as mean S.E.M. or log 2 fold change with and without CP1 administration. Statistical significance was determined by two-tailed Student's t-test. * P<0.05,  P<0.01, * P<0.001.
Figure 14B:
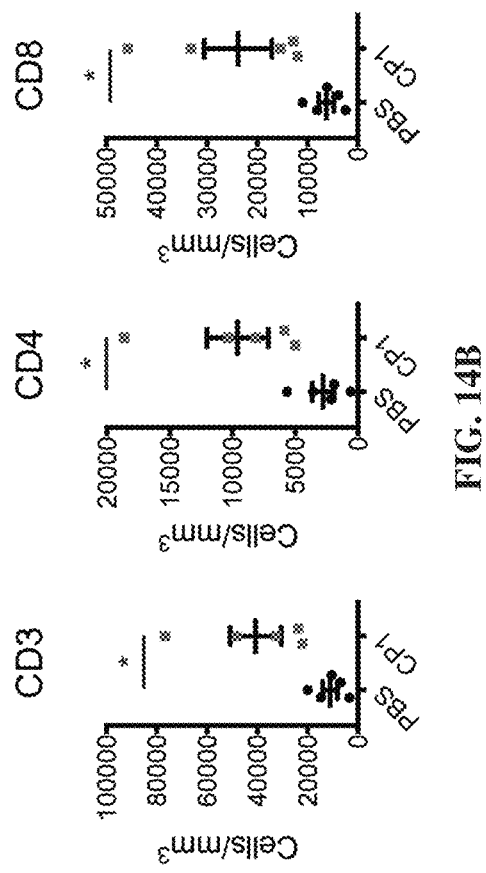
Figures 14H, 14I:
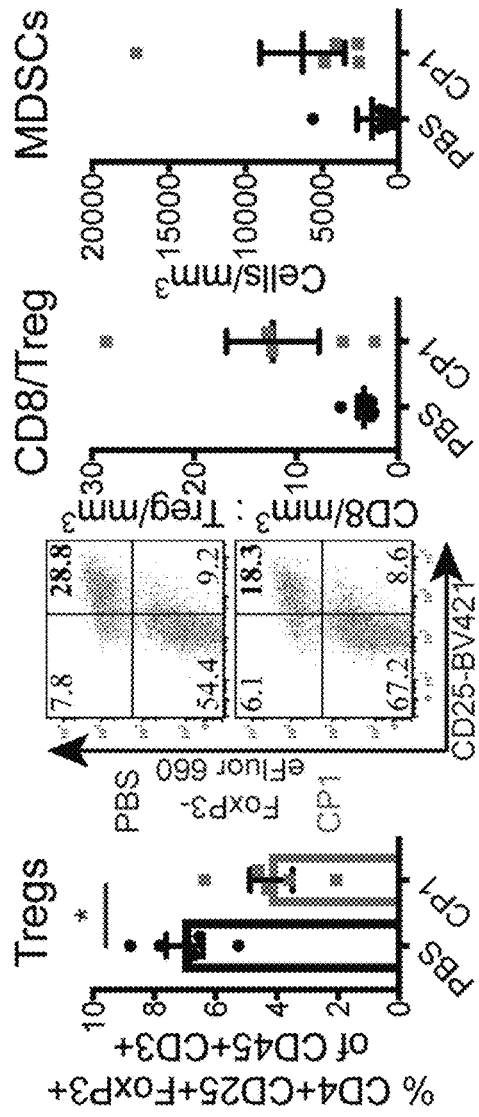
Figures 14J, 14K:
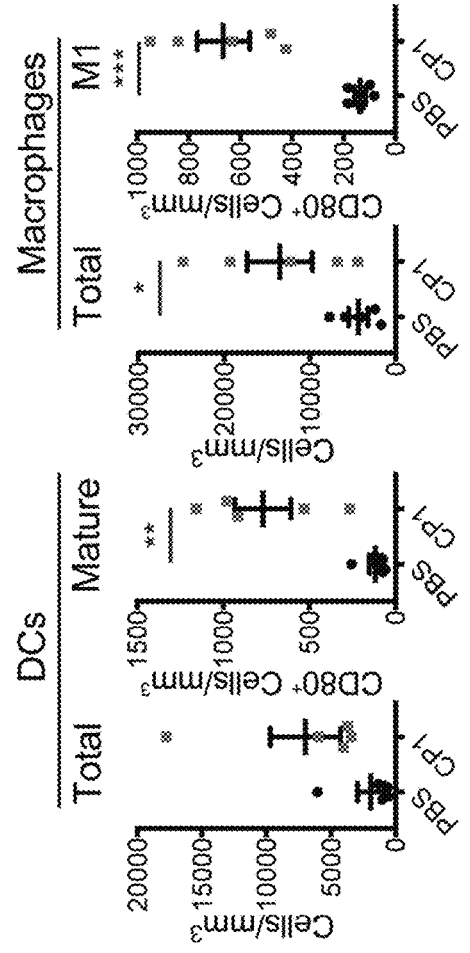
Figure 19:
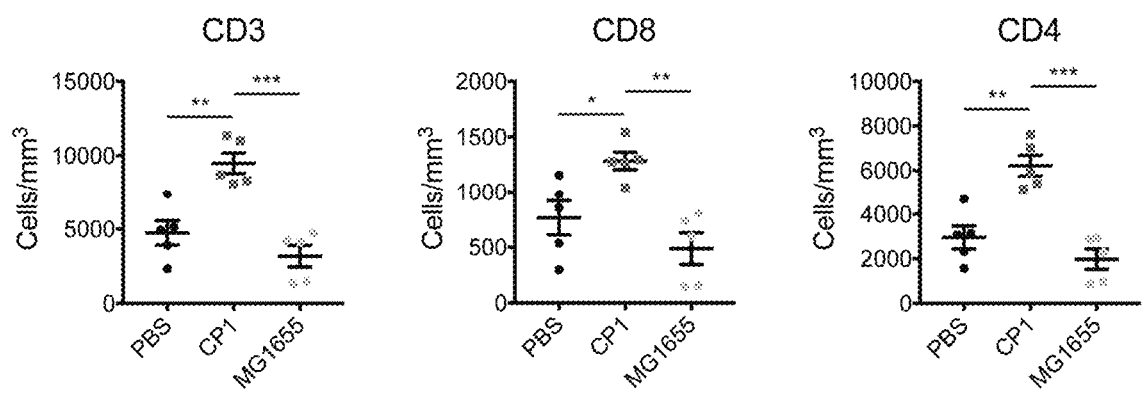
FIG. 19. Intra-urethrally administered MG1655 does not increase prostatic TILs. Flow cytometry analysis of orthotopic Myc-CaP tumors 9 days after intra-urethral administration of PBS, CP1, or MG1655, displayed as cell counts normalized to tumor volume. Mice n=5. Data represented as mean S.E.M. Statistical significance was determined by two-tailed Student's t-test. * P<0.05,  P<0.01, * P<0.001.
Figure 20:
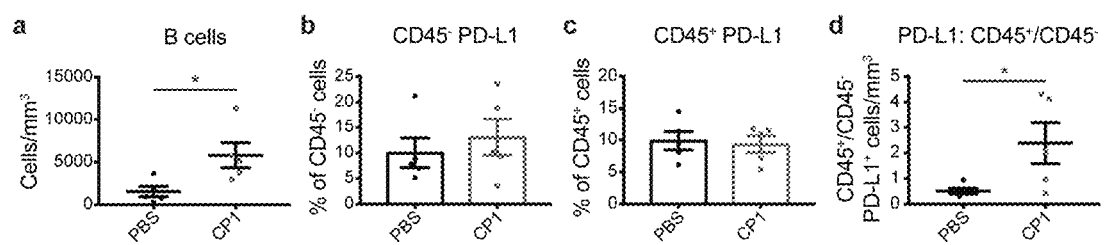
FIG. 20. CP1 increases B cells and does not increase PD-L1 expression. Flow cytometry analysis of (a) B cells, and PD-L1 on (b) CD45⁻ and (c) CD45⁺ intra-tumoral cells, and (d) the ratio of CD45⁺PD-L1⁺/CD45⁻PD-L1⁺ cell densities. n=4-5 mice/experimental group, performed in 2 independent experiments. Data represented as mean S.E.M. as cell counts normalized to tumor volume (scatter plots) or percentages of parent gate (scatter boxed plots). Statistical significance was determined by two-tailed Student's t-test. * P<0.05.

CP1 increases tumor T cell infiltration and reprograms the prostate tumor microenvironment. To evaluate CP1's ability to remodel the "cold" prostate tumor microenvironment, tumors were immunophenotyped 9 days after intra-urethral bacterial administration. CP1 increased T cells not only in the tumor stroma and periphery, but also intra-tumorally (FIG. 14a), consisting of both CD4 and CD8 tumor infiltrating lymphocytes (TILs) (FIG. 14b). In contrast, intra-urethral MG1655 administration did not result in increased CD4 or CD8 TILs (FIG. 19). Further analysis revealed that the increased CD8 TILs in CP1-administered tumors expressed increased TNFα (FIG. 14c) and the activation marker PD-1 (FIG. 14d), and a higher percentage expressed IFNγ within the tumor draining lymph nodes (dLNs) (FIG. 14e). Intra-tumoral (FIG. 14f) and dLN (FIG. 14g) CD4 T cells were Th17-polarized. CP1 administration also decreased the percentage of regulatory T cell (Treg) TILs, with most tumors containing a >3-fold increased CD8/Treg ratio (FIG. 14h). Despite increasing overall hematopoietic infiltration, CP1 did not increase infiltration of myeloid-derived suppressor cells (MDSCs; CD11b$^+$Gr-1$^+$) (FIG. 14i). CP1 significantly increased both mature dendritic cells (DCs) and M1-polarized macrophages to a much greater degree than either total cell type (FIGS. 14j, 14k), while also increasing infiltration of NK cells (FIG. 14l), γδ T cells (FIG. 14m), and B cells (FIG. 20a). While CP1 did not increase PD-L1 on tumor or hematopoietic cells, the immune compartment was a greater source of PD-L1 within these tumors due to increased overall CD45$^+$ infiltration (FIG. 20b-d). IL-5 and TNFα were the most upregulated cytokines in CP1-treated tumors, and, consistent with the in vitro cytokine/chemokine array, IFNγ was among the most upregulated and IL-6 and VEGF among the most downregulated proteins after CP1 administration (FIG. 14n). Overall, intra-tumoral CP1 increased infiltration of multiple anti-tumor immune cell types while decreasing Tregs.

Figure 3A:
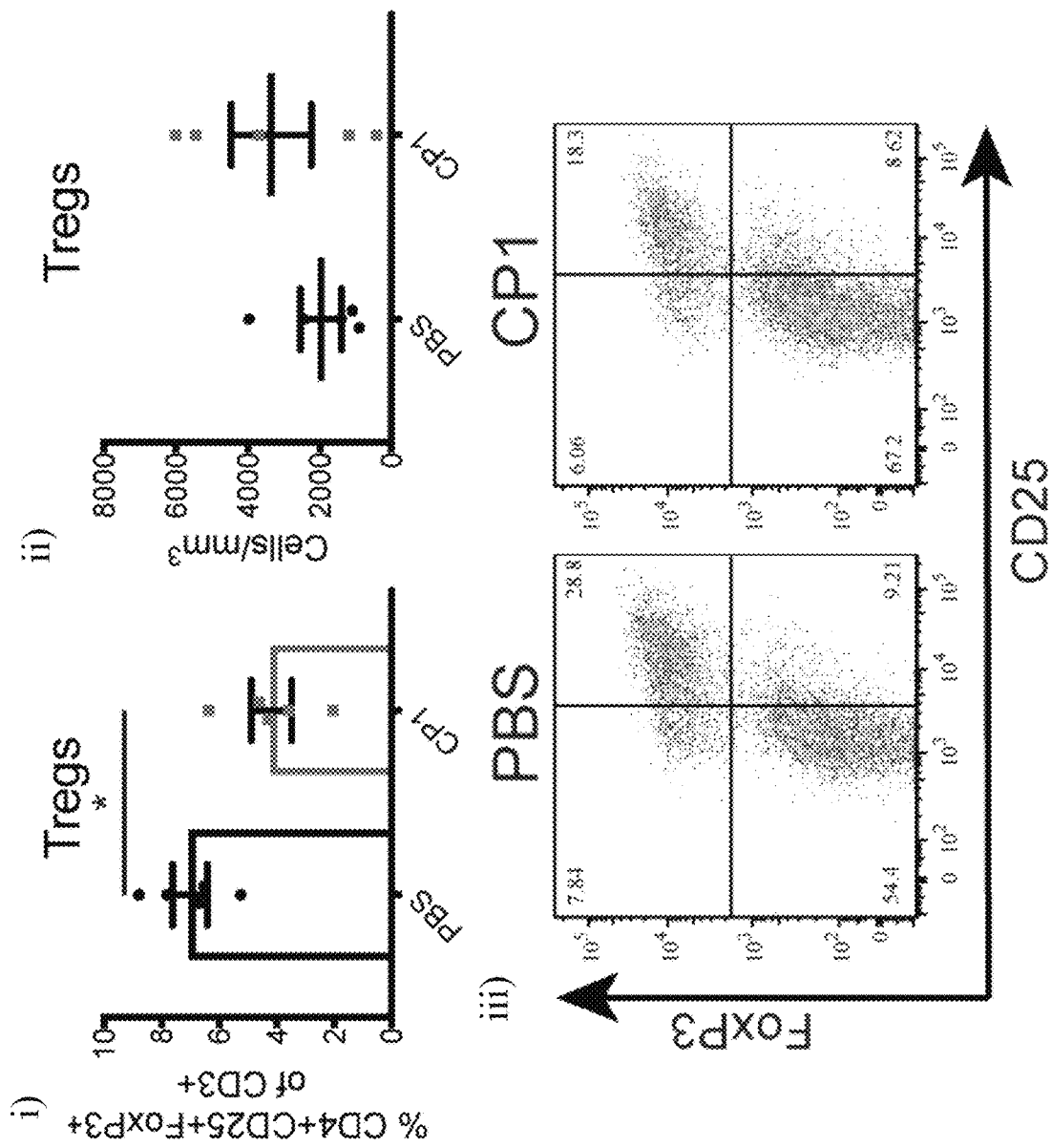
FIGS. 3A-P. CP1 augments the anti-tumor immune microenvironment, skewing toward a pro-inflammatory phenotype and against an immunosuppressive phenotype. Flow cytometry analysis of intra-tumoral (cell counts normalized to tumor volume represented as scatter plots, cell phenotype percentages represented as boxed scatter plots) of Ai-iii) Tregs, B) MDSCs, Ci) total and Cii-iii) mature DCs, Di) total and Dii-iii) M1 macrophages, E) γδ T cells, F) NK cells, G) B cells, H) CD4 IFNγ expressing cells, I) CD8 TNF expressing cells, Ji-ii) degradulated CD8 IFNγ expressing cells, Ki-ii) CD4 IL-17a expressing cells, L) dLN CD4 IL-17a expressing cells, M) PD-L1 on non-hematopoietic cells, N) PD-L1 on hematopoietic cells, O) hematopoietic: non-hematopoietic PD-L1 ratio, and P) CD8 PD-1 expressing cells. n=4-5 mice/group, performed in 2 independent experiments.
Figure 3B:
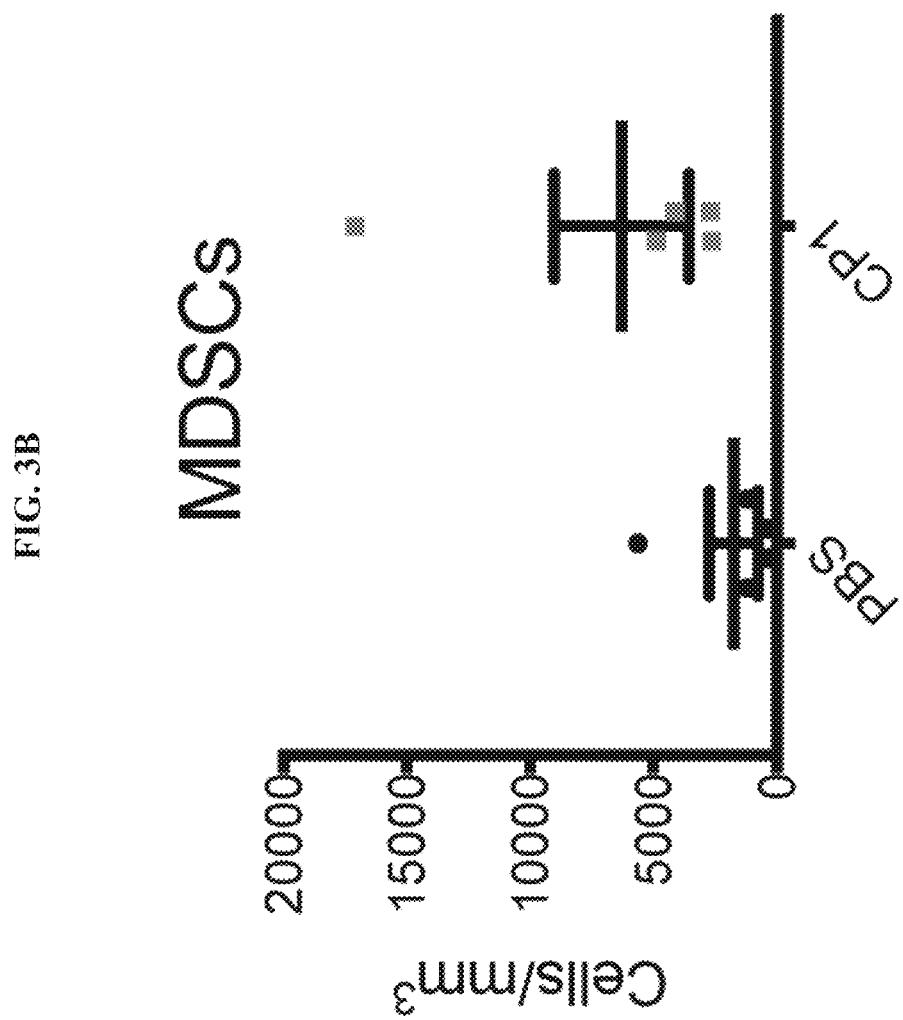
Figures 3C, 3D:
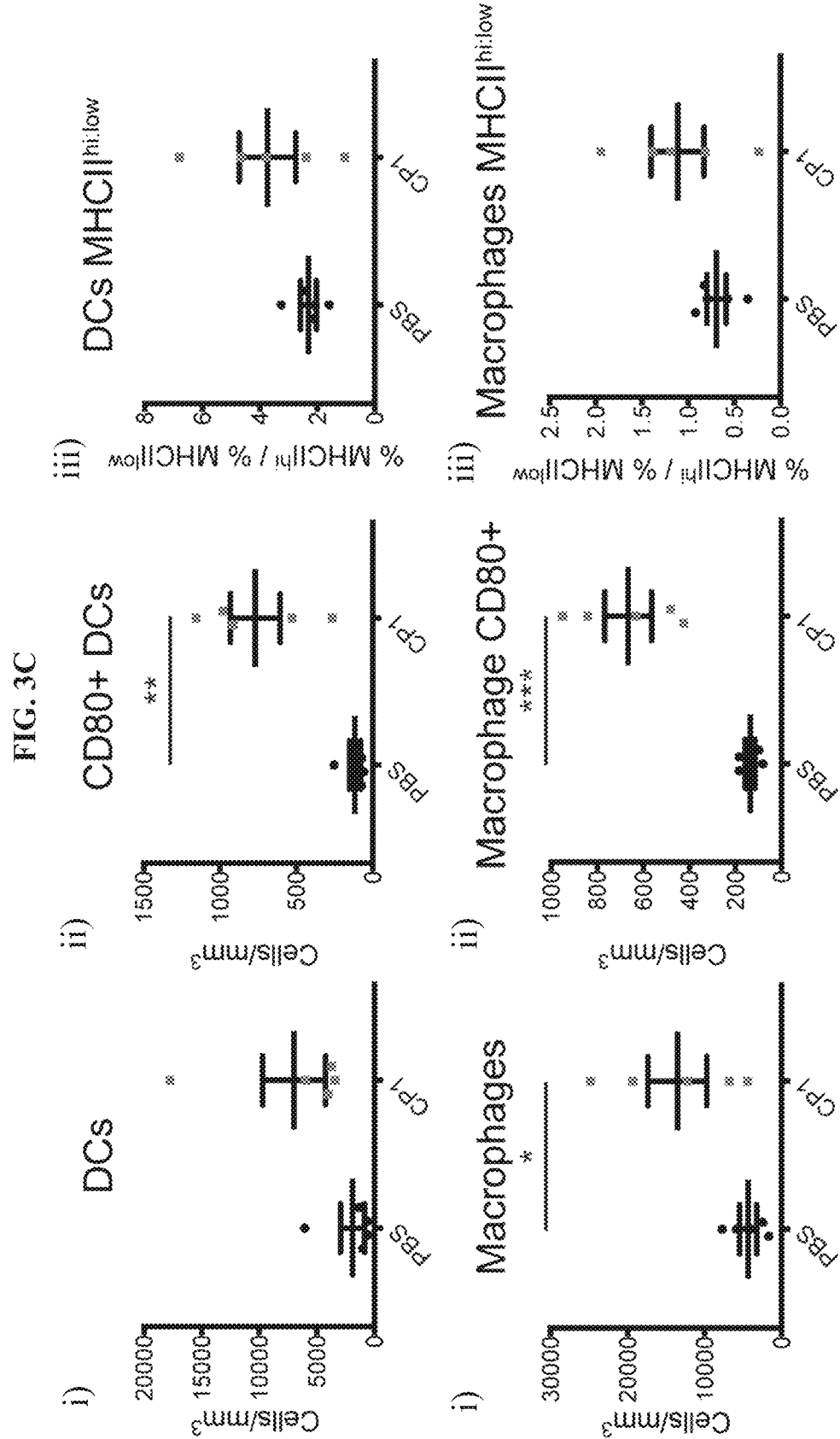
Figure 3J:
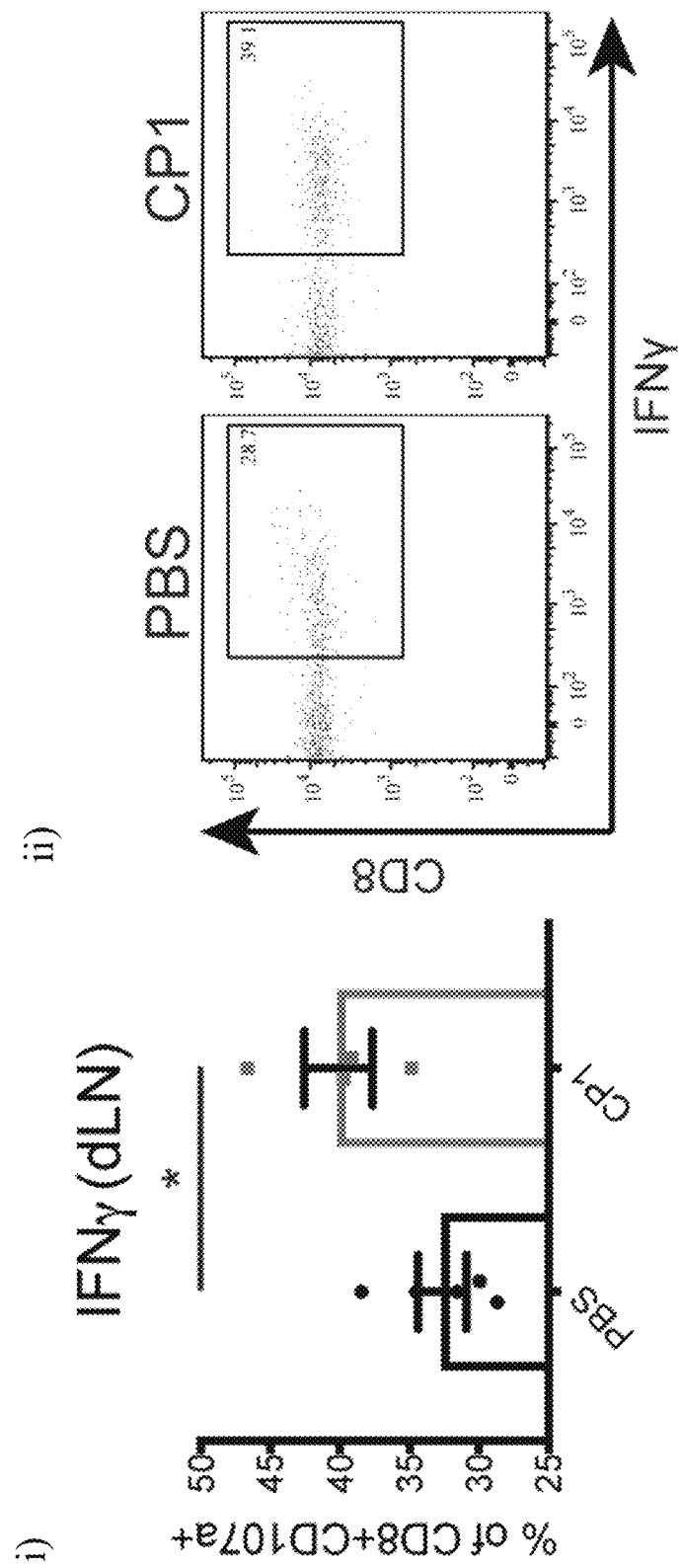
Figure 3K:
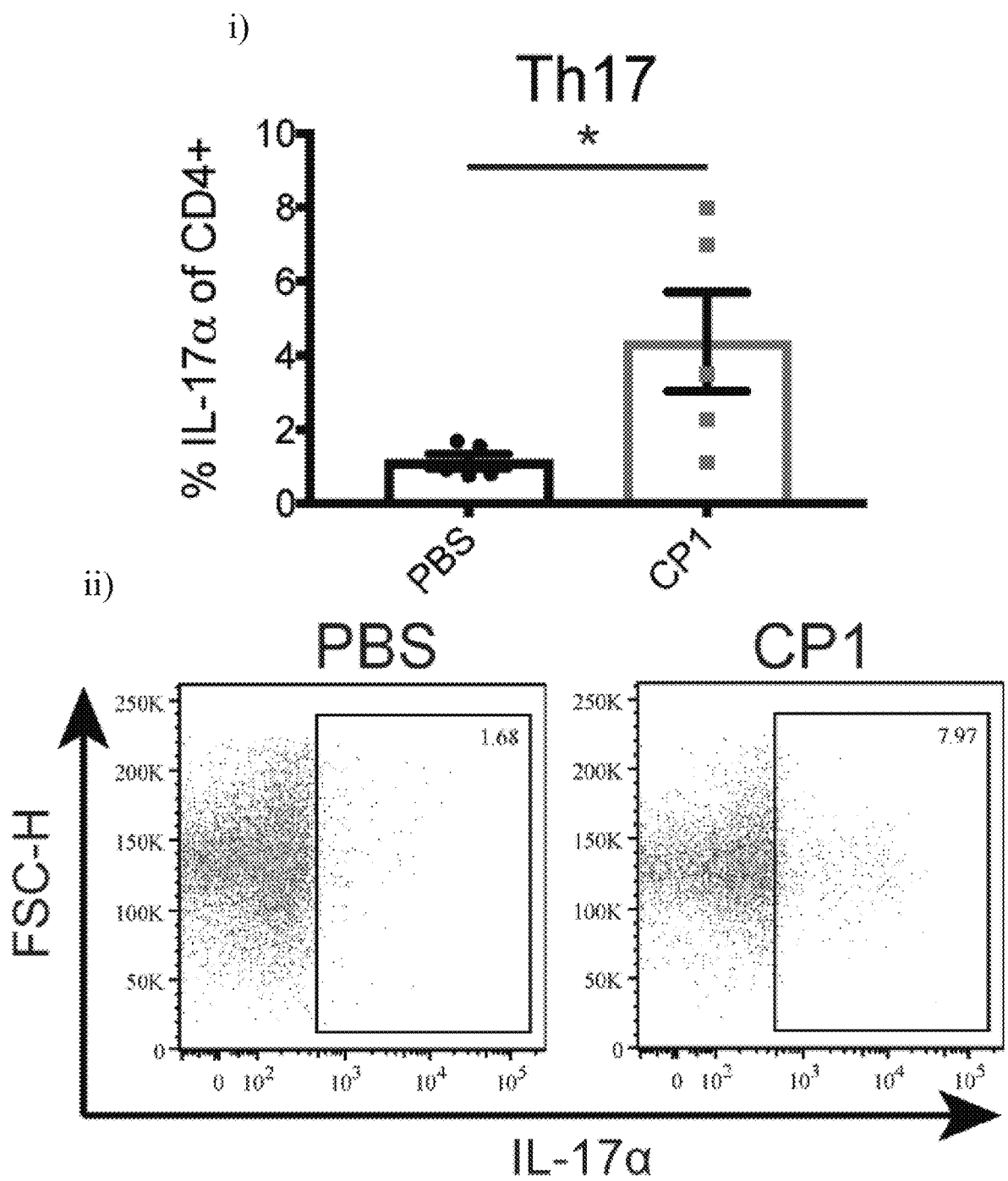
Figure 3L:
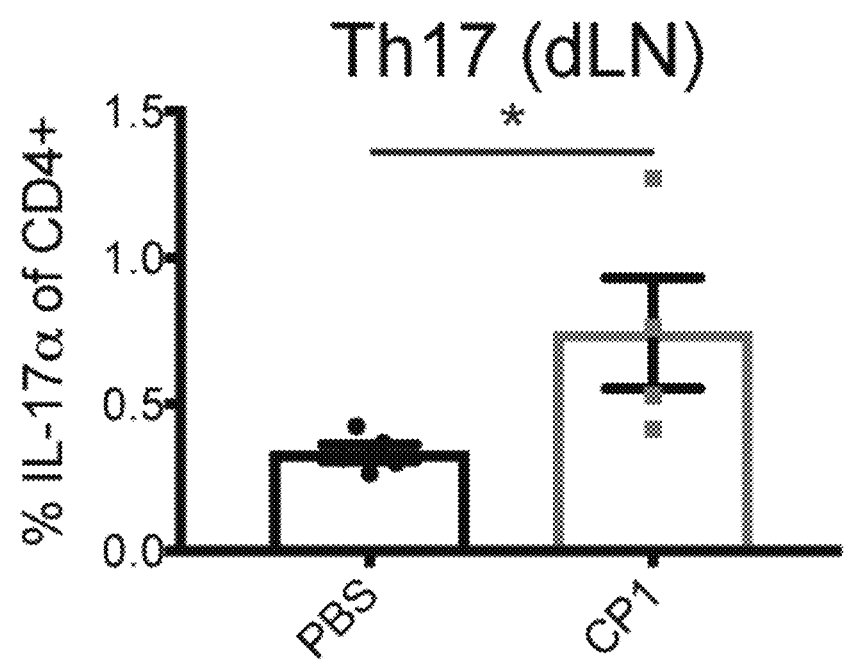

Experiments conducted during development of embodiments herein to further characterize any additional changes in the tumor immunophenotype after CP1 administration. CP1 exposure resulted in a decreased percentage of regulatory T cells (Tregs) comprising total CD3 TTLs (FIG. 3Ai, Aiii), with no change in total Tregs/mm$^3$ (FIG. 3Aii). CP1 also did not increase levels of intra-tumoral myeloid-derived suppressor cells (MDSCs) (FIG. 3B). While CP1 did not significantly increase the level of tumor infiltrating dendritic cells (DCs) (FIG. 3Ci), there was a highly significant increase in mature CD80+ DCs within these tumors (FIG. 3Cii), as well as a trending increase toward a CD11c MHCII$^{hi}$ phenotype (FIG. 3Ciii; p<0.05 without low MHCII$^{hi}$/MHCII$^{hi}$ outlier). Similarly, CP1 highly significantly increased the density of CD80+ tumor-associated macrophages (TAMs) (FIG. 3Dii) to a much greater degree than overall TAMs (FIG. 3Di), and again led to a trending increase toward a MHCII$^{hi}$ TAM phenotype (FIG. 3Diii; p<0.05 without low MHCII$^{hi}$/MHCII$^{low}$ outlier), both markers of anti-tumor M1 polarized TAMs [47]. In addition, CP1 administration induced increased levels of γδ T cells (FIG. 3E), NK cells (FIG. 3F), and B cells (FIG. 3G). Further, CP1 administered tumors contained a trending increase in Th1 CD4 T cells (FIG. 3H) and a significant increase in TNF-expressing CD8 T cells (FIG. 3I), and degranulated CD8 T cells from draining lymph nodes (dLNs) were significantly polarized towards an IFNγ-expressing phenotype (FIG. Ji-ii). CP1 also significantly skewed CD4 T cells toward a Th17 phenotype within the tumor (FIG. 3Ki-ii) and dLNs (FIG. 3L). Interestingly, CP1 did not increase PD-L1 expression on non-hematopoietic (FIG. 3M) or immune infiltrating cells (FIG. 3N), but due to increased overall immune infiltration, the source of PD-L1 within CP1 administered tumors was significantly more from the immune compartment (FIG. 3O). Additionally, CP1 led to increased levels of PD-1 expressing CD8 TILs (FIG. 3P). Overall, CP1 was able to specifically colonize prostate tumor tissue and induce tumor infiltration by activated CD8 TILs, Th1 and Th17 TILs, mature DCs, M1 TAMs, 76 T cells, NK cells, and B cells, as well as induce a pro-inflammatory cytokine and chemokine profile with increased IFNγ and decreased VEGF, without causing any systemic toxicities.

Figure 4A:
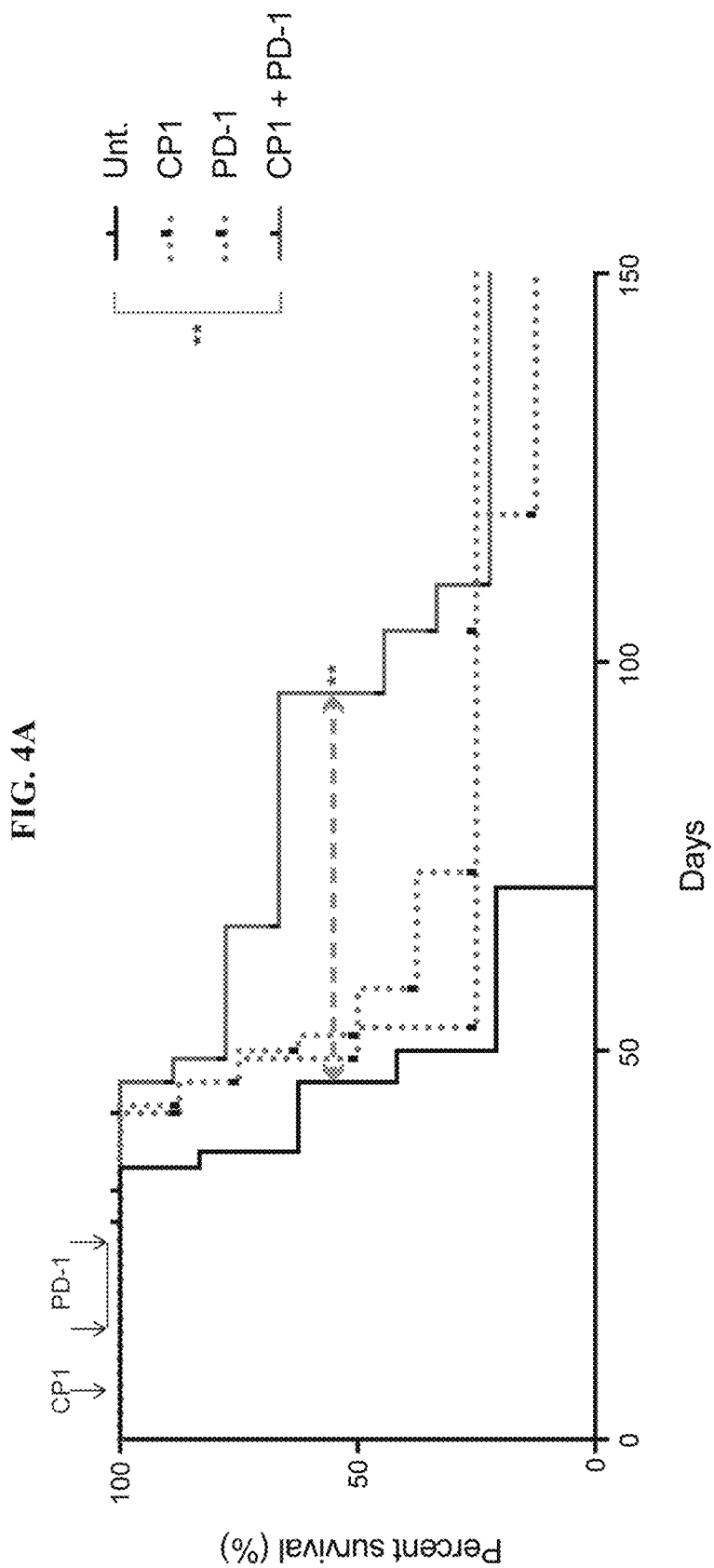
FIGS. 4A-E. Combination CP1 and anti-PD-1 immunotherapy is efficacious in treating orthotopic prostate tumors. A) Survival of untreated (unt.), CP1, anti-PD-1, or combination CP1 and anti-PD-1 treated mice, n=6-12 mice/group. B) Waterfall plot of IVIS imaging quantification of CP1, anti-PD-1, or combination CP1 and anti-PD-1 treated mice, with each bar representing the post-treatment (Tx) total flux (p/s) of a single tumor normalized to both its own pre-treatment total flux and the mean of the post/pre-treatment normalized untreated tumors total flux. Percentages indicate the fraction of tumors with values <0.0001. n=11-17 mice/group C) Representative IVIS images. Post treatment tumor D) volume, as determined by caliper measurements, and E) tumor weights, with F) representative gross images, n=3-4 mice/group.
Figure 4B:
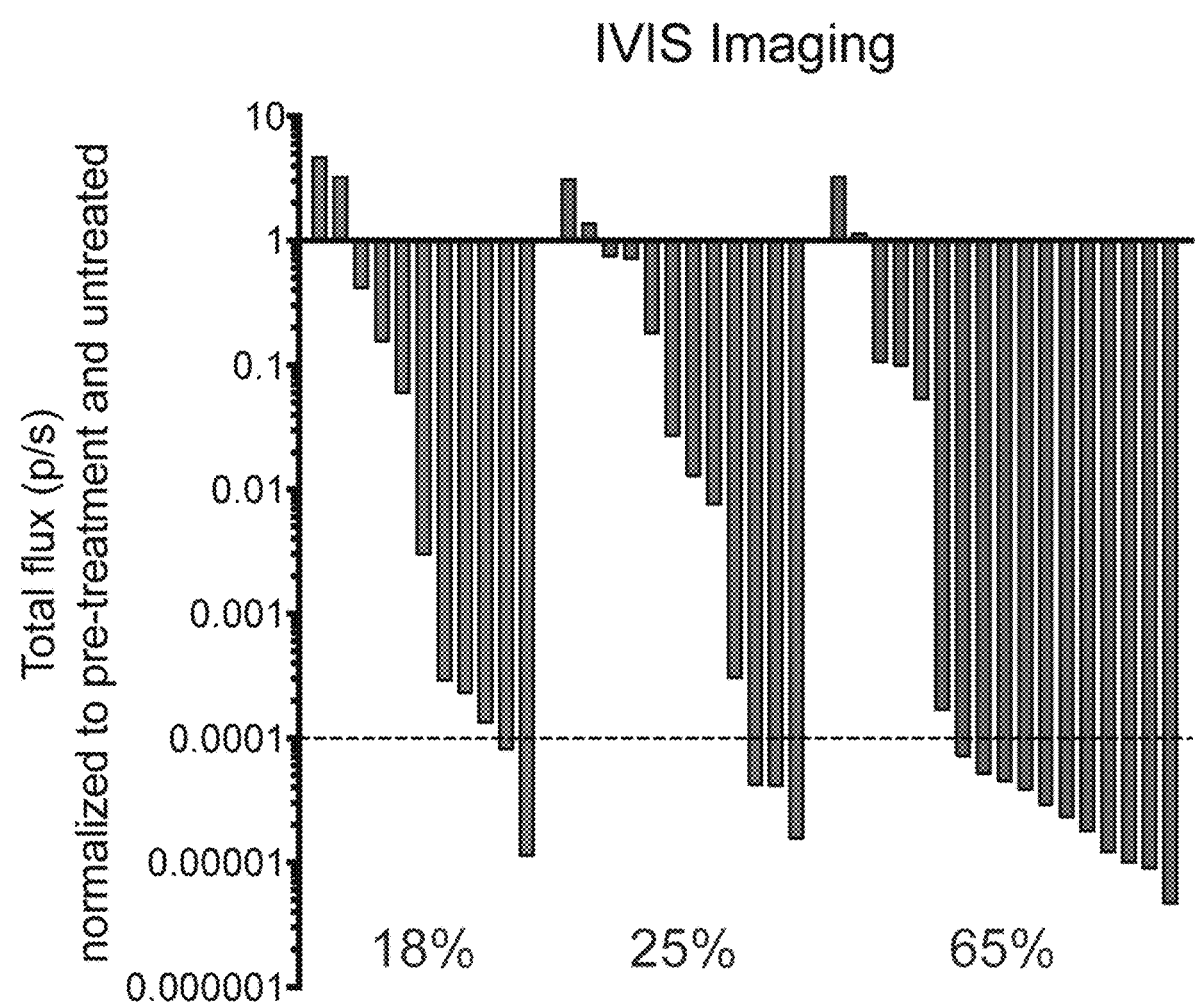
Figure 4C:
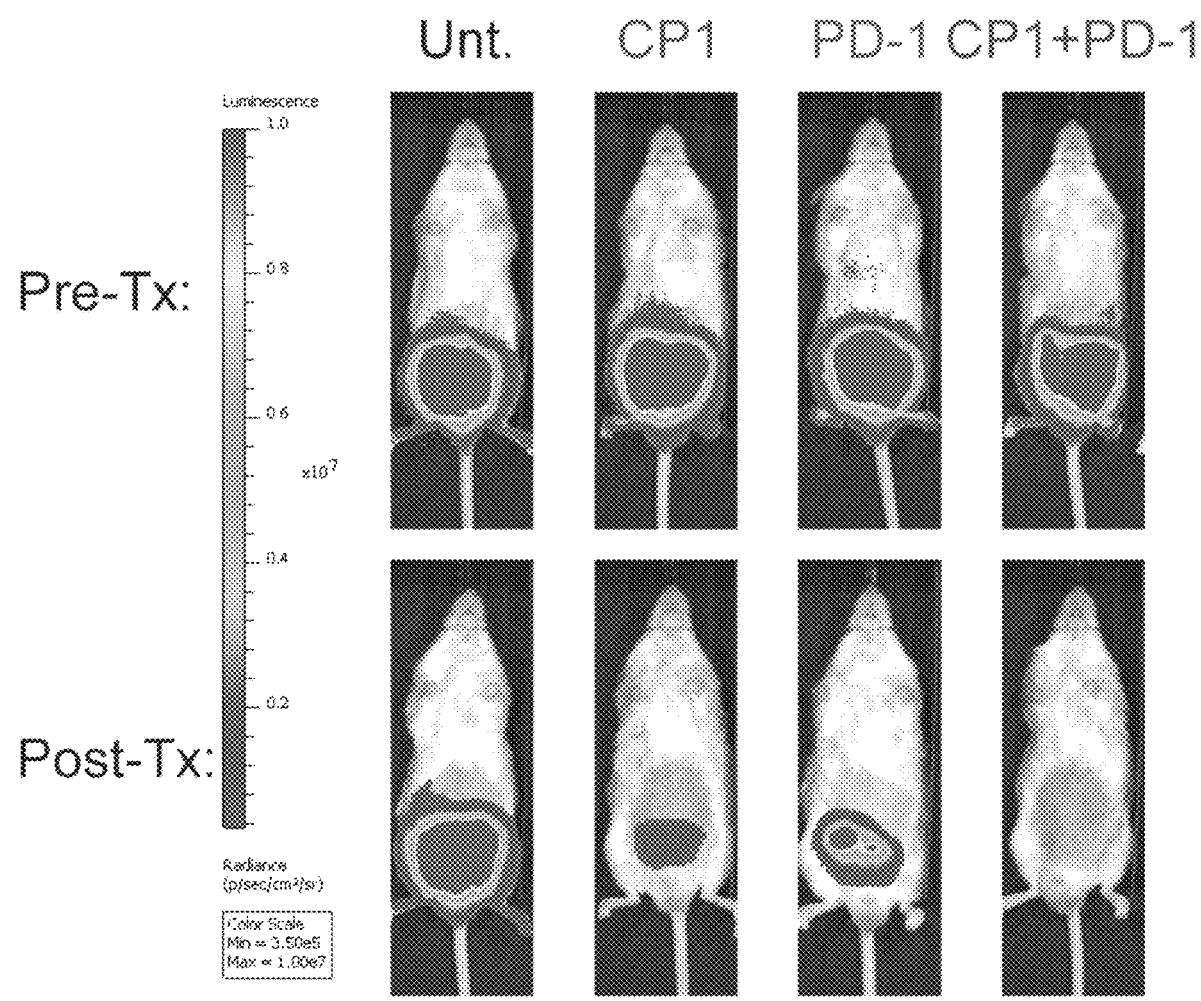
Figures 4D, 4E:
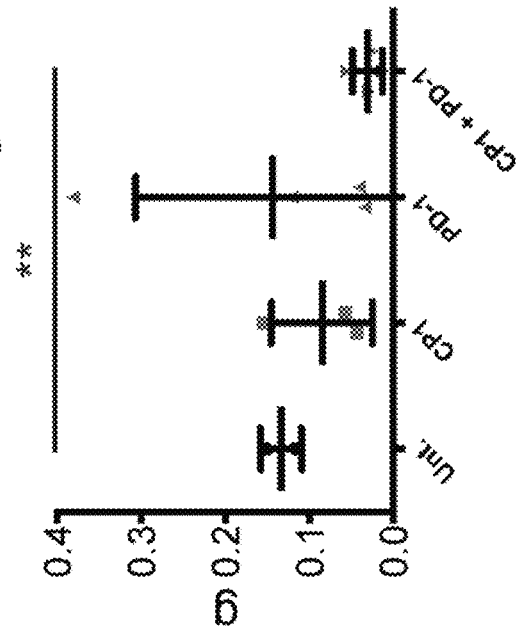
Figure 4F:
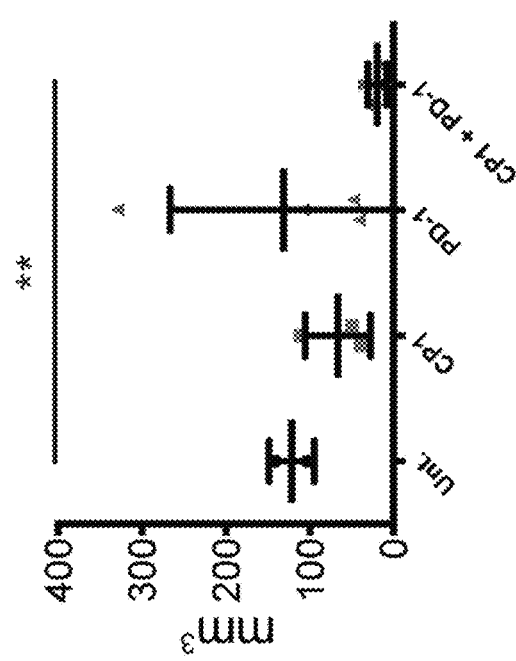

Combination CP1 and PD-1 Blockade is Efficacious in Treating Orthotopic Androgen-Dependent Prostate Cancer In patients, the prostate tumor microenvironment contains both PD-1$^+$ TILs and PD-L1$^+$ positive cancer cells. Myc is also overexpressed in up to 90% of prostate tumors, and can promote tumorigenesis in part through increasing PD-L1 expression. Therefore, to determine the functional implications of the observed in vitro and in vivo immunostimulatory properties of CP1, mice were administered intra-prostatic Myc-CaP cells, and subsequent orthotopic tumors were treated with intra-urethral CP1 followed by anti-PD-1 antibody at 9 d.p.i. Variability in tumor burden was controlled by normalizing in vivo bioluminescent imaging total flux (p/s) between experimental arms in this and all future in vivo experiments (FIG. 11A-E). Combination immunotherapy with CP1 and PD-1 blockade strongly and significantly increased survival, resulting in a 2.1-fold increased 50% survival time compared to untreated mice. In contrast, CP1 or anti-PD-1 monotherapy conferred only modest, insignificant increases in survival (FIG. 4A). Additionally, treatment efficacy was analyzed by multiple other measures. As monitored by in vivo bioluminescent imaging (FIG. 4B, C), tumor weight (FIG. 4D), tumor volume (FIG. 4E), and grossly (FIG. 4F), combination immunotherapy synergistically decreased tumor burden compared to either CP1 or PD-1 blockade alone.

Figure 12:
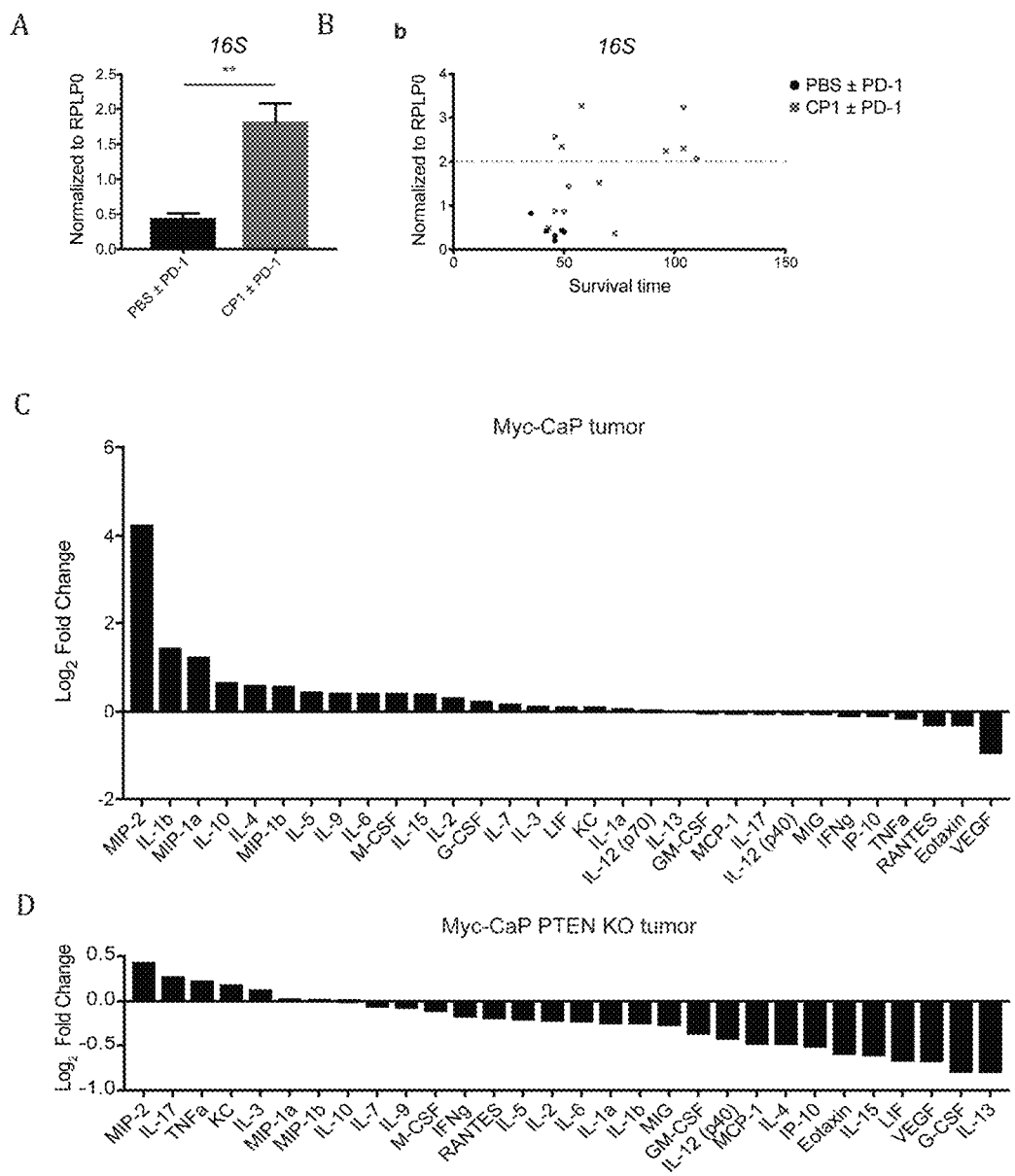
FIG. 12. CP1 load is linked to treatment efficacy. 16S qRT-PCR of Myc-CaP survival mice tumors (a) at their endpoints and (b) plotted over time after tumor injection, dotted line indicates cutoff for high CP1. Data represented as mean S.E.M. Statistical significance was determined by two-tailed Student's t-test. ** P<0.01. CP1 decreases intra-tumoral VEGF, increases pro-inflammatory cytokines and chemokines. Multiplex cytokine and chemokine array from (c) Myc-CaP survival tumors, performed with n=11-12 mice/experimental group, and from (d) Myc-CaP PTEN KO tumors, performed with n=5-6 mice/experimental group and technical duplicates. Data represented as log 2 fold change with and without CP1 administration.

Tumors from mice treated with CP1 contained significantly higher 16S overall (FIG. 12A). Mice surviving over 95 days contained a high level of 16S and all mice with low 16S survived less than 74 days, yet there was not a significant positive correlation with 16S over time (r=0.406; FIG. 12B), indicating that high bacterial burden was necessary for efficacy but was able to be controlled by the host. Within these high level CP1 tumors, and consistent with above cytokine/chemokine assays, VEGF was most downregulated at over 2-fold, while MIP-2, IL-1β, MIP-1α, and MIP-1β were among the most upregulated molecules (FIG. 12C).

Generation of a Novel CRPC-Like Syngeneic Mouse Model

Loss of PTEN is seen in up to 70% of prostate tumors and correlates with disease stage, progression to CRPC, and poor prognosis (Refs. 50-52; incorporated by reference in their entireties). PTEN is necessary for type I interferon immunity, and its loss has been linked to increased PD-L1 levels on prostate cancer cells and decreased TILs and increased resistance to PD-1 blockade in melanoma. Concurrent copy number gain in MYC and copy number loss in PTEN is the only copy number alteration (CNA) combination linked to prostate cancer-specific mortality, and was reported in 57% (n=14) of samples of metastatic prostate cancer at death compared to 9.6% in localized disease. Confirming that finding, 11.2% of TCGA primary prostate adenocarcinoma database samples contained both CNAs, which rose to 24.8% in the SU2C/PCF database of more advanced metastatic disease (FIG. 13A).

Figure 5B:
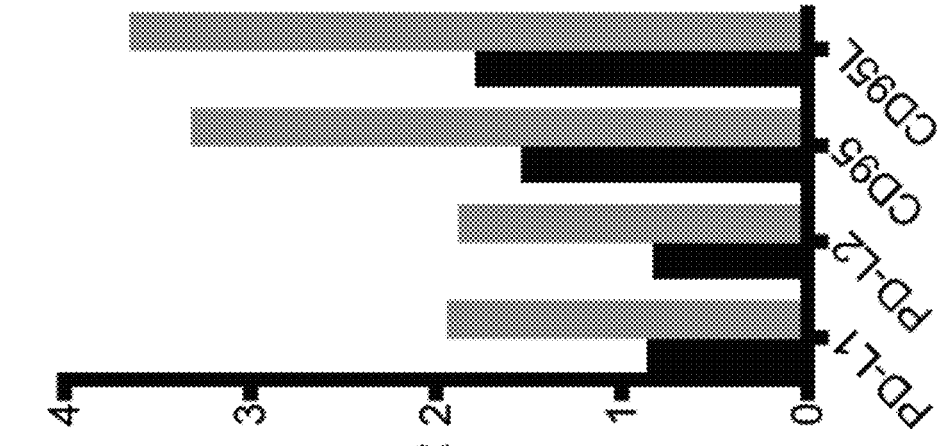
FIGS. 5A-H. Combination CP1 and anti-PD-1 immunotherapy is efficacious in treating a novel orthotopic CRPC-like model. Wildtype (WT) and PTEN knockout (KO) Myc-CaP cells in vitro A) western blot, B) flow cytometry, C-E) growth rate MTS assays, each sample analyzed in triplicates, in C) normal, D) low serum, and E) charcoal stripped (C.S.) serum, and as F) 3-dimensional organoids. G) Survival, n=7 mice/group and H) tumor volume, as determined by caliper measurements, of untreated (unt.), CP1, anti-PD-1, or combination CP1 and anti-PD-1 treated mice in orthotopic PTEN KO tumor-bearing mice.
Figure 5A:
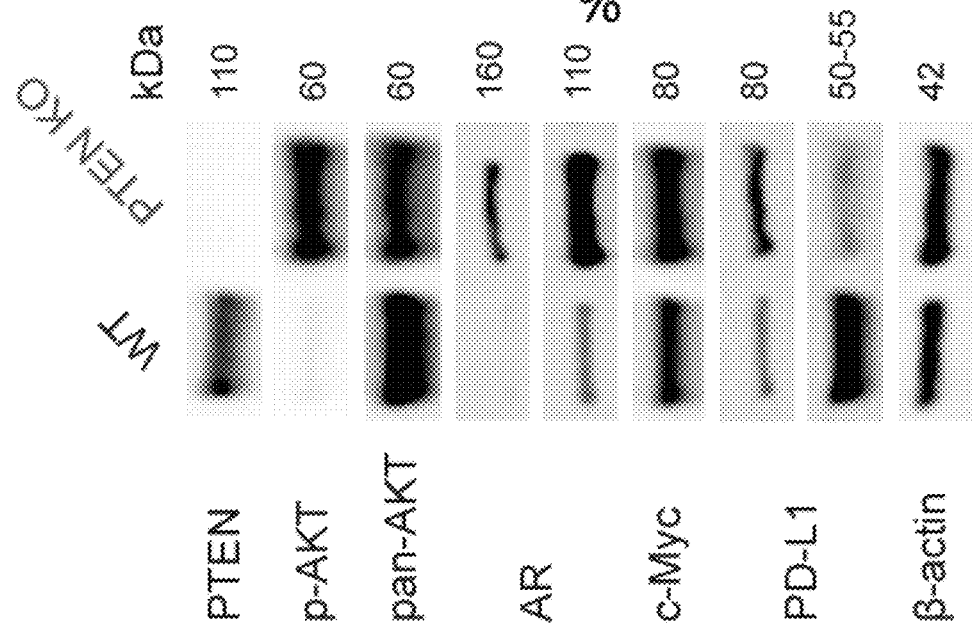
Figures 5C, 5D, 5E, 5F:
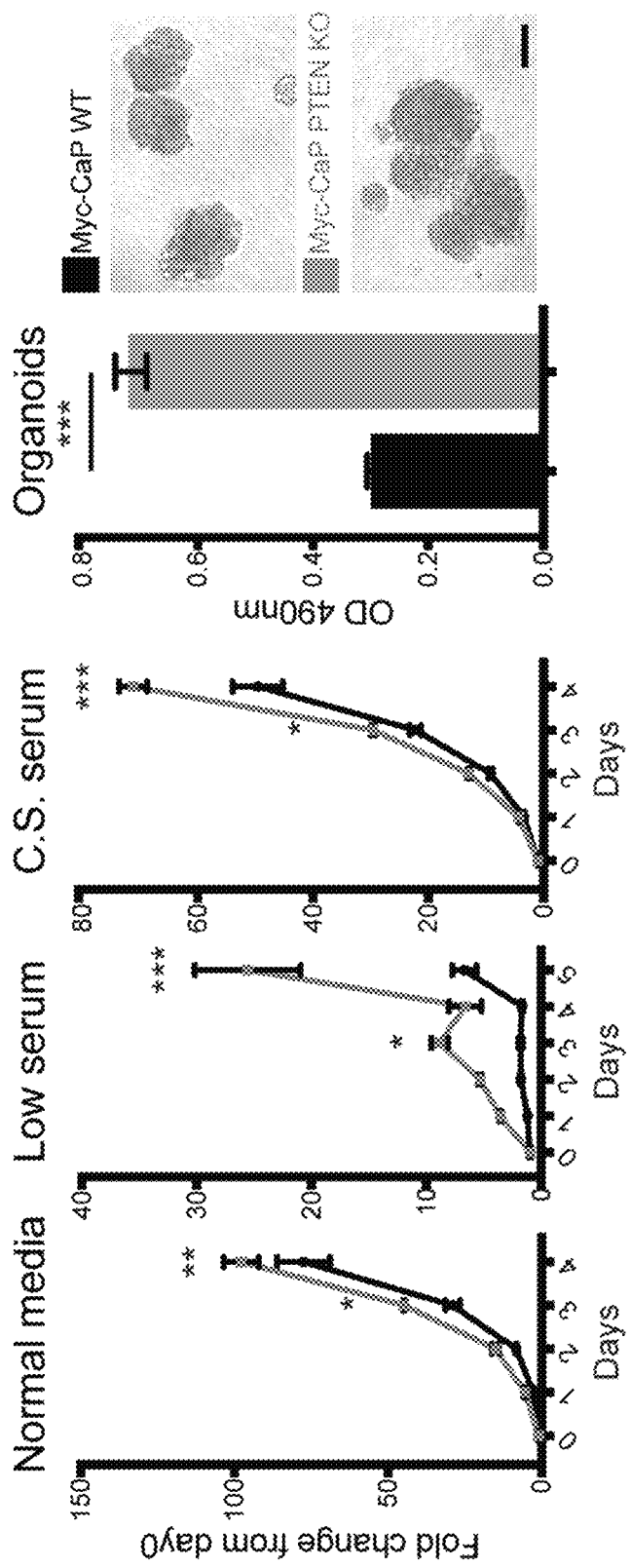

Therefore, in order to challenge our combination immunotherapy in a second more aggressive, immunosuppressive, and still clinically relevant model of prostate cancer, the CRISPR-Cas9 system to knock out (KO) PTEN from the Myc-CaP cell line. These cells displayed increased phosphorylated-AKT, mildly elevated c-Myc, and strongly elevated androgen receptor (AR) at both its normal (110 kDa) and high (160 kDa) molecular weight (M.W.) (FIG. 5A), the latter of which is the weight of RNF6-polyubiquinated AR, which paradoxically displays increased transcriptional activity and is linked to the development of CRPC (Ref 57; incorporated by reference in its entirety). PTEN KO cells also contained decreased 50-55 kDa PD-L1 but increased 80 kDa PD-L1 (FIG. 5A). In multiple cancer types, glycosylation of PD-L1 increases its M.W. and stabilizes the protein through resistance to proteasome-mediated degradation. Further, AKT activation suppresses the glycogen synthase kinase 3β (GSK3β) molecule necessary to phosphorylate PD-L1 and induce this degradation. By flow cytometry, the PTEN KO cells displayed approximately 2-fold increased levels of PD-L1 (Ref. 54; incorporated by reference in its entirety), PD-L2, CD95, and CD95L, all important in tumor immune-evasion (FIG. 5B). Further, these cells grew faster than wildtype (WT) Myc-CaP under normal growth conditions (FIG. 5C), which was magnified in both low (FIG. 5D) and charcoal-stripped (FIG. 5E) serum conditions. PTEN KO Myc-CaP cells also formed larger 3-dimensional organoids at a faster rate (FIG. 5F). Taken together, the PTEN KO Myc-CaP cell line is a much faster growing, more aggressive cell line displaying many properties of CRPC (genetic relevance to human CRPC, increased normal and high M.W. AR, and faster growth with depleted androgen).

Figure 5H:
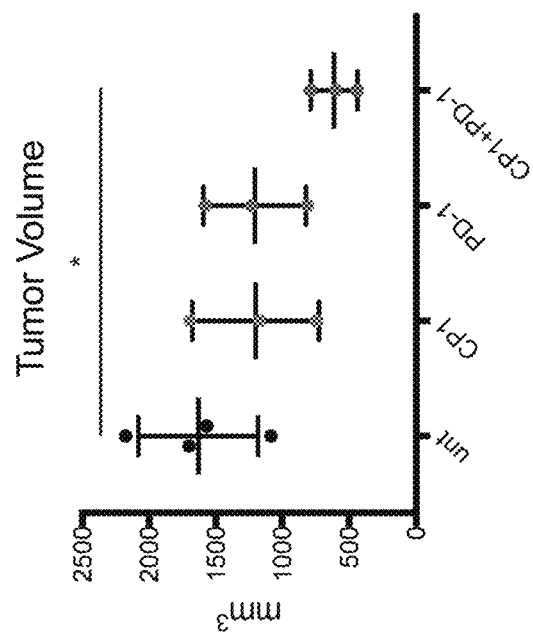
Figure 5G:
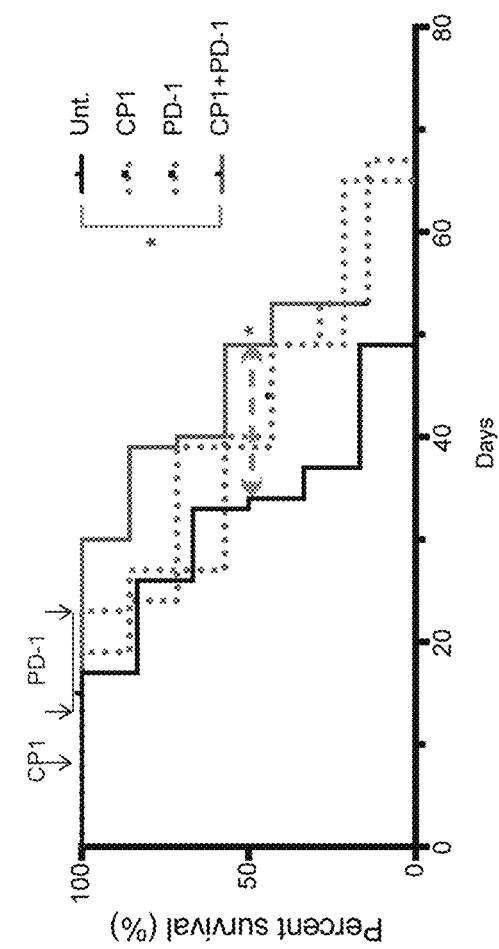

Combination CP1 and PD-1 Blockade is Efficacious in Treating Orthotopic CRPC-Like PTEN KO Prostate Cancer Mice were intra-prostatically injected with PTEN KO Myc-CaP cells, and after the orthotopic development of these CRPC-like tumors, were administered CP1 with or without subsequent anti-PD-1. Combination immunotherapy of CP1 followed by anti-PD-1 antibody again significantly increased survival time and conferred a 1.5-fold increased 50-day survival time. Also consistent with the Myc-CaP WT model, treatment with either monotherapy resulted in only a mild, insignificant survival benefit (FIG. 5G). Further, only combination immunotherapy treated tumors were significantly smaller than those untreated, in comparison to those administered CP1 or PD-1 monotherapy (FIG. 5H).

However, despite decreases in volume, tumors across all groups showed no differences in weight (FIG. 13). Overall, CP1 tumors were denser, with PBS and CP1 administered tumor weights and volumes independently significantly correlating (r=0.96 and r=0.97, respectively), with the two density slopes being significantly different (FIG. 13C). To determine if the increased density of CP1 administered tumors was the result of increased inflammation and exudate in these larger, more appreciable tumors (as compared to WT Myc-CaP), fibrinogen levels. Tumors from CP1 administered mice (with or without anti-PD-1) contained increased fibrinogen (FIG. 13D-F). Therefore, CP1 likely increased tumor weight due to increased inflammation and exudate infiltration, and only tumor volume accurately assessed treatment efficacy in PTEN KO tumors. This is in agreement with clinical immunotherapies, which, unlike cytotoxic agents, commonly demonstrate increased tumor burden before subsequent clinical response and are thus monitored under the immune-related response criteria (irRC).

Figure 6A:
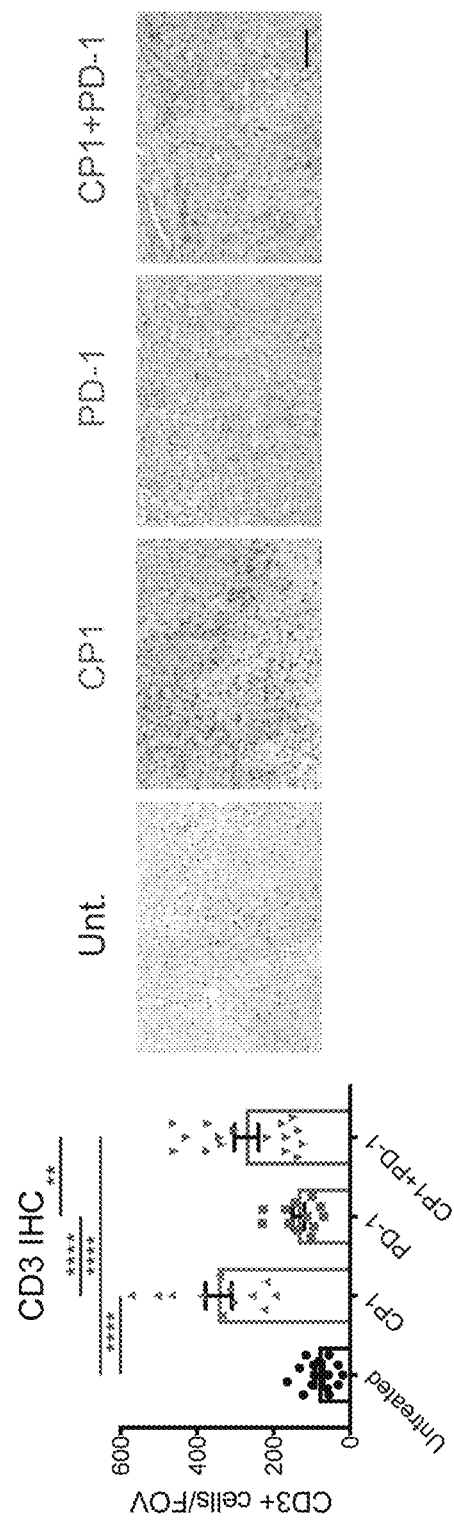
Figure 6B:
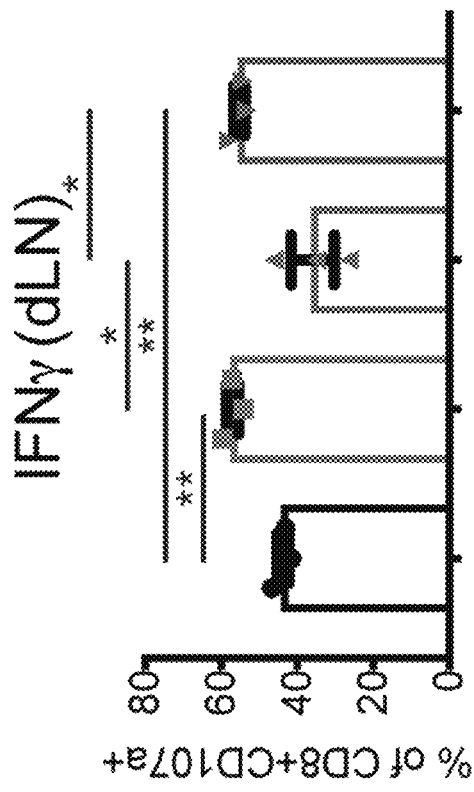
Figure 6B:
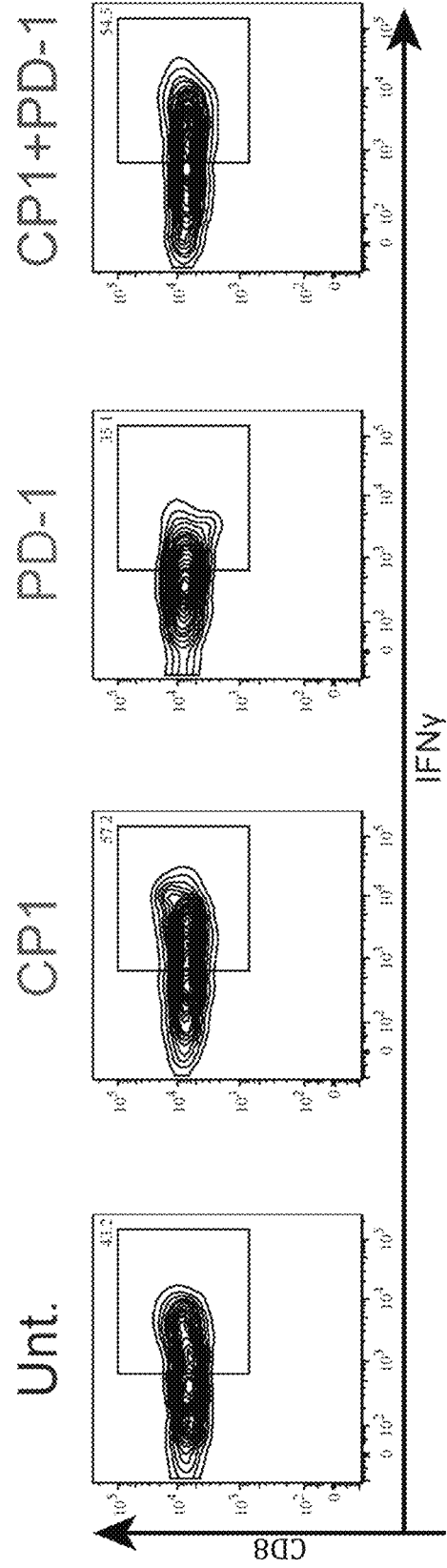
Figure 6E:
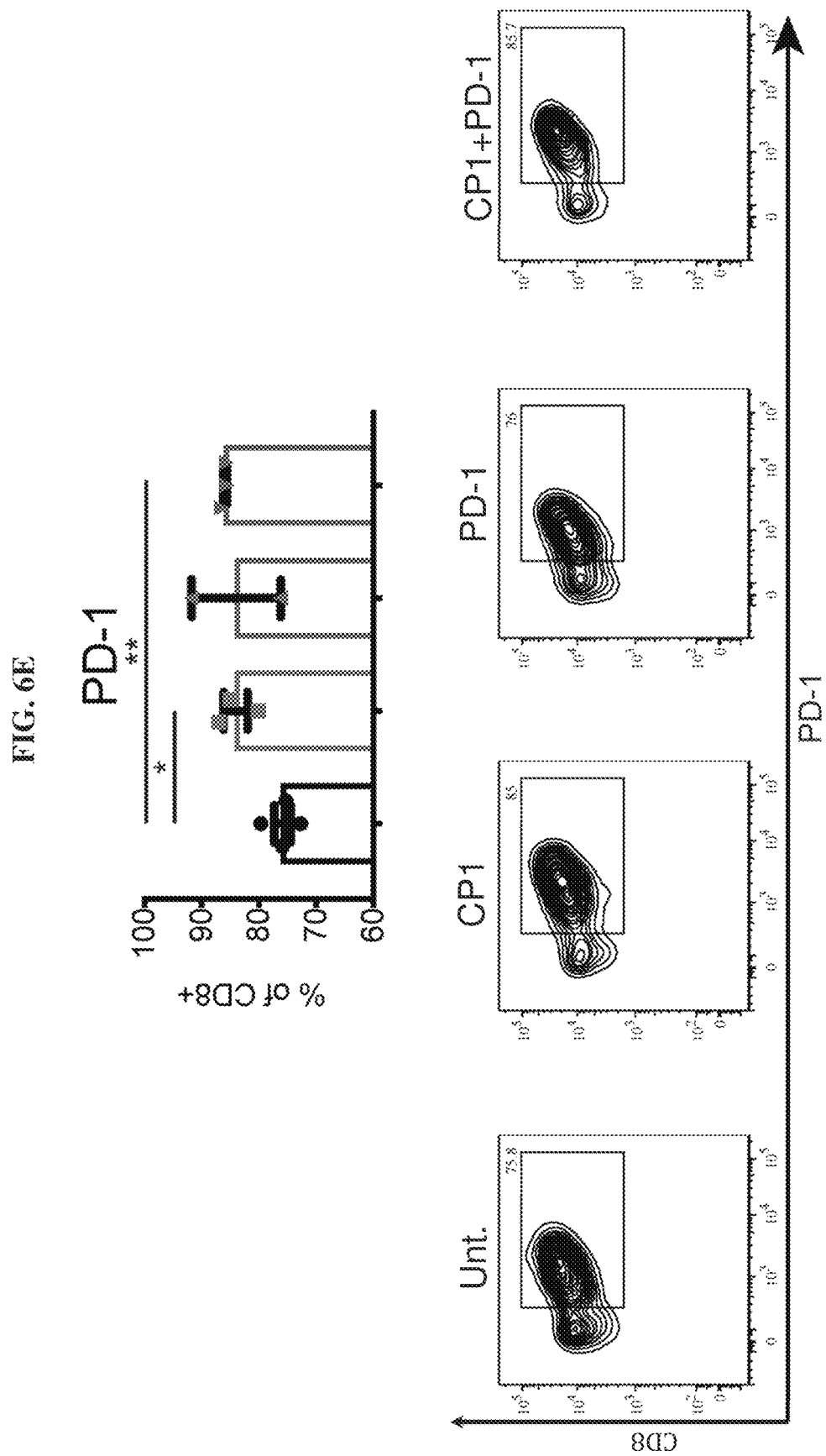
Figure 6F:
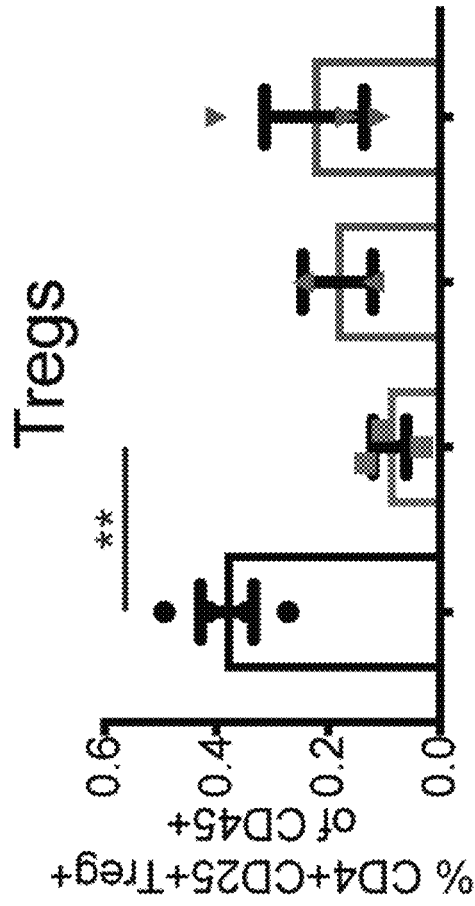
Figure 6F:
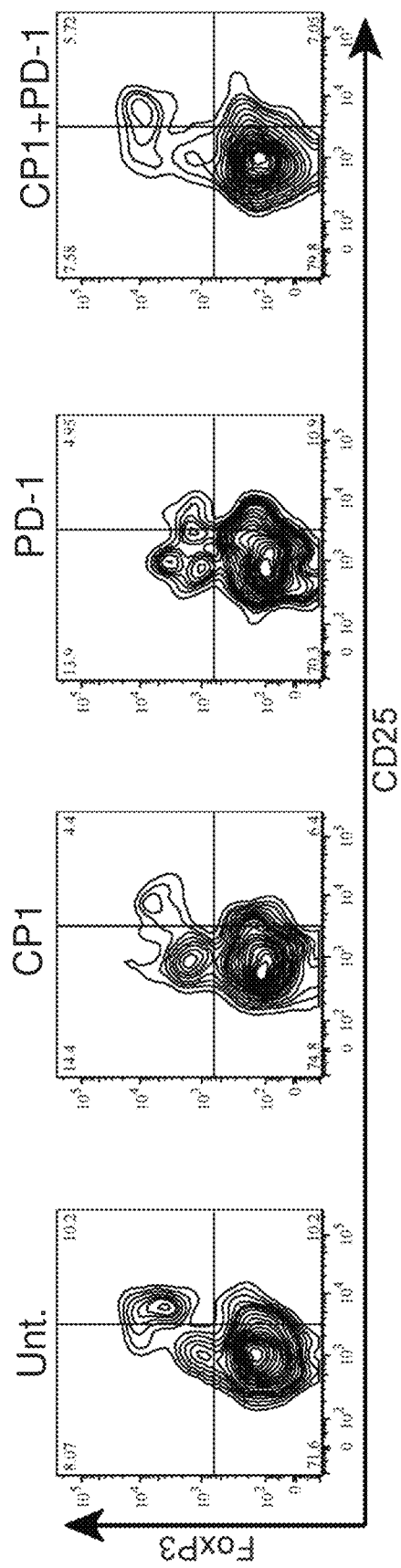
Figure 6G:
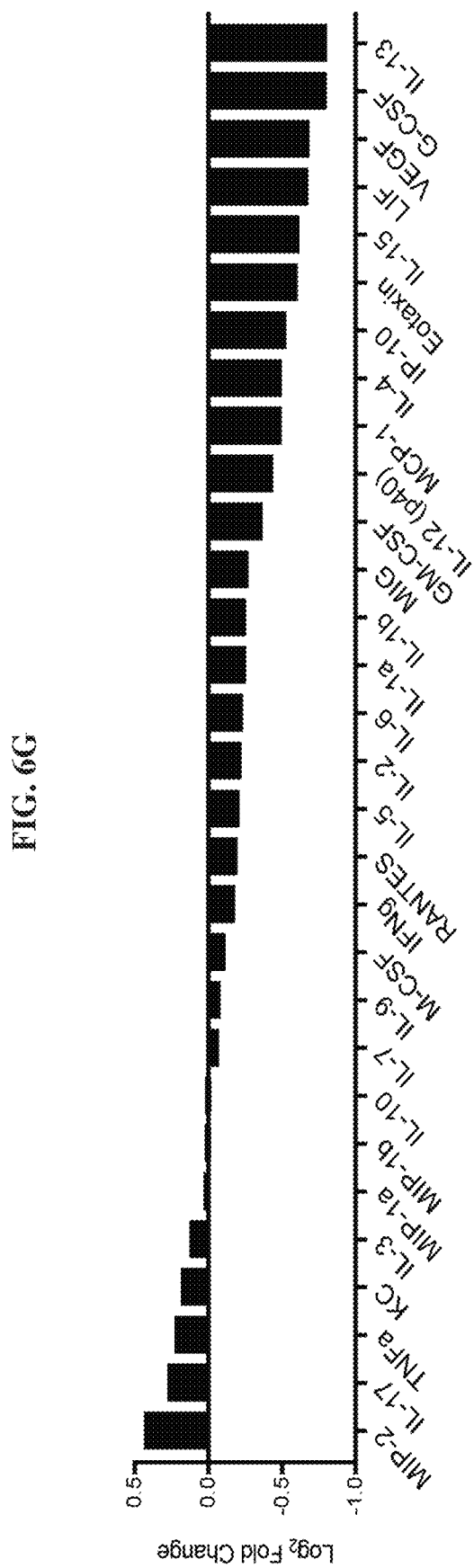

Within these PTEN KO tumors, CP1 treatment again proved to increase TILs, with or without anti-PD-1 administration, as displayed by CD3 IHC (FIG. 6A). Further, CP1 and/or CP1+PD-1 treated mice showed increased IFNγ (FIG. 6B), granzyme B (FIG. 6C), and perforin (FIG. 6D) production from degranulated cytotoxic CD8 dLN T cells. CP1 and/or CP1+PD-1 treated tumors also contained increased PD-1 levels on CD8 TILs (FIG. 6E) and decreased percentage of Tregs comprising total infiltrating immune cells (FIG. 6F), consistent with the impact of CP1 in Myc-CaP WT tumors. Additionally, multiplex analysis again demonstrated that CP1 administered tumors contained decreased VEGF, and well as increased MIP-2, IL-17, and TNFα (FIG. 6G), as seen above. Overall, the combination of CP1 and anti-PD-1 demonstrate efficacy in a second, CRPC-like model of the disease, and CP1 increased TIL densities and cytotoxic functionality and activation of CD8 T cells, as well as again decreased intratumoral Tregs and VEGF.

Figure 7B:
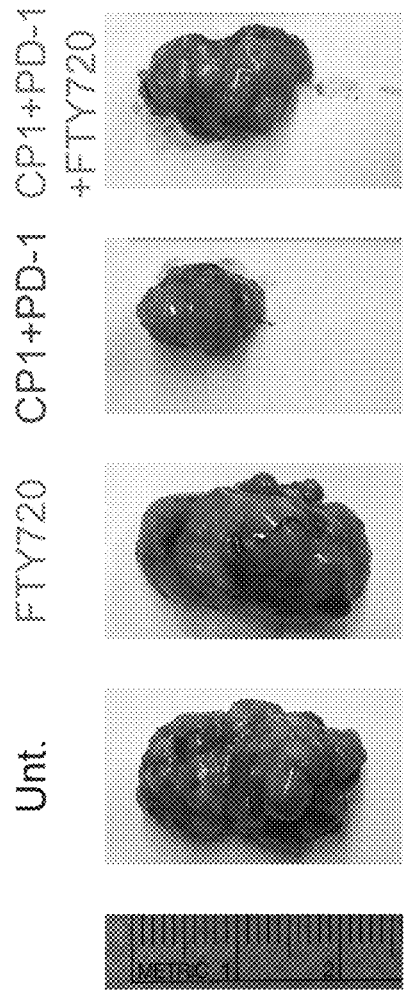
Figure 7A:
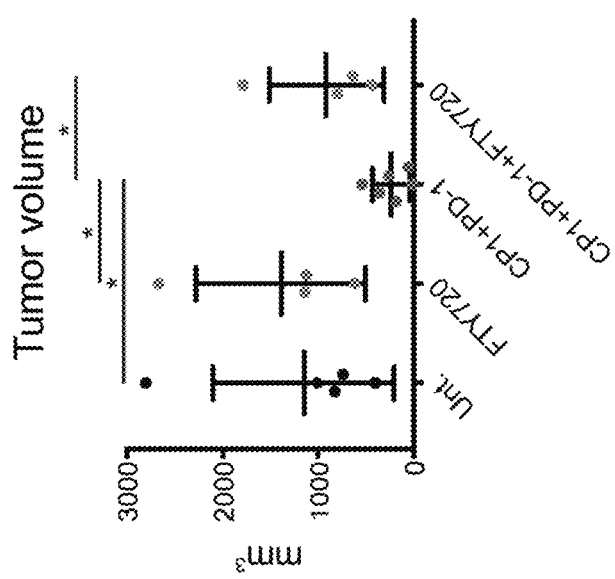
Figure 7C:
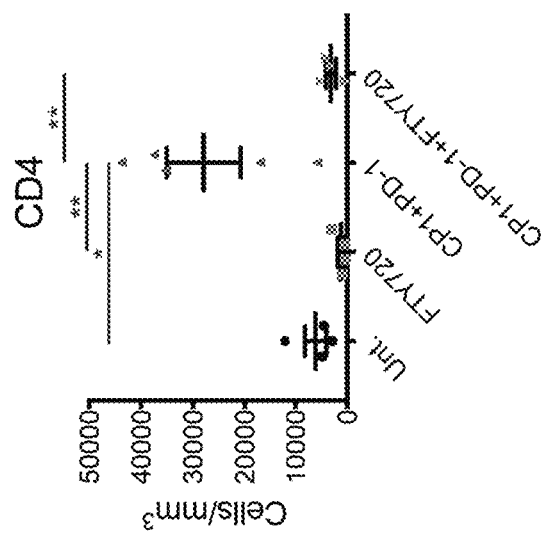
Figure 7D:
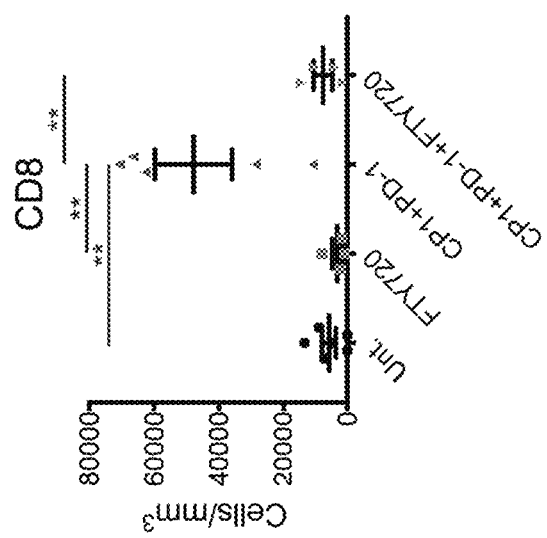
Figure 7E:
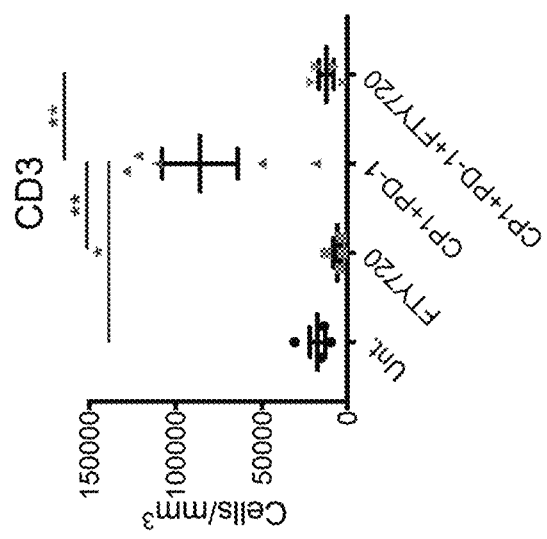
Figure 8:
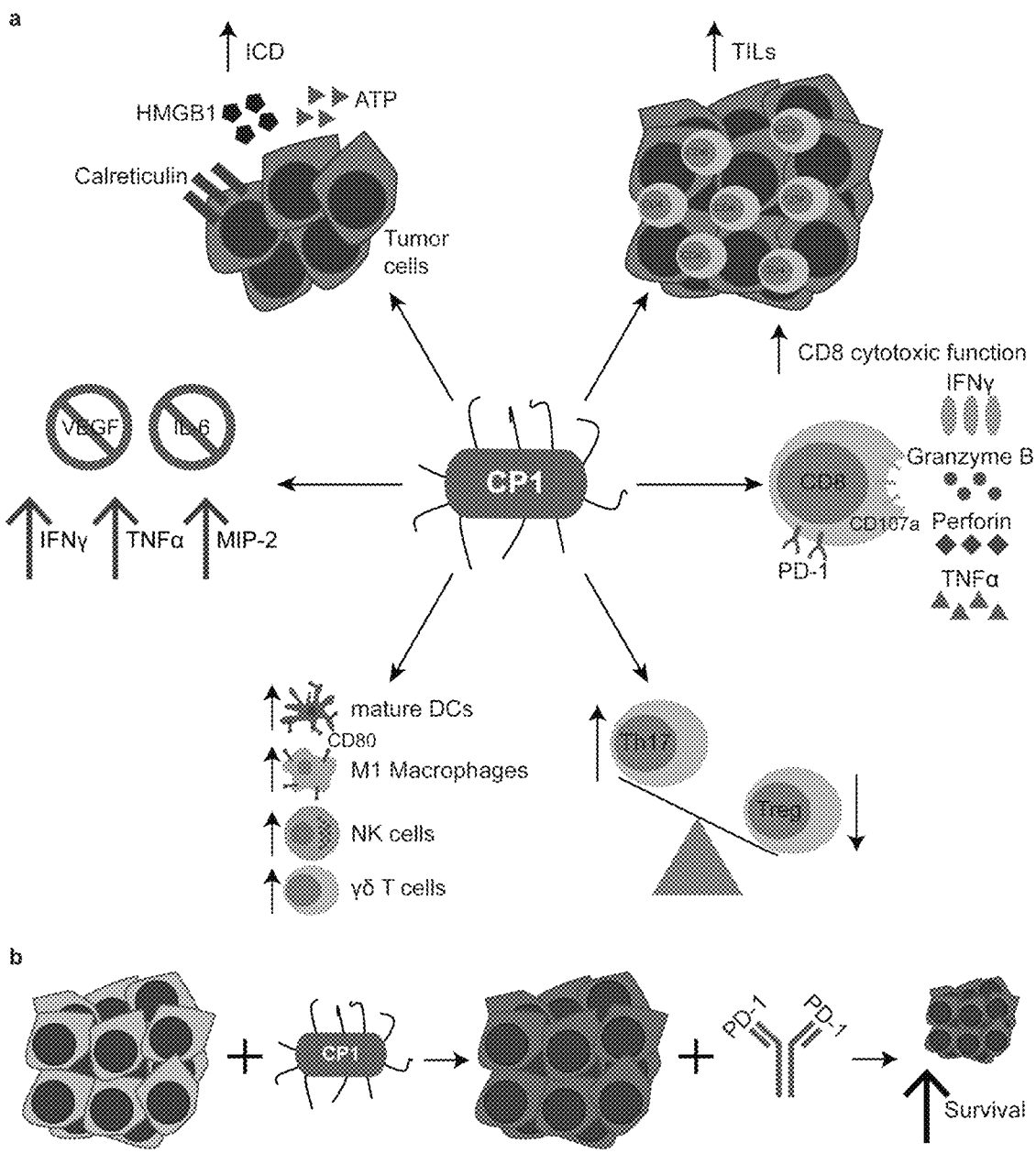
FIG. 8. CP1 is a tissue-specific, multifaceted immunotherapeutic tool. (A) Intra-urethrally administered CP1 colonized tumor tissue and increases CD8 and CD4 TILs, T cell cytotoxic function via IFNγ, granzyme B, and perforin, skews the Th17/Treg axis to increased Th17 cells and decreased Treg TILs, increases tumor infiltration of mature DCs, M1 macrophages, NK cells, 76 T cells, and B cells, decreases intra-tumoral VEGF and IL-6, and directly kills cancer cells with induction of immunogenic cell death (ICD), thereby reprogramming the non-immunogenic "cold" prostate tumor microenvironment and sensitizes tumors to anti-PD-1 blockade, resulting in decreased tumor burden and increased survival. (B) CP1 reprograms non-immunogenic "cold" prostate tumor microenvironment and sensitizes tumors to anti-PD-1 blockade, resulting in decreased tumor burden and increased survival.

The Ability of CP1 to Potentiate PD-1 Blockade is Partially Dependent on Increased TIL Recruitment To determine if CP1's ability to recruit lymphocytes into the tumor is necessary for its proven synergy with PD-1 blockade, fingolimod (FTY720), a sphingosine-1 phosphate mimetic that blocks egress of T cells from the lymph nodes into peripheral tissues, was administered. PTEN KO orthotopic tumor-bearing mice were treated with CP1 and anti-PD-1, with the addition of FTY720 administration beginning immediately before CP1 administration, to specifically block CP1-induced T cell infiltration into the tumor without inhibiting the quantity or function of the baseline TILs present in these tumors. Tumors from mice administered CP1 and PD-1 combination therapy were significantly smaller than those untreated, administered FTY720 alone, as well as those treated with combination CP1 and anti-PD-1 and FTY720 (FIG. 7A, B). Also as seen previously, combination CP1 and anti-PD-1 treated tumors contained greater number of CD3, CD8, and CD4 TILs. However, this was now effectively reversed back to untreated levels with the addition of FTY720, as assessed by flow cytometry (FIG. 7C-E) and IHC (FIG. 7F). Therefore, recruitment of T cells into the tumor microenvironment was a necessary component of CP1's mechanism of inducing anti-tumor immunity. Additionally, while not statistically significant, CP1+PD-1+ FTY720 tumors (mean 917 mm$^3$) were smaller than those administered FTY720 alone (mean 1394 mm$^3$) (FIG. 7A), indicating that anti-PD-1 and the other immunostimulating facets of CP1 retained a lesser but still functional impact on baseline TILs.

Example 2

Experiments are conducted to genetically modify the uropathogenic *E. coli* CP1 as a therapeutic treatment option for these in need patient populations. For example, CP1 has been genetically modified to express prostate-specific antigen (PSA), prostate stem cell antigen and its mouse homologue (hPSCA and mPSCA), as well as yellow fluorescent protein (YFP) as an antigen control. It is contemplated that by overexpressing these tumor-associated antigens (TAAs) in the context of the local inflammation that CP1 induces, the modified CP1 will result in antigen presentation and the formation of PSA- or PSCA-specific T cells capable of mounting an efficacious anti-tumor response.

PSA, which is a kallikrein serine protease secreted from prostate luminal epithelial cells, was chosen as the model TAA, as it is abundantly expressed with great specificity from prostate tissue. Additionally, the protein is overexpressed in prostate malignancies, including CRPC, and clinical trials utilizing PSA in experimental vaccines have shown a survival benefit for men with advanced prostate cancer, as patients have been able to generate PSA-specific T cell.

Prostate stem cell antigen (PSCA) was also chosen as a TAA, as it is a GPI-anchored cell surface glycoprotein both abundantly and specifically expressed from prostate epithelial cells. PSCA is overexpressed in approximately 60% of local prostate cancer and between 60-100% of advanced metastatic disease. In addition, PSCA expression has been correlated to worsening clinical disease and Gleason score, as well as progression to CRPC, and in vivo studies have demonstrated the ability to form functional PSCA-specific T cells.

Figure 21:
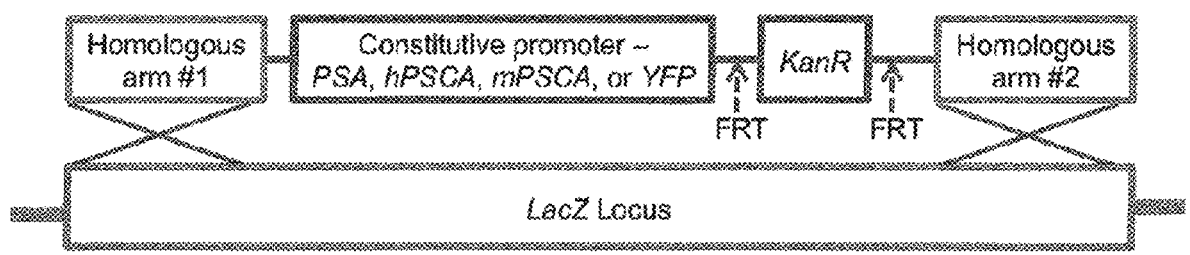
FIG. 21. Integration of the gene for PSA, hPSCA, mPSCA, or YFP into the lacZ locus of CP1 utilizing linearized integration vectors containing two JacZ homologous arms and a Kanamycin resistance gene (KanR) flanked by flippase recognition target (FRT) sites.
Figure 22:
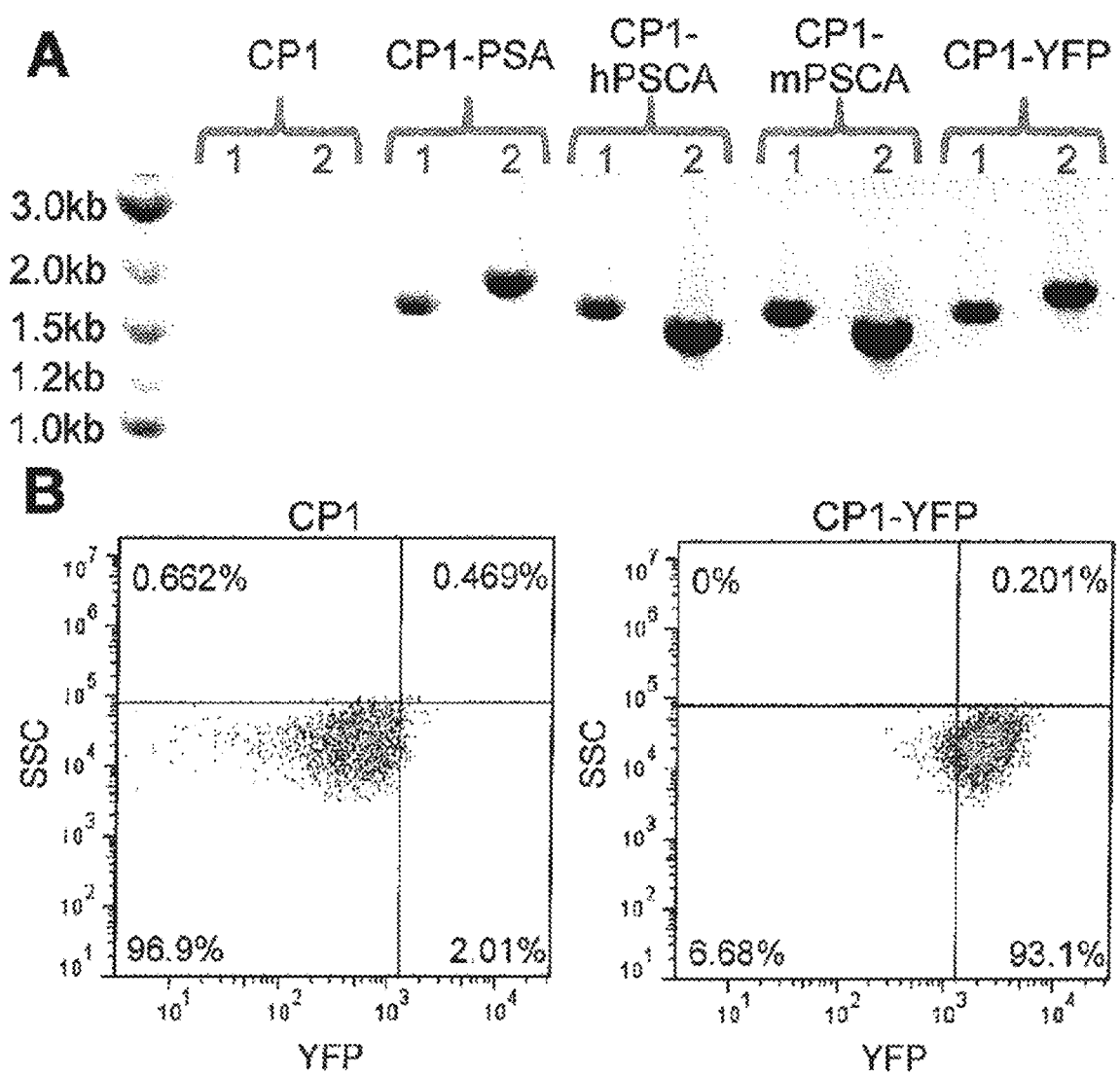
FIGS. 22A-B. The PSA, hPSCA, mPSCA, and YFP genes have been successfully integrated into the CP1 genome. (A) PCR at integration borders 1 and 2, each with a primer within genomic and integrated DNA. PCR 1 amplicon size is identical for each strain, while PCR 2 amplicon size varies as it contains the inserted gene. (B) Flow cytometry of gated CP1-YFP.

To modify CP1 to express these TAAs, we have integrated these genes within the genome of CP1 for stable, long-term expression, assuring that expression is maintained throughout the in vivo prostatic colonization. These genes were first fused downstream of a constitutive RecA promoter, and the generated construct was subsequently ligated between two arms, each containing 500 base pair homology to the *E. coli* lacZ locus, on an integration vector. The ligated insert was verified by sequencing. Further, CP1 was transformed to express λ Red recombinase, as is necessary for DNA integration. Linearized integration vectors were integrated into the /acZ locus via homologous recombination (FIG. 21). Integration was confirmed by screening PCR at each integration border at the CP1/acZ locus (FIG. 22A), and YFP expression was demonstrated by flow cytometry (FIG. 22B). Additionally, the kanamycin resistance gene (KanR) is flanked by flippase recognition target (FRT} sites, and will be excised after transformation of CP1 to express FLP recombinase (FIG. 21), thereby eliminating the risk of horizontal gene transfer of antibiotic resistance, and furthering the translational potential of CP1.

Figure 23:
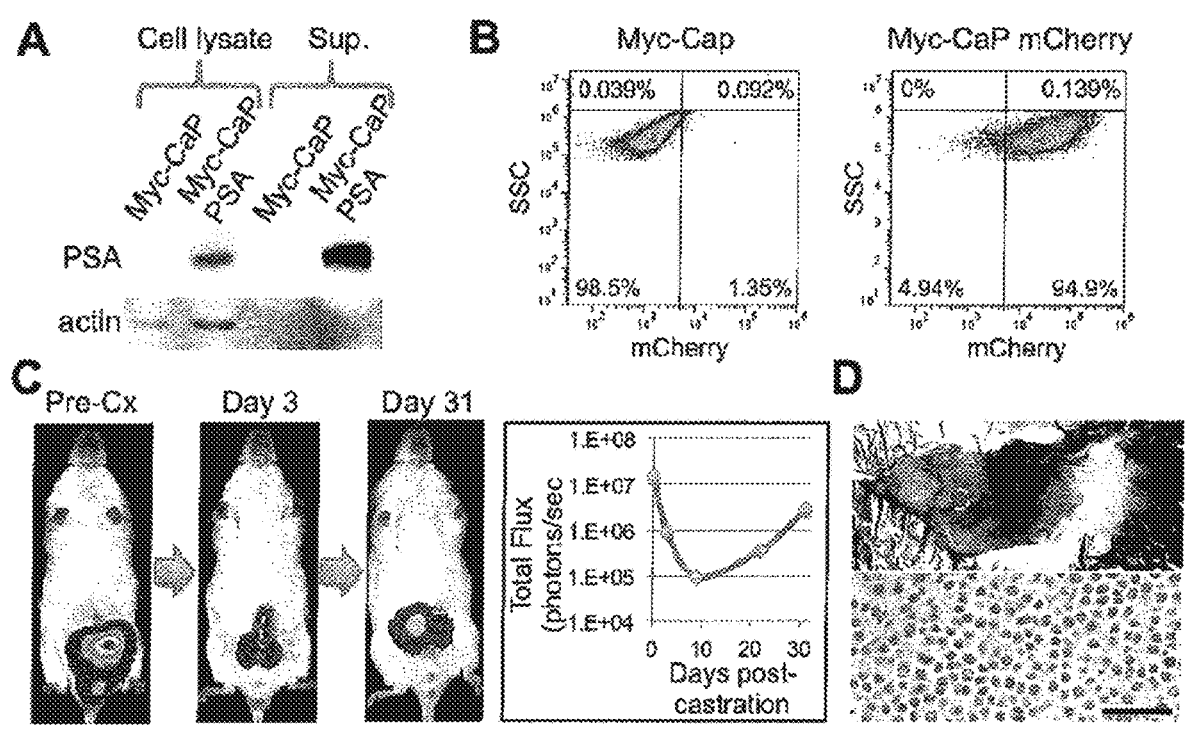
FIGS. 23A-D. Model of CRPC using Myc-CaP cell line. In transduced and untransduced Myc-CaP cells, (A) Western blot for PSA in cell lysate and supernatant, (B) flow cytometry for mCherry, (C) in vivo bioluminescent imaging for luciferase. Tumors were surgically implanted in the anterior prostate and mice were surgically castrated (Cx) after tumor development, leading to (C) regression and (C, D) recurrence, further evident by (D) gross dissection and H&E histology (scale bar=50︎1Jm).

To evaluate the efficacy of CP1 expressing PSA to treat CRPC, the disease state is modeled by surgically implanting MycCaP cancer cells into the anterior lobe of the prostate, and, after orthotopic tumor development, mice are castrated, leading to tumor regression followed by CRPC recurrence, at which point CP1 expressing PSA is therapeutically administered (FIG. 23C, D). Myc-CaP has been engineered to express PSA, mCherry, and luciferase (to allow for in vivo tumor monitoring) by lentiviral transduction FIG. 23A-C). This local CRPC model has great clinical relevancy for a number of reasons. Men who receive radiation therapy commonly retain some prostate tissue as evident by non-zero PSA levels post-treatment, and approximately 40-60% of patients experience recurrence after radiation therapy with 10-25% of patients recurring locally. In patients treated with retropubic radical prostatectomy, 17-40% showed biochemical recurrence within 10 years, including 2-21.5% of patients who presented with local recurrence within 3-15 years after surgery.

Figure 24:
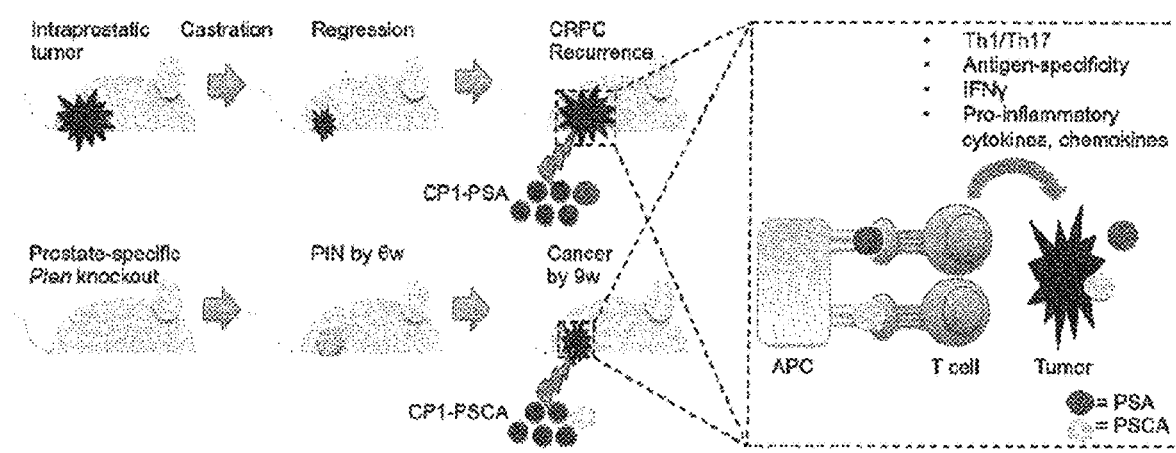
FIG. 24. Summary of CP1 as an immunotherapy for prostate cancer. (Top) Tumor cells are implanted intra-prostatically, mice are castrated, and CP1-PSA is administered after tumor regression and subsequent CRPC recurrence. (Bottom) Prostate-specific Pten knockout mice are administered CP1-PSCA after cancer development by 9 weeks of age.

To evaluate the efficacy of CP1 expressing hPSCA or mPSCA to treat early stage prostate cancer, this disease state is represented using Probasin$^{Cre/+}$; Pten$^{flox/flox}$ mice in which the Pten tumor suppressor gene is deleted specifically from prostate cells via Cre Recombinase expressed under the Probasin promoter. These mice all develop prostatic intra-epithelial neoplasia (PIN) by 6 weeks and early stage cancer by 9 weeks of age, and tumors upregulate PSCA 14-fold. The efficacy of CP1 treatment in both models is evaluated by survival, tumor histological analysis, tumor burden by imaging, immunophenotyping by flow cytometry, and antigen-specificity of infiltrating and locally draining T cells by peptide pulsing and multimer staining. Experiments in these two disease states are summarized in FIG. 24.

REFERENCES

The following references, some of which are cited above by number, are herein incorporated by reference in their entireties.

1. Tumeh, P. C., et al., PD-1 blockade induces responses by inhibiting adaptive immune resistance. Nature, 2014. 515 (7528): p. 568-71.
2. Alexandrov, L. B., et al., Signatures of mutational processes in human cancer. Nature, 2013. 500(7463): p. 415-21.
3. Champiat, S., et al., Exomics and immunogenics: Bridging mutational load and immune checkpoints efficacy. Oncoimmunology, 2014. 3(1): p. e27817.
4. Kwon, E. D., et al., Ipilimumab versus placebo after radiotherapy in patients with metastatic castration-resistant prostate cancer that had progressed after docetaxel chemotherapy (CA184-043): a multicentre, randomised, double-blind, phase 3 trial. Lancet Oncol, 2014. 15(7): p. 700-12.
5. Bracarda, S., et al., Comparing comparators: a look at control arms in kidney cancer studies over the years. Br J Cancer, 2015. 112(1): p. 14-9.
6. Topalian, S. L., et al., Safety, activity, and immune correlates of anti-PD-1 antibody in cancer. N Engl J Med, 2012. 366(26): p. 2443-54.
7. Gevensleben, H., et al., The Immune Checkpoint Regulator PD-L1 Is Highly Expressed in Aggressive Primary Prostate Cancer. Clin Cancer Res, 2016. 22(8): p. 1969-77.
8. Sfanos, K. S., et al., Human prostate-infiltrating CD8+T lymphocytes are oligoclonal and PD-1+. Prostate, 2009. 69(15): p. 1694-703.
9. Ebelt, K., et al., Prostate cancer lesions are surrounded by FOXP3+, PD-1+ and B7-H1+ lymphocyte clusters. Eur J Cancer, 2009. 45(9): p. 1664-72.
10. Larkin, J., et al., Combined Nivolumab and Ipilimumab or Monotherapy in Untreated Melanoma. N Engl J Med, 2015. 373(1): p. 23-34.
11. Yasuda, S., et al., Simultaneous blockade of programmed death 1 and vascular endothelial growth factor receptor 2 (VEGFR2) induces synergistic anti-tumour effect in vivo. Clin Exp Immunol, 2013. 172(3): p. 500-6.
12. Robert, C., et al., Ipilimumab plus dacarbazine for previously untreated metastatic melanoma. N Engl J Med, 2011. 364(26): p. 2517-26.
13. Demaria, S., et al., Immune-mediated inhibition of metastases after treatment with local radiation and CTLA-4 blockade in a mouse model of breast cancer. Clin Cancer Res, 2005. 11(2 Pt 1): p. 728-34.
14. Melero, I., et al., Evolving synergistic combinations of targeted immunotherapies to combat cancer. Nat Rev Cancer, 2015. 15(8): p. 457-72.
15. Coley, W. B., The Treatment of Inoperable Sarcoma by Bacterial Toxins (the Mixed Toxins of the *Streptococcus erysipelas* and the *Bacillus prodigiosus*). Proc R Soc Med, 1910. 3(Surg Sect): p. 1-48.
16. Morales, A., D. Eidinger, and A. W. Bruce, Intracavitary *Bacillus* Calmette-Guerin in the treatment of superficial bladder tumors. J Urol, 1976. 116(2): p. 180-3.
17. Roberts, N. J., et al., Intratumoral injection of *Clostridium novyi*-NT spores induces antitumor responses. Sci Transl Med, 2014. 6(249): p. 249ra111.
18. Rudick, C. N., et al., Uropathogenic *Escherichia coli* induces chronic pelvic pain. Infect Immun, 2011. 79(2): p. 628-35.
19. Quick, M. L., et al., Th1-Th17 cells contribute to the development of uropathogenic *Escherichia coli*-induced chronic pelvic pain. PLoS One, 2013. 8(4): p. e60987.
20. Simons, B. W., et al., A human prostatic bacterial isolate alters the prostatic microenvironment and accelerates prostate cancer progression. J Pathol, 2015. 235(3): p. 478-89.
21. Hannani, D., et al., Harnessing gammadelta T cells in anticancer immunotherapy. Trends Immunol, 2012. 33(5): p. 199-206.
22. Muranski, P., et al., Th17 cells are long lived and retain a stem cell-like molecular signature. Immunity, 2011. 35(6): p. 972-85.
23. Ellis, L., et al., Generation of a syngeneic orthotopic transplant model of prostate cancer metastasis. Oncoscience, 2014. 1(10): p. 609-613.
24. Wallace, J., Humane endpoints and cancer research. ILAR J, 2000. 41(2): p. 87-93.
25. Gao, J., et al., Integrative analysis of complex cancer genomics and clinical profiles using the cBioPortal. Sci Signal, 2013. 6(269): p. pl1.
26. Cerami, E., et al., The cBio cancer genomics portal: an open platform for exploring multidimensional cancer genomics data. Cancer Discov, 2012. 2(5): p. 401-4.
27. Cancer Genome Atlas Research, N., The Molecular Taxonomy of Primary Prostate Cancer. Cell, 2015. 163 (4): p. 1011-25.
28. Robinson, D., et al., Integrative clinical genomics of advanced prostate cancer. Cell, 2015. 161(5): p. 1215-28.
29. Green, D. R., et al., Immunogenic and tolerogenic cell death. Nat Rev Immunol, 2009. 9(5): p. 353-63.
30. Kepp, O., et al., Consensus guidelines for the detection of immunogenic cell death. Oncoimmunology, 2014. 3(9): p. e955691.
31. Liu, W., et al., Genetic markers associated with early cancer-specific mortality following prostatectomy. Cancer, 2013. 119(13): p. 2405-12.
32. Xu, K., et al., Regulation of androgen receptor transcriptional activity and specificity by RNF6-induced ubiquitination. Cancer Cell, 2009. 15(4): p. 270-82.
33. Li, C. W., et al., Glycosylation and stabilization of programmed death ligand-1 suppresses T-cell activity. Nat Commun, 2016. 7: p. 12632.
34. Runowicz, C. D., et al., American Cancer Society/ American Society of Clinical Oncology Breast Cancer Survivorship Care Guideline. J Clin Oncol, 2016. 34(6): p. 611-35.
35. Alibhai, S. M., et al., 30-day mortality and major complications after radical prostatectomy: influence of age and comorbidity. J Natl Cancer Inst, 2005. 97(20): p. 1525-32.
36. Murray, L., et al., Second primary cancers after radiation for prostate cancer: a systematic review of the clinical data and impact of treatment technique. Radiother Oncol, 2014. 110(2): p. 213-28.
37. Zhao, J., et al., Androgen deprivation therapy for prostate cancer is associated with cardiovascular morbidity and mortality: a meta-analysis of population-based observational studies. PLoS One, 2014. 9(9): p. e107516.
38. Kirby, M., C. Hirst, and E. D. Crawford, Characterising the castration-resistant prostate cancer population: a systematic review. Int J Clin Pract, 2011. 65(11): p. 1180-92.
39. Denis, L. and G. P. Murphy, Overview of phase III trials on combined androgen treatment in patients with metastatic prostate cancer. Cancer, 1993. 72(12 Suppl): p. 3888-95.

40. Hellerstedt, B. A. and K. J. Pienta, The current state of hormonal therapy for prostate cancer. CA Cancer J Clin, 2002. 52(3): p. 154-79.
41. Berthold, D. R., et al., Docetaxel plus prednisone or mitoxantrone plus prednisone for advanced prostate cancer: updated survival in the TAX 327 study. J Clin Oncol, 2008. 26(2): p. 242-5.
42. de Bono, J. S., et al., Prednisone plus cabazitaxel or mitoxantrone for metastatic castration-resistant prostate cancer progressing after docetaxel treatment: a randomised open-label trial. Lancet, 2010. 376(9747): p. 1147-54.
43. Fizazi, K., et al., Abiraterone acetate for treatment of metastatic castration-resistant prostate cancer: final overall survival analysis of the COU-AA-301 randomised, double-blind, placebo-controlled phase 3 study. Lancet Oncol, 2012. 13(10): p. 983-92.
44. Kantoff, P. W., et al., Sipuleucel-T immunotherapy for castration-resistant prostate cancer. N Engl J Med, 2010. 363(5): p. 411-22.
45. Parker, C., et al., Alpha emitter radium-223 and survival in metastatic prostate cancer. N Engl J Med, 2013. 369(3): p. 213-23.
46. Rathkopf, D. E., et al., Updated Interim Efficacy Analysis and Long-term Safety of Abiraterone Acetate in Metastatic Castration-resistant Prostate Cancer Patients Without Prior Chemotherapy (COU-AA-302). Eur Urol, 2014. 66(5): p. 815-25.
47. Scher, H. I., et al., Increased survival with enzalutamide in prostate cancer after chemotherapy. N Engl J Med, 2012. 367(13): p. 1187-97.
48. Karja, V., et al., Tumour-infiltrating lymphocytes: A prognostic factor of PSA-free survival in patients with local prostate carcinoma treated by radical prostatectomy. Anticancer Res, 2005. 25(6C): p. 4435-8.
49. Vesalainen, S., et al., Histological grade, perineural infiltration, tumour-infiltrating lymphocytes and apoptosis as determinants of long-term prognosis in prostatic adenocarcinoma. Eur J Cancer, 1994. 30A(12): p. 1797-803.
50. Sfanos, K. S., et al., Phenotypic analysis of prostate-infiltrating lymphocytes reveals TH17 and Treg skewing. Clin Cancer Res, 2008. 14(11): p. 3254-61.
51. Dulos, J., et al., PD-1 blockade augments Th1 and Th17 and suppresses Th2 responses in peripheral blood from patients with prostate and advanced melanoma cancer. J Immunother, 2012. 35(2): p. 169-78.
52. Barach, Y. S., J. S. Lee, and X. Zang, T cell coinhibition in prostate cancer: new immune evasion pathways and emerging therapeutics. Trends Mol Med, 2011. 17(1): p. 47-55.
53. Galluzzi, L., et al., Immunogenic cell death in cancer and infectious disease. Nat Rev Immunol, 2017. 17(2): p. 97-111.
54. Ott, P. A., F. S. Hodi, and E. I. Buchbinder, Inhibition of Immune Checkpoints and Vascular Endothelial Growth Factor as Combination Therapy for Metastatic Melanoma: An Overview of Rationale, Preclinical Evidence, and Initial Clinical Data. Front Oncol, 2015. 5: p. 202.
55. Shariat, S. F., et al., Plasma levels of interleukin-6 and its soluble receptor are associated with prostate cancer progression and metastasis. Urology, 2001. 58(6): p. 1008-15.
56. Hobisch, A., et al., Interleukin-6 regulates prostate-specific protein expression in prostate carcinoma cells by activation of the androgen receptor. Cancer Res, 1998. 58(20): p. 4640-5.
57. Lee, S. O., et al., Interleukin-6 protects LNCaP cells from apoptosis induced by androgen deprivation through the Stat3 pathway. Prostate, 2004. 60(3): p. 178-86.
58. Liu, C., et al., Inhibition of constitutively active Stat3 reverses enzalutamide resistance in LNCaP derivative prostate cancer cells. Prostate, 2014. 74(2): p. 201-9.
59. Domingo-Domenech, J., et al., Interleukin 6, a nuclear factor-kappaB target, predicts resistance to docetaxel in hormone-independent prostate cancer and nuclear factor-kappaB inhibition by PS-1145 enhances docetaxel antitumor activity. Clin Cancer Res, 2006. 12(18): p. 5578-86.
60. Wu, C. T., et al., The role of IL-6 in the radiation response of prostate cancer. Radiat Oncol, 2013. 8: p. 159.
61. Ellis, L., et al., Development of a castrate resistant transplant tumor model of prostate cancer. Prostate, 2012. 72(6): p. 587-91.
62. Watson, P. A., et al., Context-dependent hormone-refractory progression revealed through characterization of a novel murine prostate cancer cell line. Cancer Res, 2005. 65(24): p. 11565-71.
63. Nupponen, N. N., et al., Genetic alterations in hormone-refractory recurrent prostate carcinomas. Am J Pathol, 1998. 153(1): p. 141-8.
64. Jiang, S. N., et al., Engineering of bacteria for the visualization of targeted delivery of a cytolytic anticancer agent. Mol Ther, 2013. 21(11): p. 1985-95.
65. Jiang, S. N., et al., Inhibition of tumor growth and metastasis by a combination of *Escherichia coli*-mediated cytolytic therapy and radiotherapy. Mol Ther, 2010. 18(3): p. 635-42.
66. Zheng, J. H., et al., Two-step enhanced cancer immunotherapy with engineered *Salmonella typhimurium* secreting heterologous flagellin. Sci Transl Med, 2017. 9(376).
67. Loeffler, M., et al., IL-18-producing *Salmonella* inhibit tumor growth. Cancer Gene Ther, 2008. 15(12): p. 787-94.
68. Loeffler, M., et al., *Salmonella typhimurium* engineered to produce CCL21 inhibit tumor growth. Cancer Immunol Immunother, 2009. 58(5): p. 769-75.
69. Shahabi, V., et al., Development of a *Listeria monocytogenes* based vaccine against prostate cancer. Cancer Immunol Immunother, 2008. 57(9): p. 1301-13.
70. Fensterle, J., et al., Cancer immunotherapy based on recombinant *Salmonella enterica* serovar *Typhimurium* aroA strains secreting prostate-specific antigen and cholera toxin subunit B. Cancer Gene Ther, 2008. 15(2): p. 85-93.
71. Ahmad, S., et al., Induction of effective antitumor response after mucosal bacterial vector mediated DNA vaccination with endogenous prostate cancer specific antigen. J Urol, 2011. 186(2): p. 687-93.

The invention claimed is:

1. A method of treating prostate cancer in a subject comprising co-administering *Escherichia coli* (*E. coli*) CP1 (ATTC Patent Deposit #PTA-127513) and an immune checkpoint inhibitor that binds to PD-1 or PD-L1 to the subject.

2. The method of claim 1, wherein co-administering results in increased production of biomarkers of inflammation.

3. The method of claim 2, wherein the biomarkers of inflammation are selected from the group consisting of TNFα, and IFNγ, IL-12, and CXCL9.

4. The method of claim 1, further comprising administering an additional cancer therapy selected from the group consisting of chemotherapy, radiation, and surgery, and immunotherapy.

5. The method of claim 1, wherein the immune checkpoint inhibitor is an antibody or antibody fragment.

6. The method of claim 5, wherein the immune checkpoint inhibitor binds to PD-L1.

7. The method of claim 1, wherein the immune checkpoint inhibitor is nivolumab, pembrolizumab, or pidilizumab.

* * * * *

SEQUENCE LISTING

<160> NUMBER OF SEQ ID NOS: 8

<210> SEQ ID NO 1

```
<211> LENGTH: 21
<212> TYPE: DNA
<213> ORGANISM: Artificial sequence
<220> FEATURE:
<223> OTHER INFORMATION: DNA primer

<400> SEQUENCE: 1
actcctacgg gaggcagcag t                                               21

<210> SEQ ID NO 2
<211> LENGTH: 19
<212> TYPE: DNA
<213> ORGANISM: Artificial sequence
<220> FEATURE:
<223> OTHER INFORMATION: DNA Primer

<400> SEQUENCE: 2
tattaccgcg gctgctggc                                                  19

<210> SEQ ID NO 3
<211> LENGTH: 18
<212> TYPE: DNA
<213> ORGANISM: Mus musculus

<400> SEQUENCE: 3
agatgcagca gatccgca                                                   18

<210> SEQ ID NO 4
<211> LENGTH: 19
<212> TYPE: DNA
<213> ORGANISM: Mus musculus

<400> SEQUENCE: 4
gttcttgccc atcagcacc                                                  19

<210> SEQ ID NO 5
<211> LENGTH: 20
<212> TYPE: DNA
<213> ORGANISM: Artificial sequence
<220> FEATURE:
<223> OTHER INFORMATION: Synthetic gRNA

<400> SEQUENCE: 5
gctaacgatc tctttgatga                                                 20

<210> SEQ ID NO 6
<211> LENGTH: 20
<212> TYPE: DNA
<213> ORGANISM: Artificial sequence
<220> FEATURE:
<223> OTHER INFORMATION: Synthetic gRNA

<400> SEQUENCE: 6
aaagacttga aggtgtatac                                                 20

<210> SEQ ID NO 7
<211> LENGTH: 20
<212> TYPE: DNA
<213> ORGANISM: Artificial sequence
<220> FEATURE:
<223> OTHER INFORMATION: Synthetic gRNA

<400> SEQUENCE: 7
tgtgcatatt tattgcatcg                                                 20
```

```
<210> SEQ ID NO 8
<211> LENGTH: 20
<212> TYPE: DNA
<213> ORGANISM: Artificial sequence
<220> FEATURE:
<223> OTHER INFORMATION: Synthetic gRNA

<400> SEQUENCE: 8
ggtttgataa gttctagctg                                              20
```